US011179484B2

(12) United States Patent
Schultz et al.

(10) Patent No.: US 11,179,484 B2
(45) Date of Patent: Nov. 23, 2021

(54) COMPOSITIONS AND METHODS OF TREATING MELANOMA

(71) Applicant: UNIVERSITY OF IOWA RESEARCH FOUNDATION, Iowa City, IA (US)

(72) Inventors: Michael K. Schultz, Iowa City, IA (US); Frances L. Johnson, Iowa City, IA (US); Somya Kapoor, Iowa City, IA (US); Dongyoul Lee, Iowa City, IA (US); Mengshi Li, Iowa City, IA (US); Molly Martin, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 72 days.

(21) Appl. No.: 16/312,846

(22) PCT Filed: Jun. 26, 2017

(86) PCT No.: PCT/US2017/039299
§ 371 (c)(1),
(2) Date: Dec. 21, 2018

(87) PCT Pub. No.: WO2017/223565
PCT Pub. Date: Dec. 28, 2017

(65) Prior Publication Data
US 2019/0321495 A1    Oct. 24, 2019

Related U.S. Application Data

(60) Provisional application No. 62/354,345, filed on Jun. 24, 2016, provisional application No. 62/370,125, filed on Aug. 2, 2016.

(51) Int. Cl.
| | |
|---|---|
| *A61K 51/04* | (2006.01) |
| *A61K 47/64* | (2017.01) |
| *A61P 35/00* | (2006.01) |
| *A61K 38/08* | (2019.01) |
| *A61K 47/54* | (2017.01) |
| *A61K 47/60* | (2017.01) |
| *A61K 31/167* | (2006.01) |
| *A61K 31/192* | (2006.01) |
| *A61K 31/437* | (2006.01) |

(Continued)

(52) U.S. Cl.
CPC ........ *A61K 51/0482* (2013.01); *A61K 31/167* (2013.01); *A61K 31/192* (2013.01); *A61K 31/437* (2013.01); *A61K 31/4427* (2013.01); *A61K 31/519* (2013.01); *A61K 38/08* (2013.01); *A61K 47/545* (2017.08); *A61K 47/546* (2017.08); *A61K 47/60* (2017.08); *A61K 47/64* (2017.08); *A61K 51/048* (2013.01); *A61K 51/0497* (2013.01); *A61P 35/00* (2018.01)

(58) Field of Classification Search
CPC ............... A61K 38/00; A61K 2123/00; A61K 2121/00; A61K 51/00; A61K 51/04; A61K 51/0482; A61K 47/00; A61K 47/546; A61K 47/545; A61K 47/60; A61K 31/00; A61K 31/167; A61K 31/192; A61K 31/437; A61K 31/4427; A61K 31/31; A61K 31/519; A61K 38/08; A61K 51/048; A61K 51/0497; A61K 45/00; A61K 45/06; A61K 51/08; A61K 51/088; A61K 31/4523; A61K 39/00; A61K 39/395; A61K 2300/00; A61K 47/64; A61P 35/00
USPC ...... 424/1.11, 1.49, 1.65, 1.69, 9.1, 9.2, 9.6; 534/7, 10–16; 514/1, 1.1, 19.2, 19.3, 514/19.4, 19.5, 19.6, 19.9, 21.1, 21.2, 514/21.3, 21.4, 21.5, 21.6, 21.7, 21.8, 514/21.9, 21.91; 530/300, 312, 317, 324, 530/325, 326, 327, 328, 329, 330, 331, 530/350
See application file for complete search history.

(56) References Cited

U.S. PATENT DOCUMENTS

| 4,559,157 A | 12/1985 | Smith et al. |
| 4,608,392 A | 8/1986 | Jacquet et al. |

(Continued)

FOREIGN PATENT DOCUMENTS

| CN | 104974745 A | 10/2015 |
| EP | 1574213 A1 | 9/2005 |

(Continued)

OTHER PUBLICATIONS

Froidevaux, S., et al., "A Novel DOTA-cx-Melanocyte-Stimulating Hormone Analog for Metastatic Melanoma Diagnosis", J Nucl Med 43, 1699-1706 (2002).

(Continued)

*Primary Examiner* — D. L. Jones
(74) *Attorney, Agent, or Firm* — Viksnins Harris Padys Malen LLP

(57) ABSTRACT

The invention provides compositions, kits and methods to treat a hyperproliferative disorder with an agent that increases expression of MCR1 and an MCR1 ligand. The invention also provides a method of treating drug-resistant melanoma, comprising administering an MCR1 ligand to a patient in need thereof. The present invention also provides in certain embodiments a melanoma-targeting conjugate comprising Formula (I): T-L-X wherein T is a MCR1 ligand, L is a linker, and X an anti-cancer composition, for the therapeutic treatment of a hyperproliferative disorder. The present invention also provides methods, kits and uses of the conjugate of Formula (I).

4 Claims, 17 Drawing Sheets

(51) Int. Cl.
*A61K 31/4427* (2006.01)
*A61K 31/519* (2006.01)

(56) References Cited

U.S. PATENT DOCUMENTS

| | | | |
|---|---|---|---|
| 4,820,508 | A | 4/1989 | Wortzman |
| 4,938,949 | A | 7/1990 | Borch et al. |
| 4,992,478 | A | 2/1991 | Geria |
| 6,338,834 | B1 | 1/2002 | Jurisson et al. |
| 6,607,709 | B1 | 8/2003 | Jurisson et al. |
| 6,680,045 | B2 | 1/2004 | Jurisson et al. |
| 7,008,925 | B1* | 3/2006 | Szardenings ............ A61P 17/02 514/13.5 |
| 7,321,027 | B2 | 1/2008 | Mahmood et al. |
| 7,915,245 | B2 | 3/2011 | Srivastava et al. |
| 8,143,271 | B2 | 3/2012 | Ibrahim et al. |
| 8,986,651 | B2* | 3/2015 | Miao ........................ C07K 7/54 424/1.69 |
| 9,801,922 | B2* | 10/2017 | Spitz .................... A61K 31/662 |
| 9,980,951 | B2 | 5/2018 | Schultz et al. |
| 10,052,304 | B2* | 8/2018 | Allen ................... A61K 31/555 |
| 10,729,669 | B2* | 8/2020 | Schultz ............. A61K 31/4706 |
| 2008/0032940 | A1 | 2/2008 | Kalyanaraman et al. |
| 2010/0278845 | A1 | 11/2010 | Heavner |
| 2011/0053938 | A1 | 3/2011 | Foley et al. |
| 2014/0112873 | A1 | 4/2014 | Gillies et al. |
| 2014/0128380 | A1 | 5/2014 | Blaskovich et al. |
| 2015/0038434 | A1 | 2/2015 | Yang et al. |
| 2015/0119341 | A1 | 4/2015 | Yang et al. |
| 2015/0284431 | A1 | 10/2015 | Cai et al. |
| 2016/0046688 | A1 | 2/2016 | Perricone et al. |
| 2016/0136309 | A1 | 5/2016 | Rosch et al. |
| 2018/0214402 | A1 | 8/2018 | Schultz et al. |

FOREIGN PATENT DOCUMENTS

| | | | |
|---|---|---|---|
| EP | 1847274 | A1 | 10/2007 |
| EP | 2698156 | A1 | 2/2014 |
| GB | 2185486 | A | 7/1987 |
| WO | 1990003798 | A2 | 4/1990 |
| WO | 1993015733 | A1 | 8/1993 |
| WO | 1993021963 | A1 | 11/1993 |
| WO | 2005023179 | A2 | 3/2005 |
| WO | 2009151708 | A2 | 12/2009 |
| WO | 2010129248 | A1 | 11/2010 |
| WO | 2011063366 | A1 | 5/2011 |
| WO | 2011063367 | A1 | 5/2011 |
| WO | 2013019975 | A1 | 2/2013 |
| WO | 2014072493 | A1 | 5/2014 |
| WO | 2014124384 | A1 | 8/2014 |

OTHER PUBLICATIONS

Manic, G , et al., "Chloroquine and hydroxychloroquine for cancer therapy", Mol Cell Oncol 1 (1), e29911, doi 10.4161/mco.29911, 11 pages (2014).
Raposinho, P , et al., "Melanoma targeting with alpha-melanocyte stimulating hormone analogs labeled with fac-[99mTc(CO)3]+: effect of cyclization on tumor-seeking properties", J Biol Inorg Chem 13, 449-459 (2008).
Wunderlin, R , et al., "Melanotropin Receptors II. Synthesis and Biological Activity of alpha-Melanotropin/Tobacco Mosaic Virus Disulfide Conjugates", Helvetica Chimica Acta 68, 12-22 (1985).
Yong, K , et al., "Towards translation of 212Pb as a clinical therapeutic; getting the lead in!", Dalton Trans 40, 6068-6076 (2011).
Ackerman, A , et al., "Outcomes of patients with metastatic melanoma treated with immunotherapy prior to or after BRAF inhibitors", Cancer 120(11), 1695-1701 (2014).
Adekola, K , et al., "Glucose transporters in cancer metabolism", Curr. Opin. Oncol. 24(6), 650-654 (2012).
Ahmad, I , et al., "Mitochondrial O2*- and H2O2 mediate glucose deprivation-induced stress in human cancer cells", J Biol Chem 280, 4254-4263 (2005).
Asundi, J , et al., "MAPK Pathway Inhibition Enhances the Efficacy of an Anti-Endothelin B Receptor Drug Conjugate by Inducing Target Expression in Melanoma", Mol Cancer Ther 13 (6), 1599-1610 (2014).
Aykin-Burns , et al., "Increased levels of superoxide and H2O2 mediate the differential susceptibility of cancer cells versus normal cells to glucose deprivation", Biochem J, 418(1), 29-37 (2009).
Beaino, W , et al., "PET Imaging of Very Late Antigen-4 in Melanoma: Comparison of 68Ga- and 64Cu-Labeled NODAGA and CB-TE1A1P-LLP2A Conjugates", J Nucl Med 55, 1856-1863 (2014).
Birch-Machin, M , et al., "An evaluation of the measurement of the activities of complexes I-IV in the respiratory chain of human skeletal muscle mitochondria", Biochem Med Metab Biol 51(1), 35-42 (1994).
Bradford, M , et al., "A rapid and sensitive method for the quantitation of microgram quantities of protein utilizing the principle of protein-dye binding", Anal Biochem 72, 248-254 (1976).
Burkitt, K , et al., "Phenylbutyrate interferes with the Fanconi anemia and BRCA pathway and sensitizes head and neck cancer cells to cisplatin", Molecular Cancer 7(24), 9 pages (2008).
Cecil Textbook of Medicine , Cecil Textbook of Medicine, 20th Edition, vol. 1 (1996).
Chen , "Mitochondrial membrane potential in living cells", Ann Rev Cell Biol 4, 155-181 (1988).
Dai, J., et al., "Malignant Cells Can Be Sensitized to Undergo Growth Inhibition and Apoptosis by Arsenic Trioxide Through Modulation of the Glutathione Redox System", Blood, vol. 93, No. 1, 268-277 (1999).
Ding, D , et al., "Bioprobes based on AIE fluorogens", Acc. Chem. Res. 46(11), 2441-2453 (2013).
Fath, M , et al., "Enhancement of carboplatin-mediated lung cancer cell killing by simultaneous disruption of glutathione and thioredoxin metabolism", Clin Cancer Res 17 (19), 6206-6217 (2011).
Fath, M , et al., "Mitochondrial electron transport chain blockers enhance 2-deoxy-D-glucose induced oxidative stress and cell killing in human colon carcinoma cells", Cancer Biol Ther 8(13), 1228-1236 (2009).
Figg, W , et al., "In vitro antitumor effect of hydroxyurea on hormone-refractory prostate cancer cells and its potentiation by phenylbutyrate", Anti-Cancer Drugs 5, 336-342 (1994).
Gabr, M , et al., "Synthesis and aggregation-induced emission properties of pyridine and pyridinium analogues of tetraphenylethylene", RSC Adv 5, 90226-90234 (2015).
Gius, D , et al., "Redox signaling in cancer biology", Antioxid Redox Signal 8(7-8), 1249-1252 (2006).
Goodall, M , et al., "Development of potent autophagy inhibitors that sensitize oncogenic BRAF V600E mutant melanoma tumor cells to vemurafenib", Autophagy 10(6), 1120-1136 (2014).
Gore, S , "In vitro basis for treatment with hypomethylating agents and histone deacetylase inhibitors: can epigenetic changes be used to monitor treatment?", Leukemia Research 33 Suppl 2, S2-S6 (2009).
Griffith, O , et al., "Determination of glutathione and glutathione disulfide using glutathione reductase and 2-vinylpyridine", Anal Biochem 106, 207-212 (1980).
Guo, H , et al., "Reduction of the Ring Size of Radiolabeled Lactam Bridge-Cyclized a-MSH Peptide, Resulting in Enhanced Melanoma Uptake", J Nucl Med 51, 418-426 (2010).
Gura, "Systems for Identifying New Drugs are Often Faulty", Science 278 (5340), 1041-1042 (1997).
Han, H , et al., "The rational design of a gemcitabine prodrug with AIE-based intracellular light-up characteristics for selective suppression of pancreatic cancer cells", Chem Commun (Camb) 51 (98): 17435-17438 (2015).
Howlader, N , et al., "SEER Cancer Statistics Review, 1975-2014", National Cancer Institute. Bethesda, MD, https://seer.cancer.gov/csr/1975_2014/, based on Nov. 2016 SEER data submission, posted to the SEER web site, Apr. 2017.

(56) References Cited

OTHER PUBLICATIONS

Hu, Q., et al., "Mitochondria-targeted cancer therapy using a light-up probe with aggregation-induced-emission characteristics", Angew. Chem. Int. Ed. Engl. 53(51), 14225-14229 (2014).
Indran, I, et al., "Recent advances in apoptosis, mitochondria and drug resistance in cancer cells", Biochim. Biophys Acta 1807(6), 735-745 (2011).
Johnson, J., et al., "Relationships between drug activity in NCI preclinical in vitro and in vivo models and early clinical trials", British J of Cancer 84, 1424-1431 (2001).
Jordan, E., et al., "Vemurafenib for the treatment of melanoma", Expert Opinion on Pharmacotherapy 13(17), 2533-2543 (2012).
Lai, F., et al., "Histone Deacetylases (HDACs) as Mediators of Resistance to Apoptosis in Melanoma and as Targets for Combination Therapy with Selective BRAF Inhibitors", Advances in Pharmacology 65, ISSN 1054-3589, 27-43 (2012).
Lee, A., "GRP78 induction in cancer: therapeutic and prognostic implications", Cancer Res 67, 3496-3499 (2007).
Leung, C., et al., "A photostable AIE luminogen for specific mitochondrial imaging and tracking", J. Am. Chern. Soc. 135(1), 62-65 (2013).
Lin, X., et al., "2-Deoxy-D-glucose-induced cytotoxicity and radiosensitization in tumor cells is mediated via disruptions in thiol metabolism", Cancer Res. 63 (12), 3413-3417 (2003).
Little, A., et al., "A New Combination Therapy for Metastatic Melanoma", University of Iowa Summer Undergraduate Research Day, University of Iowa, Iowa City, IA (2015).
Liu, et al., "A Small-Molecule Inhibitor of Glucose Transporter 1 Downregulates Glycolysis, Induces Cell-Cycle Arrest, and Inhibits Cancer Cell Growth In Vitro and In Vivo", Molecular Cancer Therapy, 11(8), 1672-1682 (2012).
Lowry, O., "Protein measurement with the Folin phenol reagent", J Biol Chem 193(1), 265-275 (1951).
Malo, A., et al., "4-Phenylbutyric acid reduces endoplasmic reticulum stress, trypsin activation, and acinar cell apoptosis while increasing secretion in rat pancreatic acini", Pancreas 42, 92-101 (2013).
Martin, M, et al., ""Click" cyclized gallium-68 labeled peptides for molecular imaging and therapy: Synthesis and preliminary in vitro and in vivo evaluation in a melanoma model system", Recent Results Cancer Res 194, 149-175 (2013).
Millard, Melissa, et al., "Preclinical Evaluation of Novel Triphenylphosphonium Salts with Broad-Spectrum Activity", PLoS One vol. 5 (10), e13131, 1-18 (2010).
Misra, UK, et al., "The role of Grp 78 in alpha 2-macroglobulin-induced signal transduction. Evidence from RNA interference that the low density lipoprotein receptor-related protein is associated with, but not necessary for, GRP 78-mediated signal transduction", J Biol Chem. 277(44), 42082-42087 (2002).
Modica-Napolitano, J., et al., "Delocalized lipophilic cations selectively target the mitochondria of carcinoma cells", Adv. Drug Delivery Rev. 49(1-2), 63-70 (2001).
Mueckler, M., "Facilitative glucose transporters", Eur. J. Biochem. 219(3), 713-725 (1994).
Murphy, M., et al., "Drug delivery to mitochondria: the key to mitochondrial medicine", Adv. Drug Delivery Rev. 41(2), 235-250 (2000).
Murphy, M., "How mitochondria produce reactive oxygen species", Biochem J 417(1), 1-13 (2009).
Murphy, M., et al., "Targeting antioxidants to mitochondria by conjugation to lipophilic cations", Annu. Rev. Pharmacol. Toxicol. 47, 629-656 (2007).
Murphy, M., "Targeting lipophilic cations to mitochondria", Biochim. Biophys. Acta 1777 (7-8), 1028-1031 (2008).
O'Dwyer, P., et al., "Phase 1 Trial of Buthionine Sulfoximine in Combination with Melphalan in Patients with Cancer" Oncol. vol. 14, No. 1, 249-256 (1996).
Patent Cooperation Treaty, International Searrching Authority, Search Report and Written Opinion for PCT/US17/039299, 9 pages, dated Sep. 14, 2017.
Phillips, J., et al., "Pilot study of sodium phenylbutyrate as adjuvant in cyclophosphamide-resistant endemic Burkitt's lymphoma", Transaction of the Royal Society of Tropical Medicine and Hygiene 101, 1265-1269 (2007).
Puck, T., et al., "Action of x-rays on mammalian cells. II. Survival curves of cells from normal human tissues", J Exp Med 106, 485-500 (1957).
Reedy, J., et al., "Synthesis and Evaluation of Tetraarylethylene-based Mono-, Bis-, and Tris(pyridinium) Derivatives for Image-Guided Mitochondria-Specific Targeting and Cytotoxicity of Metastatic Melanoma Cells", Bioconjugate Chem 27, 2424-2430 (2016).
Ripcke, J., et al., "Small-molecule targeting of the mitochondrial compartment with an endogenously cleaved reversible tag", ChemBioChem 10(10), 1689-1696 (2009).
Rohlena, J., et al., "Anticancer drugs targeting the mitochondrial electron transport chain", Antioxid. Redox Signaling 15(12), 2951-2974 (2011).
Schibler, J., et al., "Mitochondrial-Targeted DecylTriphenylphosphonium Enhances 2-Deoxy-D-Glucose Mediated Oxidative Stress and Clonogenic Killing of Multiple Myeloma Cells", PLOS One 11(11): e0167323 (2016).
Schniewind, B., et al., "Combination phenylbutyrate/gemcitabine therapy effectively inhibits in vitro and in vivo growth of NSCLC by intrinsic apoptotic pathways", Journal of Carcinogenesis 5(25), 11 pages (2006).
Simons, A., et al., "Glucose deprivation-induced metabolic oxidative stress and cancer therapy", J. Cancer Res. Ther. 5(Suppl 1) S2, 7 pages (2009).
Simons, A., et al., "Inhibition of glutathione and thioredoxin metabolism enhances sensitivity to perifosine in head and neck cancer cells", J Oncol 2009, 519563, 10 pages (2009).
Smith, R., et al., "Animal and human studies with the targeted antioxidant MitoQ", Annals of the New York Academy of Sciences 1201, 96-103 (2010).
Smith, R., et al., "Delivery of Bioactive Molecules to Mitochondria in vivo", PNAS, vol. 100, No. 9, 5407-5412 (2003).
Sousa, R., et al., "Treatment for metastatic melanoma: a new and evolving era", Int J Clin Pract 69(3), 273-280 (2015).
Spitz, D., et al., "Cytotoxicity and metabolism of 4-hydroxy-2-nonenal and 2-nonenal in H2O2-resistant cell lines. Do aldehydic by-products of lipid peroxidation contribute to oxidative stress?", Biochem J 267, 453-459 (1990).
Spitz, D., et al., "Glucose deprivation-induced oxidative stress in human tumor cells. A fundamental defect in metabolism?", Ann. N. Y. Acad. Sci., 899, 349-362 (2000).
Tolk, H., et al., "Complete remission of metastatic melanoma upon BRAF inhibitor treatment—what happens after discontinuation?", Melanoma Res 25(4), 362-366 (2015).
Tong, H., et al., "Fluorescent "light-up" bioprobes based on tetraphenylethylene derivatives with aggregation-induced emission characteristics", Chem Commun 35, 3705-3707 (2006).
Trnka, J., et al., "Lipophilic triphenylphosphonium cations inhibit mitochondrial electron transport chain and induce mitochondrial proton leak", PLoS One 10(4), e0121837, 14 pages (2015).
Tseng, W., et al., "Long-term survivors after immunotherapy for metastatic melanoma", Immunol Lett 139(1-2), 117-118 (2011).
Wang, Z., et al., "Long-term fluorescent cellular tracing by the aggregates of AIE bioconjugates", J. Am. Chem. Soc. 135(22), 8238-8245 (2013).
Yuan, H, et al., "Fluorescent and radiolabeled triphenylphosphonium probes for imaging mitochondria", Chem. Commun. 49 (88), 10361-10363 (2013).
Zain, J., et al., "Targeting Histone Deacetyalses in the Treatment of B-and T-cell Malignancies", Invest New Drugs 28(Suppl 1), S58-S78 (2010).
Zhang, G., et al., "General Synthetic Approach toward Geminal-Substituted Tetraarylethene Fluorophores with Tunable Emission Properties: X-ray Crystallography, Aggregation-Induced Emission and Piezofluorochromism", Chemistry Materials 26(15), 4433-4446 (2014).

\* cited by examiner

COMPOSITIONS AND METHODS OF TREATING MELANOMA

RELATED APPLICATIONS

This application claims priority to U.S. Provisional Application No. 62/354,345 that was filed on Jun. 24, 2016, and U.S. Provisional Application No. 62/370,125 that was filed on Aug. 2, 2016. The entire content of the applications referenced above are hereby incorporated by reference.

FEDERAL GRANT SUPPORT

The invention was made with government support under K25CA172218-01A1 awarded by the National Institutes of Health. The government has certain rights in the invention.

BACKGROUND

Melanoma is a cancer of the skin and is the fastest growing cancer incidence in the world today. Disease detected early can be removed by surgery, but when melanoma spreads to other parts of the body (called metastatic melanoma) it is almost uniformly fatal. The reason for this is that metastatic melanoma rapidly becomes resistance to all forms of treatment. One of the first new pharmaceutical therapies that appeared effective for melanoma (called vemurafenib) was approved in 2011. Vemurafenib targets patients with a gene mutation (BRAF$^{V600E}$) that is present in about half of melanoma patients. Although these patients respond well to the treatment, melanoma develops resistance to the therapy rapidly. Thus, the new therapy, which initially was heralded as the end of melanoma, extends life expectancy by only months. Vemurafenib is one of several BRAF inhibitors that are being used for melanoma therapy that target the BRAF protein. These BRAF inhibitors are now often used in combination with other inhibitors of proteins in the mitogen-activated protein kinase MAPK) pathway, a signaling pathway that is implicated in the cancerous phenotype of melanoma and other cancers. The MAPK pathway plays a role in the regulation of gene expression, cellular growth, and survival. Abnormal MAPK signaling may lead to increased or uncontrolled cell proliferation and resistance to apoptosis. Melanoma develops resistance to all of these therapies.

Recent introductions of a second class of drugs has resulted in approvals of new immunotherapies targeting regulator proteins of the immune system, which includes the recent development of anti-CTLA-4 monoclonal antibodies, Toll-like receptor (TLR) agonists, CD40 agonists, and anti-ganglioside monoclonal antibodies. These include CTLA-4 and PD1 inhibitors. Several other drugs that have different mechanisms of action are also approved for melanoma treatment, but the disease eventually develops resistance to all therapies for melanoma. There is no treatment for metastatic melanoma that overcomes resistance of melanoma cancer cells, which leads to a high mortality rate and the 5 year survival for patients diagnosed with metastatic melanoma is less than 20%.

Thus, there is a continuing need for compositions and methods for the treatment of melanoma in animals (e.g., humans). Combination therapies that overcome resistance mechanisms that arise in almost all melanoma patients are particularly needed.

SUMMARY

It was discovered that mitogen-activated protein kinase (MAPK) pathway inhibitors (e.g., vemurafenib, cobimetinib, trametinib, dabrafenib) upregulate MCR1 expression in metastatic melanoma cells. These discoveries significantly enhance the imaging and therapy potential of radiolabeled MCR1 ligands for medical imaging and therapy for metastatic melanoma.

The present invention provides in certain embodiments a melanoma-targeting conjugate comprising Formula I:

T-L-X wherein T is a radiolabeled MCR1 ligand,
L is a linker, and
X an anti-cancer composition,
for the therapeutic treatment of melanoma.

In certain embodiments, the radiolabeled MCR1 ligand is a peptide, or antibody or antibody fragment, or a small molecule.

In certain embodiments, T is Re[Cys-Cys-Glu-His-D-Phe-Arg-Trp-Cys-Arg-Pro-Val-NH$_2$].

In certain embodiments, the MCR1 ligand is radiolabeled with a radionuclide that is used for medical imaging and/or therapy of the cancerous tumors.

In certain embodiments, the radionuclide is Ga-68; In-111; Pb-203; F-18; C-11; Zr-89; Sc-44; Tc-99m or other medical radionuclide used for imaging.

In certain embodiments, the radionuclide is Y-90; Pb-212; Bi-212; Bi-213; At-211; Lu-177; Re-188; or other medical radionuclide used to treat the cancerous tumors.

In certain embodiments, L is a chemical linker that is inserted into a position between the peptide backbone that recognizes the MCR1 protein and the chelator that is used to radiolabel the composition using radionuclides for diagnostic imaging and/or therapy; and the linker improves the internalization of the composition into cells and improves the retention of the composition in tumors for more precise delivery of radiation to the cancerous tissue.

In certain embodiments, L is a hydrophobic linker consisting of an aliphatic carbon chain that connects the chelator to the peptide backbone.

In certain embodiments, L is a hydrophilic linker that includes heteroatom substitutions in the aliphatic chain that connects the chelator to the peptide backbone.

In certain embodiments, L is a mixture of hydrophilic and hydrophobic entities including piperidine insertions of amino acid insertions to lengthen the chain and modulate the pharmacodynamics properties of the composition.

In certain embodiments, L is PEG$_n$, wherein n is 1-10. In certain embodiments, n is 2, 4 or 8 PEG subunits. In certain embodiments, n is 4. (FIG. 9)

In certain embodiments, L is an aliphatic (ALP) linker of 2 or 4 carbons. (FIG. 9) In certain embodiments, L is a piperidine (PIP) based linker with mixed characteristics. (FIG. 9)

In certain embodiments, X is a chelating agent (also called a "chelator").

In certain embodiments, X is radiolabeled with a radionuclide that is used for medical imaging and/or therapy of the cancerous tumors.

In certain embodiments, the chelator is radiometallated or radiolabeled with a radionuclide that is suitable for the therapeutic treatment and radiologic (or non-radiolgic) imaging of melanoma or other MCR1 expression cancerous malignancy (e.g., medulloblastoma).

In certain embodiments, the radionuclide is Ga-68; In-111; Pb-203; F-18; C-11; Zr-89; Sc-44; Tc-99m or other medical radionuclide used for imaging.

In certain embodiments, the radionuclide is Y-90; Pb-212; Bi-212; Bi-213; At-211; Lu-177; Re-188; or other medical radionuclide used to treat the cancerous tumors.

In certain embodiments, the chelating agent is DOTA or other chelator that is used to bind the radionuclide for diagnostic imaging or therapy for cancer or other disease.

In certain embodiments, the chelator is based on S-2-(4-Nitrobenzyl)-1,4,7,10-tetraazacyclododecane or other variation on this cyclododecane.

In certain embodiments, the chelator is based on 1,4,7,10-Tetraazacyclododecane-1,4,7-tri(carbamoylmethyl)-10-acetic acid.

In certain embodiments, the chelator is based on S-2-(4-Nitrobenzyl)-1,4,7,10-tetraazacyclododecane tetraacetic acid.

In certain embodiments, the chelator is based on S-2-(4-Aminobenzyl)-1,4,7,10-tetraazacyclododecane tetraacetic acid.

In certain embodiments, the chelator is based on S-2-(4-Aminobenzyl)-1,4,7,10-tetraazacyclododecane tetra-tert-butylacetate.

In certain embodiments, the chelator is based on S-2-(4-Isothiocyanatobenzyl)-1,4,7,10-tetraazacyclododecane tetraacetic acid.

In certain embodiments, the chelator is based on 1,4,7,10-Tetraazacyclododecane-1,4,7-tris-tert-butyl acetate-10-acetic acid.

In certain embodiments, the chelator is based on 1,4,7,10-Tetraazacyclododecane-1,4,7-tris-tert-butyl acetate-10succinimidyl acetate.

In certain embodiments, the chelator is based on 1,4,7,10-Tetraazacyclododecane-1,4,7-tris-tert-butyl acetate-10-maleimidoethylacetamide.

In certain embodiments, the chelator is based on 1,4,7,10-Tetraazacyclododecane-1,4,7-tris-acetic acid-10-maleimidoethylacetamide.

In certain embodiments, the chelator is based on 1,4,7,10-Tetraazacyclododecane-1,4,7-tris-tert-butyl acetate-10-(N-a-Fmoc-N-e-acetamido-L-lysine).

In certain embodiments, the chelator is based on 1,4,7,10-Tetraazacyclododecane-1,4,7-tris(t-butyl acetate)-10-(3-butynylacetamide).

In certain embodiments, the chelator is based on 1,4,7,10-Tetraazacyclododecane-1,4,7-tris(t-butyl-acetate)-10-(aminoethylacetamide).

In certain embodiments, the chelator is based on 1,4,7,10-Tetraazacyclododecane-1,4,7-tris-tert-butyl acetate-10-(azidopropyl ethylacetamide).

In certain embodiments, the chelator is based on 1,4,7,10-Tetraazacyclododecane-1,4,7-tris(t-butyl acetate)-10-(4-aminobutyl)acetamide.

In certain embodiments, the chelator is based on 1,4,7,10-Tetraazacyclododecane-1,4,7,10-tetraacetic acid mono-N-hydroxysuccinimide ester.

In certain embodiments, the chelator is based on 1,4,7,10-Tetraazacyclododecane-1,4,7-tris(acetic acid)-10-(2-thioethyl)acetamide or other variation of DOTA.

In certain embodiments, the chelator is based on S-2-(4-Aminobenzyl)-diethylenetriamine pentaacetic acid or other variation of DTPA.

In certain embodiments, the chelator is based on 3,6,9,15-Tetraazabicyclo[9.3.1] pentadeca-1(15),11,13-triene-4-S-(4-aminobenzyl)-3,6,9-triacetic acid or other variation on this pentadeca macrocycle.

In certain embodiments, the chelator is based on 1-Oxa-4,7,10-tetraazacyclododecane-5-S-(4-aminobenzyl)-4,7,10-triacetic acid or other variation on oxo-substituted macrocycle.

In certain embodiments, the chelator is based on 2-S-(4-Isothiocyanatobenzyl)-1,4,7-triazacyclononane-1,4,7-triacetic acid or other variation on this cyclononane.

In certain embodiments, the chelator is based on 1-(4-isothiocyanatophenyl)-3-[6,17-dihydroxy-7,10,18,21-tetraoxo-27-(N-acetylhydroxylamino)-6,11,17,22-tetraazaheptaeicosine] thiourea or other variation on deferoxamine.

The present invention provides in certain embodiments a conjugate consisting of DOTA-PEG4-VMT-(MCR1 ligand).

In certain embodiments, the present invention consists of DOTA-PEG4-Re[Cys-Cys-Glu-His-D-Phe-Arg-Trp-Cys-Arg-Pro-Val-NH2].

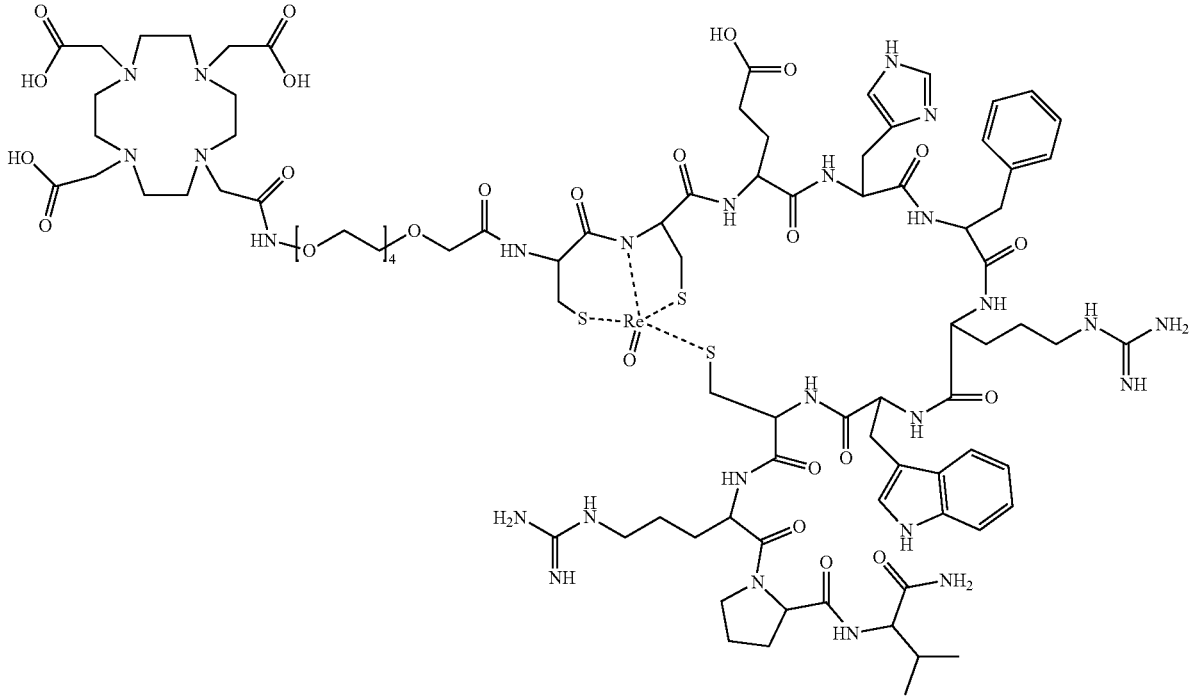

Chemical Formula: $C_{89}H_{135}N_{26}O_{26}ReS_3$
Molecular Weight: 2267.60

In certain embodiments, the present invention consists of the conjugate VMT1 (FIG. 22A), VMT2 (FIG. 22B), or PSC-PEG-CLICK (FIG. 22C).

In certain embodiments, DOTA is radiolabeled.

In certain embodiments, the radiolabel is Pb-203.

The present invention provides in certain embodiments a method of treating hyperproliferative disorder in a patient in need thereof, comprising administering the conjugate described above. In certain embodiments, the hyperproliferative disorder is melanoma. In certain embodiments, the conjugate is administered orally or parenterally.

In certain embodiments, the method further comprises administering an anti-cancer composition.

In certain embodiments, the anti-cancer composition comprises phenyl butyric acid (PBA) or a pharmaceutically acceptable salt thereof, chloroquine, hydroxychloroquine (laquenil, Axemal (in India), Dolquine and Quensyl, or a pharmaceutical drug that is an antimalarlial or inhibits interactions between lysosomes and autophagasomes that overcome resistance that is linked to autophagy; derivative of triphenylphosphonium (TPP), PBA, a histone deacetylation inhibitor, a MAPK pathway inhibitor, such as a MEK inhibitor, a RAS inhibitor, and/or RAF inhibitor.

In certain embodiments, the present invention further comprises administering an agent that increases expression of MCR1.

In certain embodiments, the present invention further comprises administering an immunotherapy targeting regulator protein of the immune system. In certain embodiments, the immunotherapy includes an anti-CTLA-4 monoclonal antibody, Toll-like receptor (TLR) agonist, CD40 agonist, and/or anti-ganglioside monoclonal antibody. In certain embodiments, the immunotherapy includes CTLA-4 and PD1 inhibitors.

In certain embodiments, the hyperproliferative disorder is melanoma.

In certain embodiments, the agent that increases expression of MCR1 is vemurafenib, PBA, a histone deacetylation inhibitor and/or another MAPK pathway inhibitor, a RAS inhibitor, and/or RAF inhibitor.

In certain embodiments, the histone deacetylase inhibitor is Vorinastat.

In certain embodiments, the MAPK pathway inhibitor is a MEK inhibitor.

In certain embodiments, the MEK inhibitor is cobimetinib or trametinib.

In certain embodiments, the agent that increases expression of MCR1 is administered separately, sequentially or simultaneously with the conjugate.

In certain embodiments, the agent that increases expression of MCR1 is administered from about one to about six month before the administration of the conjugate.

In certain embodiments, the agent is administered orally or parenterally.

In certain embodiments, the agent is administered subcutaneously.

In certain embodiments, the conjugate is administered orally or parenterally.

In certain embodiments, administration of the agent begins about 1 to about 10 days before administration of the conjugate.

In certain embodiments, administration of the agent and administration of the conjugate begin on the same day.

In certain embodiments, the method further comprises administering an anti-cancer composition.

In certain embodiments, the anti-cancer composition comprises phenyl butyric acid (PBA) or a pharmaceutically acceptable salt thereof, chloroquine, hydroxychloroquine (laquenil, Axemal (in India), Dolquine and Quensyl, or a pharmaceutical drug that is an antimalarlial or inhibits interactions between lysosomes and autophagasomes that overcome resistance that is linked to autophagy; derivative of triphenylphosphonium (TPP), PBA, a histone deacetylation inhibitor, a MAPK pathway inhibitor, such as a MEK inhibitor, a RAS inhibitor, and/or RAF inhibitor.

In certain embodiments, the histone deacetylation inhibitor is Vorinastat.

In certain embodiments, the MAPK pathway inhibitor is a MEK inhibitor.

In certain embodiments, the MEK inhibitor is cobimetinib or trametinib.

In certain embodiments, the conjugate is administered in a single dose.

In certain embodiments, the conjugate is administered in multiple doses.

In certain embodiments, the conjugate is administered sequentially daily for several days.

In certain embodiments, the conjugate is administered once per week for 1 month.

In certain embodiments, the conjugate is administered once per week for up to 6 months.

In certain embodiments, the conjugate is administered in a dose of 1 mCi for medical imaging.

In certain embodiments, the conjugate is administered in a dose of up to 10 mCi for medical imaging.

In certain embodiments, the conjugate is administered in a dose of up to 50 mCi for medical imaging.

In certain embodiments, the conjugate is administered in a dose of 0.1 mCi for medical treatment of the cancerous tumors.

In certain embodiments, the conjugate is administered in a dose of up to 1 mCi for medical treatment of the cancerous tumors.

In certain embodiments, the conjugate is administered in a dose of up to 10 mCi for medical treatment of the cancerous tumors.

In certain embodiments, the conjugate is administered in a dose of up to 100 mCi for medical treatment of the cancerous tumors.

In certain embodiments, the conjugate is administered for more than a month.

In certain embodiments, the conjugate is administered for more than a year.

In certain embodiments, the conjugate is administered at a dosage of at least 1500 mg/day.

The present invention provides in certain embodiments a kit comprising the conjugate described above, a container, and a package insert or label indicating the administration of the conjugate with vemurafenib for treating melanoma.

The present invention provides in certain embodiments a product comprising the conjugate described above, and vemurafenib; as a combined preparation for separate, simultaneous or sequential use in the treatment of melanoma.

The present invention provides in certain embodiments a method of treating drug-resistant melanoma, comprising administering the conjugate described above to a patient in need thereof.

In certain embodiments, the melanoma is resistant to vemurafenib treatment.

The present invention provides in certain embodiments a use of the conjugate described above; and one or more anti-cancer agents for the therapeutic treatment of melanoma.

In certain embodiments, the cancer is vemurafenib-resistant melanoma.

The present invention provides in certain embodiments a use of the conjugate described above wherein:

a) the conjugate is administered simultaneously with the one or more anti-cancer agents; or b) the conjugate and the one or more anti-cancer agents are administered sequentially; or c) administration of the one or more anti-cancer agents begins about 1 to about 10 days before administration of the conjugate; or d) administration of the conjugate thereof begins about 1 to about 10 days before administration of the one or more anti-cancer agents; or e) administration of conjugate and administration of the one or more anti-cancer agents begins on the same day.

In certain embodiments, the conjugate is administered in combination with vemurafenib, and the cancer is melanoma.

In certain embodiments, conjugate, is administered in combination with vemurafenib and chloroquine, and the cancer is melanoma.

The present invention provides in certain embodiments, a method of treating a cell that has upregulated MCR1 expression as compared to a comparable wildtype cell comprising contacting the cell with an MCR1 ligand or with the conjugate described above. As used herein, an "MCR1 ligand" is a ligand that binds specifically to the MCR1 receptor.

In certain embodiments, the upregulation is a result of prior contact with vemurafenib, PBA, a histone deacetylation inhibitor and/or another MEK inhibitor.

In certain embodiments, the upregulation is a result of prior contact with vemurafenib.

In certain embodiments, the upregulation is a result of prior contact with PBA.

In certain embodiments, the ligand is a peptide.

In certain embodiments, the peptide is radiolabeled.

The present invention provides in certain embodiments, a method of treating hyperproliferative disorder in a patient in need thereof, comprising (a) administering an agent that increases expression of MCR1, and (b) administering an MCR1 ligand.

In certain embodiments, the hyperproliferative disorder is melanoma.

In certain embodiments, the agent that increases expression of MCR1 is vemurafenib, PBA, a histone deacetylation inhibitor, such as Vorinastat or other histone deacetylase inhibitor, and/or another MAPK pathway inhibitor, such as a MEK inhibitor (e.g., cobimetinib, trametinib), a RAS inhibitor, and/or RAF inhibitor.

In certain embodiments, the MCR1 ligand is a peptide.

In certain embodiments, the peptide is radiolabeled.

In certain embodiments, the agent that increases expression of MCR1 is administered separately, sequentially or simultaneously with the MCR1 ligand.

In certain embodiments, the agent that increases expression of MCR1 is administered from about one day to about 6 months before the administration of the MCR1 ligand.

In certain embodiments, the agent is administered orally or parenterally.

In certain embodiments, the agent is administered subcutaneously.

In certain embodiments, the MCR1 ligand is administered orally or parenterally.

In certain embodiments, the administration of the agent begins about 1 to about 10 days before administration of the MCR1 ligand.

In certain embodiments, the administration of the agent and administration of the MCR1 ligand begin on the same day.

In certain embodiments, the method further comprises administering an anti-cancer composition.

In certain embodiments, the anti-cancer composition comprises a combination of phenyl butyric acid or one of its salts such as sodium phenylbutyrate (referred to collectively as PBA) or a pharmaceutically acceptable salt thereof, chloroquine, hydroxychloroquine (laquenil, Axemal (in India), Dolquine and Quensyl, or a pharmaceutical drug that is an antimalarlial or inhibits interactions between lysosomes and autophagasomes that overcome resistance that is linked to autophagy; and MAPK pathway inhibitors such as vemurafenib, cobimetinib, and/or other inhibitors of the MAPK pathway, a derivative of triphenylphosphonium (TPP), PBA, a histone deacetylation inhibitor, such as Vorinastat or other histone deacetylase inhibitor, and/or another MAPK pathway inhibitor, such as a MEK inhibitor (e.g., cobimetinib, trametinib), a RAS inhibitor, and/or RAF inhibitor.

In certain embodiments, the combination includes a radiolabeled MCR1 ligand that is designed to bind to the MCR1 protein on or in cells in the cancerous tumors of the patient.

In certain embodiments, the MCR1 ligand is radiolabeled with a radionuclide that is used for medical imaging and/or therapy of the cancerous tumors by techniques such as single photon emission computed tomography (SPECT) or positron emission computed tomography (PET).

In certain embodiments, the radionuclide is Ga-68; In-111; Pb-203; F-18; C-11; Zr-89; Sc-44; Tc-99m or other medical radionuclide used for imaging.

In certain embodiments, the radionuclide is Y-90; Pb-212; Bi-212; Bi-213; At-211; Lu-177; Re-188; or other medical radionuclide used to treat the cancerous tumors.

In certain embodiments, the radiolabeled MCR1 ligand is administered in a single dose.

In certain embodiments, the radiolabeled MCR1 ligand is administered in multiple doses.

In certain embodiments, the radiolabeled MCR1 ligand is administered sequentially daily for several days.

In certain embodiments, the radiolabeled MCR1 ligand is administered once per week for 1 month.

In certain embodiments, the radiolabeled MCR1 is administered once per week for up to 6 months.

In certain embodiments, the radiolabeled MCR1 ligand is administered in a dose of 1 mCi for medical imaging.

In certain embodiments, the radiolabeled MCR1 ligand is administered in a dose of up to 10 mCi for medical imaging.

In certain embodiments, the radiolabeled MCR1 ligand is administered in a dose of up to 50 mCi for medical imaging.

In certain embodiments, the radiolabeled MCR1 ligand is administered in a dose of 0.1 mCi for medical treatment of the cancerous tumors.

In certain embodiments, the radiolabeled MCR1 ligand is administered in a dose of up to 1 mCi for medical treatment of the cancerous tumors.

In certain embodiments, the radiolabeled MCR1 ligand is administered in a dose of up to 10 mCi for medical treatment of the cancerous tumors.

In certain embodiments, the radiolabeled MCR1 ligand is administered in a dose of up to 100 mCi for medical treatment of the cancerous tumors.

The present invention provides in certain embodiments, a method of treating drug-resistant melanoma, comprising administering an MCR1 ligand to a patient in need thereof.

In certain embodiments, the melanoma is resistant to vemurafenib treatment.

The present invention provides in certain embodiments, a combination of a) an agent that increases expression of MCR1, and b) MCR1 ligand for the prophylactic or therapeutic treatment of hyperproliferative disorder.

In certain embodiments, the hyperproliferative disorder is melanoma.

In certain embodiments, the combination provides a synergistic effect in treating the hyperproliferative disorder.

In certain embodiments, the agent that increases expression of MCR1 is vemurafenib, PBA, a histone deacetylation inhibitor and/or another MEK inhibitor.

In certain embodiments, the agent that increases expression of MCR1 is vemurafenib.

In certain embodiments, the agent that increases expression of MCR1 is PBA.

In certain embodiments, the MCR1 ligand is a peptide.

In certain embodiments, the peptide is radiolabeled.

The present invention provides in certain embodiments, a method of treating melanoma in a patient in need thereof that has received treatment with vemurafenib, PBA, a histone deacetylation inhibitor and/or another MEK inhibitor, or other MAPK pathway inhibitor, comprising administering an agent that increases expression of MCR1 in combination with an MCR1 ligand to the patient.

The present invention provides in certain embodiments, a kit comprising an agent that increases expression of MCR1, a MCR1 ligand, a container, and a package insert or label indicating the administration of the agent with the MCR1 ligand for treating a hyperproliferative disorder.

As a combined treatment the combination treatment effectively destroys metastatic melanoma cancer cells. In certain embodiments, the hyperproliferative disorder is cancer. In certain embodiments, the cancer is drug-resistant. As used herein, the term "drug-resistant" is reduction in effectiveness of a drug in killing malignant cells; reducing cancerous tumor size and rate of growth; and ameliorating the symptoms a disease or condition. In certain embodiments, the drug's effectiveness is reduced by at least about 10%, 20%, 30%, 40%, 50%, 60%, 70%, 80%, 90%, or even 100%, as compared to its effects when first administered to the mammal.

In certain embodiments, the cancer is melanoma. In certain embodiments, the melanoma is resistant to vemurafenib treatment.

In certain embodiments, the present invention provides a method of treating a cell that has upregulated MCR1 expression as compared to a comparable wildtype cell comprising contacting the cell with an MCR1 ligand or the conjugate of described above.

In certain embodiments, the upregulation is a result of prior contact with vemurafenib, PBA, a histone deacetylation inhibitor and/or another MEK inhibitor.

In certain embodiments, the upregulation is a result of prior contact with vemurafenib.

In certain embodiments, the upregulation is a result of prior contact with PBA.

In certain embodiments, the present invention provides a method of treating hyperproliferative disorder in a patient in need thereof, comprising (a) administering an agent that increases expression of MCR1, and (b) administering the conjugate as described above.

In certain embodiments, the hyperproliferative disorder is melanoma.

In certain embodiments, the agent that increases expression of MCR1 is vemurafenib, PBA, a histone deacetylation inhibitor and/or another MAPK pathway inhibitor, a RAS inhibitor, and/or RAF inhibitor.

In certain embodiments, the histone deacetylase inhibitor is Vorinastat.

In certain embodiments, the MAPK pathway inhibitor is a MEK inhibitor.

In certain embodiments, the MEK inhibitor is cobimetinib or trametinib.

In certain embodiments, the agent that increases expression of MCR1 is administered separately, sequentially or simultaneously with the MCR1 ligand.

In certain embodiments, the agent that increases expression of MCR1 is administered from about one to about six months before the administration of the conjugate.

In certain embodiments, the agent is administered orally or parenterally.

In certain embodiments, the agent is administered subcutaneously.

In certain embodiments, the conjugate is administered orally or parenterally.

In certain embodiments, administration of the agent begins about 1 to about 10 days before administration of the conjugate.

In certain embodiments, administration of the agent and administration of the conjugate begin on the same day.

In certain embodiments, the method further comprises administering an anti-cancer composition.

In certain embodiments, the anti-cancer composition comprises phenyl butyric acid (PBA) or a pharmaceutically acceptable salt thereof, chloroquine, hydroxychloroquine (laquenil, Axemal (in India), Dolquine and Quensyl, or a pharmaceutical drug that is an antimalarlial or inhibits interactions between lysosomes and autophagasomes that overcome resistance that is linked to autophagy; derivative of triphenylphosphonium (TPP), PBA, a histone deacetylation inhibitor, a MAPK pathway inhibitor, such as a MEK inhibitor, a RAS inhibitor, and/or RAF inhibitor.

In certain embodiments, the histone deacetylation inhibitor is Vorinastat.

In certain embodiments, the MAPK pathway inhibitor is a MEK inhibitor.

In certain embodiments, the MEK inhibitor is cobimetinib or trametinib.

In certain embodiments, the radiolabeled conjugate is administered in a single dose.

In certain embodiments, the radiolabeled conjugate is administered in multiple doses.

In certain embodiments, the radiolabeled conjugate is administered sequentially daily for several days.

In certain embodiments, the radiolabeled conjugate is administered once per week for 1 month.

In certain embodiments, the radiolabeled conjugate is administered once per week for up to 6 months.

In certain embodiments, the radiolabeled conjugate is administered in a dose of 1 mCi for medical imaging.

In certain embodiments, the radiolabeled conjugate is administered in a dose of up to 10 mCi for medical imaging.

In certain embodiments, the radiolabeled conjugate is administered in a dose of up to 50 mCi for medical imaging.

In certain embodiments, the radiolabeled conjugate is administered in a dose of 0.1 mCi for medical treatment of the cancerous tumors.

In certain embodiments, the radiolabeled conjugate is administered in a dose of up to 1 mCi for medical treatment of the cancerous tumors.

In certain embodiments, the radiolabeled conjugate is administered in a dose of up to 10 mCi for medical treatment of the cancerous tumors.

In certain embodiments, the radiolabeled conjugate is administered in a dose of up to 100 mCi for medical treatment of the cancerous tumors.

In certain embodiments, the conjugate is administered for more than a month.

In certain embodiments, the conjugate is administered for more than a year.

In certain embodiments, the radiolabeled conjugate is administered at a dosage of at least 1500 mg/day.

In certain embodiments, the present invention provides a method of treating drug-resistant melanoma, comprising administering the conjugate as described above to a patient in need thereof.

In certain embodiments, the melanoma is resistant to vemurafenib treatment.

In certain embodiments, the present invention provides a combination of a) an agent that increases expression of MCR1, and b) the conjugate as described above for the prophylactic or therapeutic treatment of hyperproliferative disorder.

In certain embodiments, the hyperproliferative disorder is melanoma.

In certain embodiments, the combination provides a synergistic effect in treating the hyperproliferative disorder.

In certain embodiments, the agent that increases expression of MCR1 is vemurafenib, PBA, a histone deacetylation inhibitor and/or another MEK inhibitor.

In certain embodiments, the agent that increases expression of MCR1 is vemurafenib.

In certain embodiments, the agent that increases expression of MCR1 is PBA.

In certain embodiments, the present invention provides a method of treating melanoma in a patient in need thereof that has received treatment with vemurafenib, PBA, a histone deacetylation inhibitor and/or another MEK inhibitor or other MAPK pathway inhibitor, comprising administering an agent that increases expression of MCR1 in combination with the conjugate as described above to the patient.

In certain embodiments, the present invention provides a kit comprising an agent that increases expression of MCR1, the conjugate of as described above, a container, and a package insert or label indicating the administration of the agent with the conjugate as described above for treating a hyperproliferative disorder.

BRIEF DESCRIPTION OF THE DRAWINGS

FIGS. 14A-4B. (A) Co-administration (i. v. or i.p.) of PBA (120 mg/kg) significantly blocked kidney uptake, but did not affect tumor accumulation of [$^{203}$Pb]DOTA-MCR1 (0.037 MBq) at 2h p.i. in mice; Tumor and kidneys were harvested, weighed and assayed by NaI detector. Results are ID %/g tissue±SD; P<0.01; **P<0.0001. (B Right) Pre-administered of PBA (i.p. 60 mg/kg) and BRAF$_i$ (vemurafenib; p.o. 5 mg/kg) 3 h prior to tail vein injection of 13 MBq [$^{203}$Pb]DOTA-MCR1 in human (A2058) melanoma-bearing athymic nu/nu mice (SPECT image 1h p.i.); (B Left) An identical animal was administered an identical dose of [$^{203}$Pb]DOTA-MCR1 without PBA/BRAF$_i$ (saline). Images were identically processed and analyzed using Inveon Workplace software (identicle contrast, intensity, etc.). These data support the hypothesis that combining MCR1-RT with PBA that enhance MCR1-RT by reducing kidney uptake and improving tumor uptake of MCR1-peptides.

Multifocal, scattered glomerular capillary loops are smudged and almost acellular than usual (glomerular sclerosis) (encircled). Analysis by co-investigators Gibson-Corely and Zepeda-Orozco at the University of Iowa. Importantly, the peptide proposed in the current application (click-cyclized) reduces kidney accumulation (no blocking) by 3-fold and improves tumor:kidney ratio 7-fold.

Figure 19:
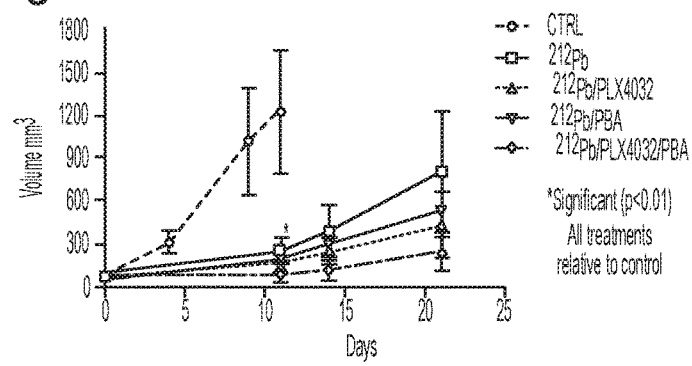

FIG. 19. Representative tumor growth curve for human melanoma tumor bearing mice treated with 100 µCi (3.7MBq) of [$^{212}$Pb]DOTA-MCR1 alone ($^{212}$Pb) and combined with BRAF$_i$ ($^{212}$Pb/PLX4032); PBA ($^{212}$Pb/PBA) and a triple combination ($^{212}$Pb/PLX4032/PBA) relative to untreated controls. Tumor size of untreated controls reached IACUC protocol limits (1500 mm$^3$) by 15 days post study initiation (at 100 mm$^3$ tumor size). The most pronounced tumor response was observed in the triple combination treatment group (n=7, mean+/−SEM).

Figures 20A, 20B:
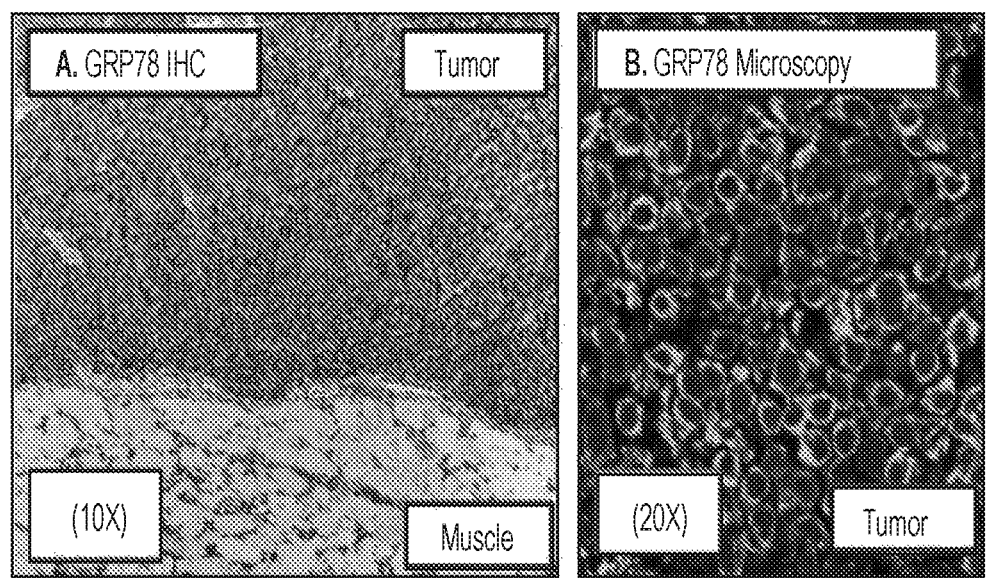

FIGS. 20A-20B. GRP78 analysis of kidney and tumor PE samples are used to examine the role of ER stress in the fibrogenesis in kidney tubules and in tumor response with and without the inclusion of PBA, which is known to relieve ER stress. See also FIGS. 12A-12D for the potential role of ER stress in the development of resistance in melanoma.

Figure 21:
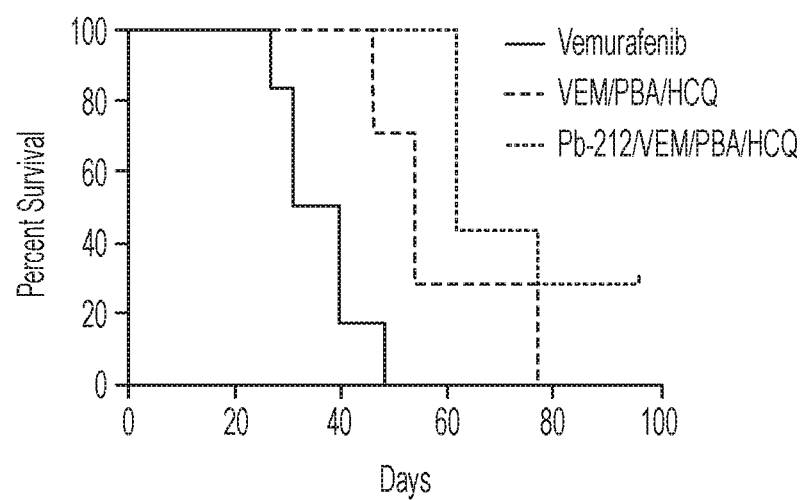

FIG. 21. Survival of mice bearing human metastatic melanoma xenografts (A375) treated with a single dose (i.v.) of [$^{212}$Pb]DOTA-MCR1, shown as $^{212}$Pb (~100 µCi) with and without a combination of BRAE (vemurafenib 10 mg/kg b.i.d); PBA (120 mg/kg i.p.); and hydroxychloroquine. Treatments were standardized to begin when tumors reach 100 mm$^3$. Mice were euthanized according to IACUC protocols (when tumors reached 1500 mm$^3$ or ulceration appeared) or at about 100d. These data support the hypothesis that [$^{212}$Pb]DOTA-MCR1 therapy has the potential to improve outcomes for metastatic melanoma patients relative to standard of care therapy.

Figure 22A:
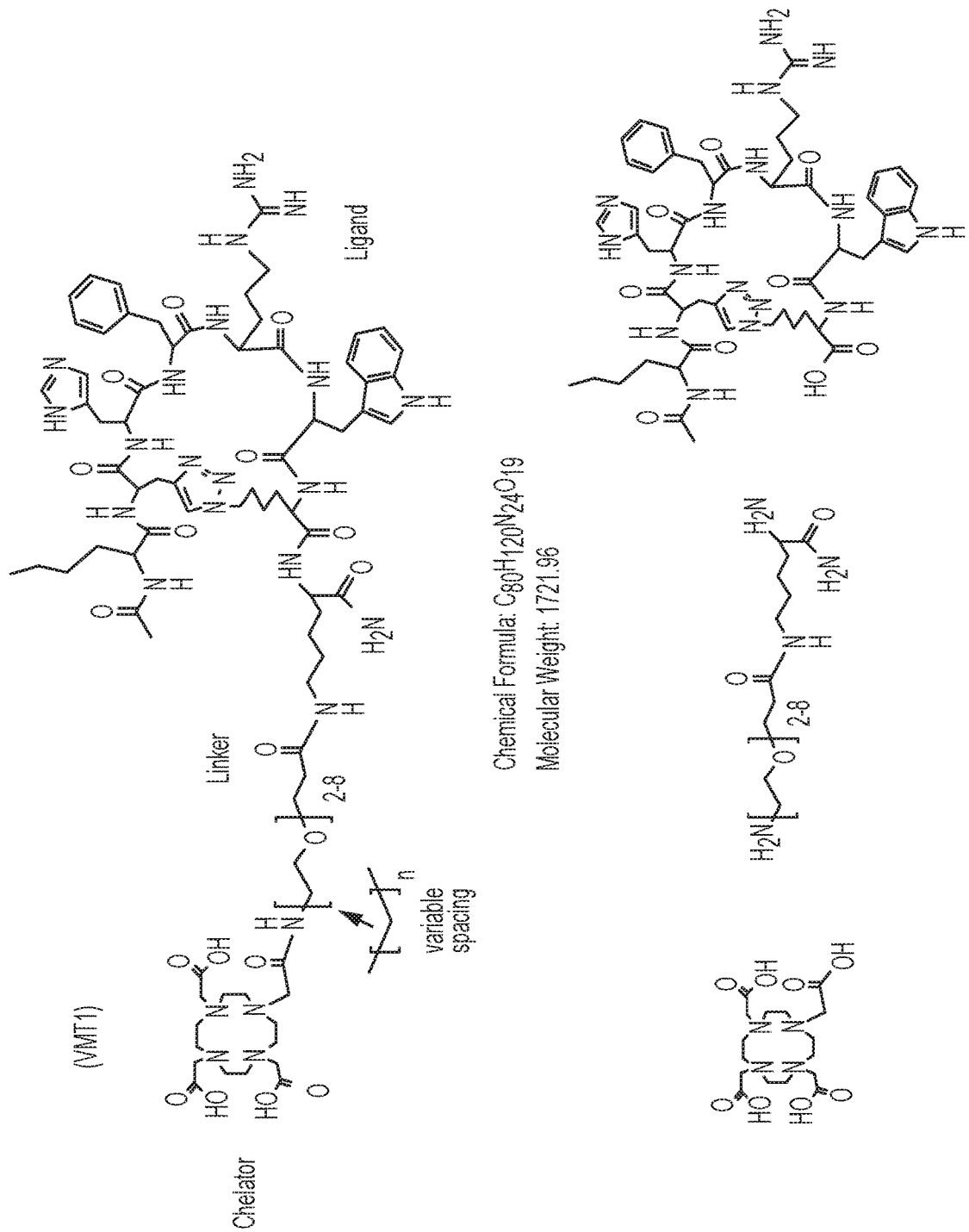
Figure 22B:
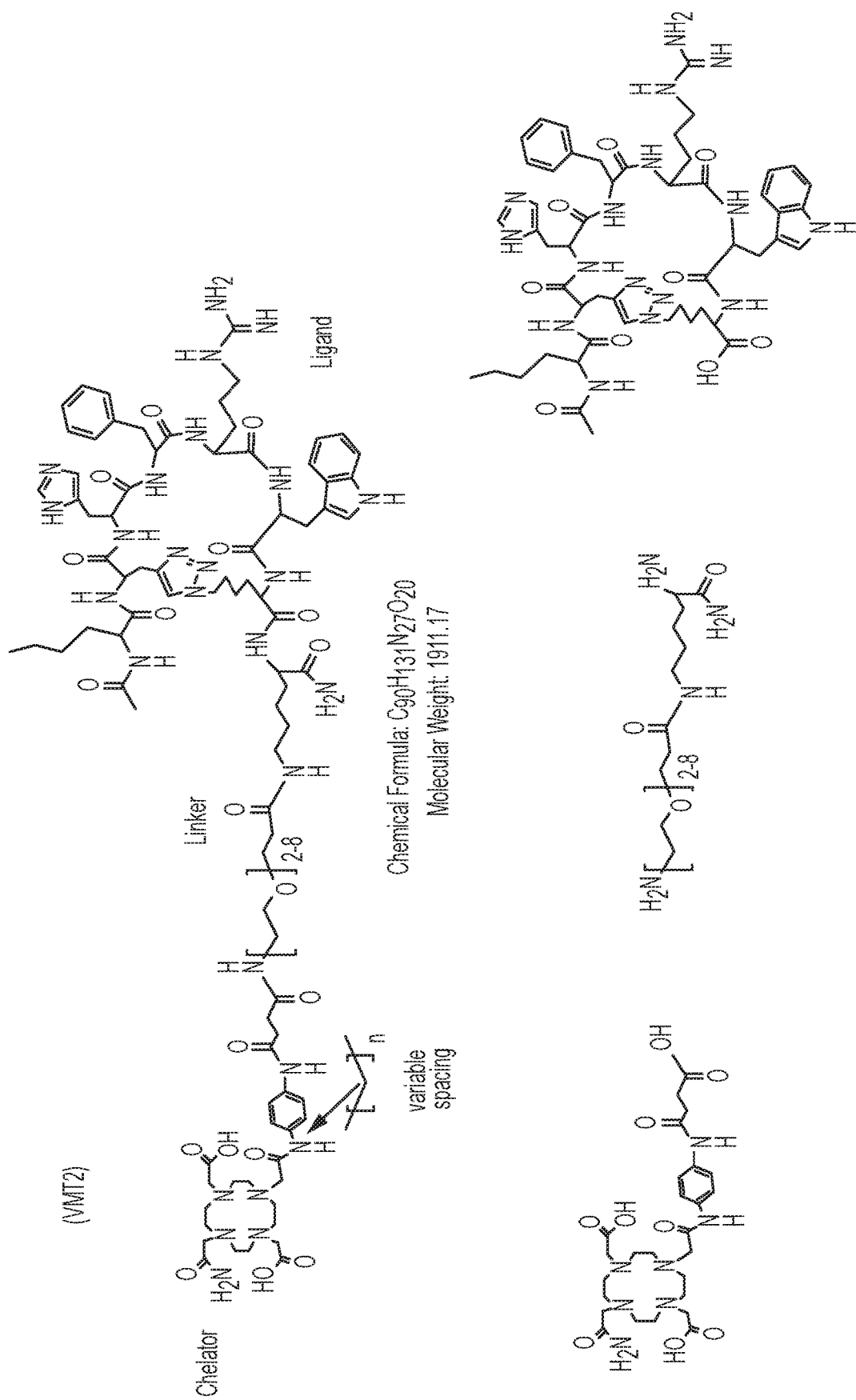
Figure 22C:
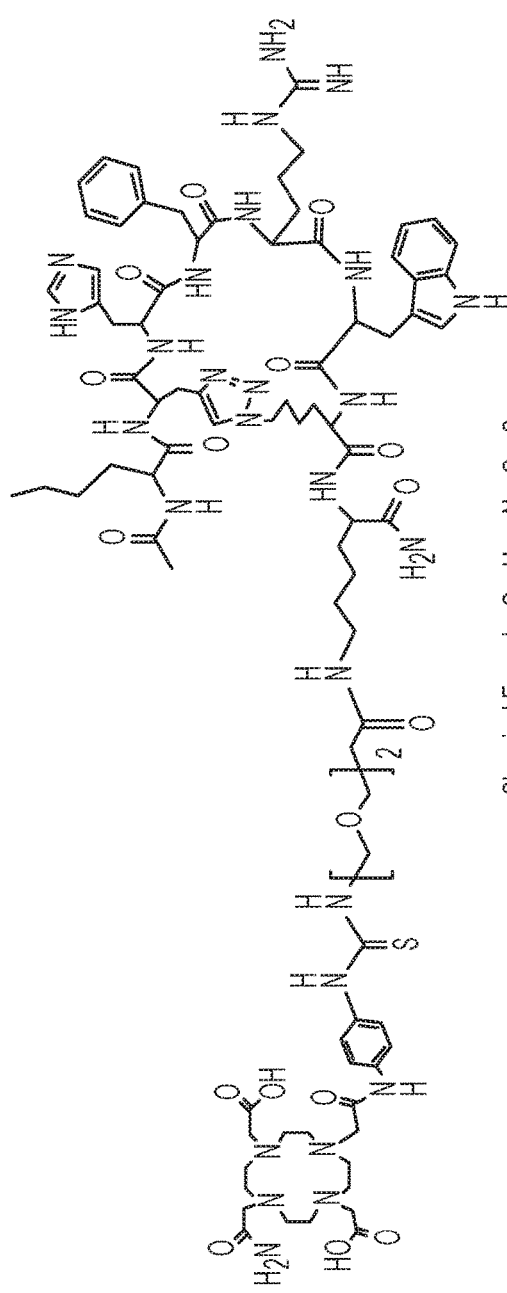
Figure 22C:
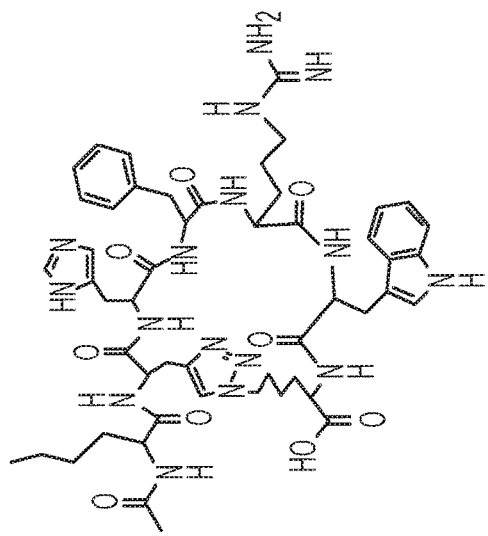
Figure 22C:
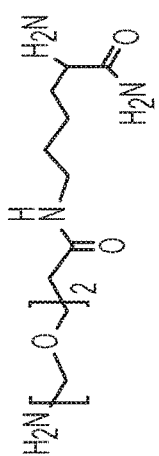
Figure 22C:
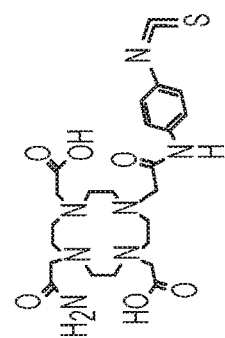

FIGS. 22A-22C. FIG. 22A provides the structure of VMT1, FIG. 22B provides the structure of VMT2, and FIG. 22C provides the structure of PSC-PEG-CLICK.

DETAILED DESCRIPTION

The melanocortin-1 receptor (MCR1) is a G-protein coupled receptor (GPCR) that belongs to melanocortin receptor family. There are five melanocortin receptors that have been isolated and cloned to date. A discussion of the melanocortin receptors is discussed in US Patent Publication 2014/0238390, which is incorporated by reference herein. MCR1 is found in a number of different cell lines and tissues, though it has only been found in high levels in melanocytic cells. MCR1 has a role in regulating skin pigmentation. MCR1 is over-expressed in most murine and human melanoma metastases.

Alpha-melanocyte stimulating hormone (α-MSH) signals via the MC1R in melanocytes to stimulate eumelanogenesis (the formation of the black pigment eumelanin) via upregulation of the enzyme tyrosinase and via melanocyte proliferation. A variety of peptides, peptide derivatives, peptidomimetics and small molecules that bind to and activate or inhibit the MCR1 have been reported.

Melanoma is a dangerous type of skin cancer that develops in cells that produce melanin (melanocytes), usually presenting as an irregular spot/mole on the skin. Causes of melanoma include UV radiation and a genetic predisposition to this type of cancer. Unlike other cancers, prevalence of melanoma is increasing, with the highest occurrence among individuals 25-29 years old. The overall lifetime risk of developing melanoma is 2.4%. In 2015, 73,870 new invasive melanomas are expected to be diagnosed, with 9,940 people expected to die of melanoma. With early treatment, survival rate is 97%.

Melanoma can migrate to other parts of the body (metastatic melanoma), and one year survival rate drastically decreases with metastasis-15-20% for Stage IV. Current types of treatment include surgery, immunotherapy (Immune checkpoint inhibitors for advanced melanoma), chemotherapy, radiation therapy, targeted therapy (target cells with gene changes) and BRAF Inhibitors. BRAF is a protein kinase of the mitogen-activated protein kinase (MAPK) pathway, and it regulates cell growth, proliferation, and differentiation. Research suggests a BRAF$^{V600E}$ mutation causes the BRAF protein (produced through the MAPK pathway) to become oncogenic. The mutation may lead to increased and uncontrolled cell proliferation, and resistance to apoptosis. The BRAF mutation is observed in about 50% of melanoma tumors. Its presence is associated with poor prognosis in metastatic melanoma.

Melanoma is the fastest growing cancer incidence in the United States. Surgery is curative for melanoma confined to the skin, but metastatic melanoma is lethal. Current FDA approved therapies for metastatic melanoma (e.g., Vemurafenib, Ipilimumab), have increased life expectancy by months, however resistance develops rapidly. The exact mechanism by which drug resistance develops is unclear; however, autophagy is known to play a major role. Autophagy is a self-degradative response of the cell towards nutrient stress. Conversely, autophagy also plays a house-keeping role by removing mis-folded or aggregated proteins and clearing damaged organelles by forming autophagosomes. Thus, autophagy is believed to play an important role in tumor progression and developing drug resistance during later stages of cancer. The Unfolded Protein Response (UPR) mediated by GRP78 ER associated protein degradation is one of the pathways that initiate autophagy in stressed cells. UPR involves the activation of three signaling pathways mediated by IRE-1, PERK and ATF6. These pathways work towards decreasing the protein load of ER by increasing the expression of molecular chaperons, activation of ERAD (ER associated protein degradation) and autophagy. However if the damage caused by the stress is extensive UPR signaling pathways initiate apoptosis. Amy S. Lee, *Cancer Res* (2007); 77:3496-3499. Emerging evidence shows that in malignant cells ER stress can be pro-survival and contribute to the development of drug resistance by initiating autophagy.

Interestingly, initial responses (tumor shrinkage) are also very common among patients treated with Vemurafenib (Zelboraf®). Vemurafenib targets a gene mutation in metastatic melanoma called BRAF-V600E, which causes metastatic melanoma cells to divide and proliferate uncontrollably and rapidly. Thus, when patients are treated with Vemurafenib, there is a generally very positive response. However, a small but lethal subpopulation of cells becomes resistant to the treatment. Thus, patients appear to be virtually cured, but the small subpopulations of cells that are resistant to treatment eventually (within months) begin to divide and proliferate rapidly and tumors regrow at precisely the same locations.

Over 80% of malignant melanomas express high levels of the melanocyte stimulating hormone (αMSH) receptor, melanocortin 1 receptor (MCR1, also called MC1R). In certain embodiments, the present therapy provides a radiolabeled peptide that binds with high affinity and specificity to MC1R and delivers radiation precisely to melanoma cells. This discovery means that the present treatment is especially effective in killing cells that have become resistant to Vemurafenib, making the combination of Vemurafenib with the current therapy an exciting new treatment for metastatic melanoma. A new combination therapy has been developed that kills vemurafenib resistant cells, but is virtually non-toxic to the rest of the body.

MCR1 Ligands

In certain embodiments, the MCR1 ligand is a targeting peptide that is an alpha-melanocyte stimulating hormone (αMSH). Alpha-MSH is a tridecapeptide (Ser-Tyr-Ser-Met-Glu-His-Phe-Arg-Trp-Gly-Lys-Pro-Val-NH$_2$) (SYS-MEHFRWGKPV) that regulates skin pigmentation in vertebrates. The core αMSH sequence, His-Phe-Arg-Trp, has been found to be sufficient for receptor recognition. α-MSH specifically recognizes melanotropin receptors. Various synthetic α-melanotropin analogs have been prepared and characterized for α-melanotropin activity. (V. J. Hruby, et al., Design, Synthesis and Conformation of Superpotent and Prolonged Acting Melanotropins (1993) *Annals of the New York Acad. of Sci.*, 680: 51-63.) They reported that cyclic analogs of α-MSH (as described by U.S. Pat. No. 4,485,039) display properties that increase their potency toward the α-MSH receptor, prolong their activity and increase their resistance to in vivo enzymatic degradation.

According to the present invention, there is provided a compound for use as a diagnostic or therapeutic pharmaceutical consisting essentially of an αMSH analog that has an integrally located a radionuclide. The radiolabeled alpha-melanotropin is administered to the patient in an amount sufficient to allow uptake and retention by the tumor cells. Examples of suitable MCR1 targeting peptides include those described in U.S. Pat. Nos. 6,338,834; 6,607,709; 6,680,045; US Patent Publication No. 20160046688; US Patent Publication No. 20150284431; US Patent Publication No. 20150119341; US Patent Publication No. 20150038434; US Patent Publication No. 20140128380; and US Patent Publication No. 20140112873, which are incorporated by reference in their entirety herein. In certain embodiments, the αMSH is linear. In certain embodiments, the αMSH is cyclic.

In one embodiment, the phrase "selectively binds" means that a compound or polypeptide made or used in the present invention preferentially binds to one type of receptor over another type of receptor when in the presence of a mixture of two or more receptors (e.g., melanocortin receptors, MC1, MC2, MC3, MC4, MC5 receptors).

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. Capitalized, single-letter abbreviations of the amino acids refer to the natural L-isomer. Lower case, single-letter abbreviations of the amino acids denotes the D-isomer.

The terms "polypeptide," "peptide," and "protein" are used interchangeably to refer to polymers of amino acids of any length. Peptides and polypeptides can be either entirely composed of synthetic, non-natural analogues of amino acids, or, is a chimeric molecule of partly natural peptide amino acids and partly non-natural analogs of amino acids. In one aspect, a polypeptide is used in a composition, cell system or process of the invention (e.g., a host cell having a plasmid expressing at least one enzyme of the invention). In addition, polypeptide can refer to compounds comprised of polymers of amino acids covalently attached to another functional group (e.g., solubilizing group, a targeting group, PEG, non-amino acid group, or other therapeutic agent).

Amino acids may be abbreviated using the following designation in parentheses: Proline (Pro), Valine (Val), Lysine (Lys), Ornithine (Orn), Norleucine (Nle), Glycine (Gly), Tryptophan (Trp), Alanine (Ala), Phenylalanine (Phe), Arginine (Arg), Histidine (His), Glutamic acid (Glu), Aspartic acid (Asp), Serine (Ser), Methionine (Met), Isoleucine (Ile), Tyrosine (Tyr), Cyclohexylalanine (Cha), 4-fluoro-D-phenylglycine (4-fluoro-D-Phg), 2-thienyl-D-alanine (D-Thi).

Polypeptide compositions of the invention can contain any combination of non-natural structural components. Individual peptide residues can be joined by peptide bonds, other chemical bonds or coupling means, such as, e.g., glutaraldehyde, N-hydroxysuccinimide esters, bifunctional maleimides, N,N-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2—for —C(=O)—NH—), aminomethylene (CH2-NH), ethylene, olefin (CH=CH), ether (CH2-O), thioether (CH2-S), tetrazole, thiazole, retroamide, thioamide, or ester (see, e.g., Spatola (1983) in Chemistry and Biochemistry of Amino Acids, Peptides and Proteins, Vol. 7, pp. 267-357, "Peptide Backbone Modifications," Marcel Dekker, N.Y., incorporated herein by reference).

Polypeptides used to practice the method of the invention can be modified by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl terminus. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1-12 (1983), incorporated herein by reference.

"Biologically active" moieties include a molecule or compound that elicits or modulates a physiological response. In one aspect, a biologically active compound stimulates melanocortin receptors, preferably MC1-receptors.

By "modulate" and "modulation" is meant that the activity of one or more proteins or protein subunits is up regulated or down regulated, such that expression, level, or activity is greater than or less than that observed in the absence of the modulator. For example, the term "modulate" can mean "inhibit" or "stimulate".

"C-terminal sequence" includes reference to the end of the amino acid chain terminated typically, but not necessarily, by a carboxyl group. The convention for writing peptide sequences is to put the C-terminal end on the right and write the sequence from N- to C-terminus. The C-terminal sequence may comprise 1 to 100 amino acids, preferably 2 to 15 amino acids, and even more preferably 3 to 10 amino acids. The C-terminal sequence may terminate with a carboxyl group or the terminus may be modified by well-known methods in the art to comprise a functional member (e.g. targeting group, retention signal, lipid, and anchor).

Imaging and Therapeutic Radionuclides

In certain embodiments, the peptide that targets MCR1 is radiolabeled for patient imaging with gallium-68, lead-203, zirconium-89, fluorine-18, technetium-99, carbon-11, indium-111, lutetium-177, copper-64, scandium-44 or other radionuclide radiometals that are suitable for imaging of disease. In certain embodiments, the radionuclide is integral in the peptide that targets MCR1.

In certain embodiments, the peptide that targets MCR1 is radiolabeled for patient therapy with lead-212, gallium-67, rhenium-188, thorium-227, actinium-225, yttrium-90, lutetium-177, actinium-225, astatine-211, radium-223, radium-224, or other radionuclide radiometals that emit a particle that is suitable for therapy of disease. In certain embodiments, the radionuclide is integral in the peptide that targets MCR1.

Isotopically-labeled peptides can generally be prepared by conventional techniques known to those skilled in the art. See, e.g., US Patent Publication No. 2014/0128380.

Chelating Agents

In certain embodiments, the chelating agent is DOTA or other chelator that is used to bind the radionuclide for diagnostic imaging or therapy for cancer or other disease.

In certain embodiments, the chelating agent is DTPA or other chelator that is used to bind the radionuclide for diagnostic imaging or therapy for cancer or other disease.

In certain embodiments, the chelator is based on S-2-(4-Nitrobenzyl)-1,4,7,10-tetraazacyclododecane or other variation on this cyclododecane.

In certain embodiments, the chelator is based on 1,4,7,10-Tetraazacyclododecane-1,4,7-tri(carbamoylmethyl)-10-acetic acid.

In certain embodiments, the chelator is based on S-2-(4-Nitrobenzyl)-1,4,7,10-tetraazacyclododecane tetraacetic acid.

In certain embodiments, the chelator is based on S-2-(4-Aminobenzyl)-1,4,7,10-tetraazacyclododecane tetraacetic acid.

In certain embodiments, the chelator is based on S-2-(4-Aminobenzyl)-1,4,7,10-tetraazacyclododecane tetra-tert-butylacetate.

In certain embodiments, the chelator is based on S-2-(4-Isothiocyanatobenzyl)-1,4,7,10-tetraazacyclododecane tetraacetic acid.

In certain embodiments, the chelator is based on 1,4,7,10-Tetraazacyclododecane-1,4,7-tris-tert-butyl acetate-10-acetic acid.

In certain embodiments, the chelator is based on 1,4,7,10-Tetraazacyclododecane-1,4,7-tris-tert-butyl acetate-10succinimidyl acetate.

In certain embodiments, the chelator is based on 1,4,7,10-Tetraazacyclododecane-1,4,7-tris-tert-butyl acetate-10-maleimidoethylacetamide.

In certain embodiments, the chelator is based on 1,4,7,10-Tetraazacyclododecane-1,4,7-tris-acetic acid-10-maleimidoethylacetamide.

In certain embodiments, the chelator is based on 1,4,7,10-Tetraazacyclododecane-1,4,7-tris-tert-butyl acetate-10-(N-a-Fmoc-N-e-acetamido-L-lysine).

In certain embodiments, the chelator is based on 1,4,7,10-Tetraazacyclododecane-1,4,7-tris(t-butyl acetate)-10-(3-butynylacetamide).

In certain embodiments, the chelator is based on 1,4,7,10-Tetraazacyclododecane-1,4,7-tris(t-butyl-acetate)-10-(aminoethylacetamide).

In certain embodiments, the chelator is based on 1,4,7,10-Tetraazacyclododecane-1,4,7-tris-tert-butyl acetate-10-(azidopropyl ethylacetamide).

In certain embodiments, the chelator is based on 1,4,7,10-Tetraazacyclododecane-1,4,7-tris(t-butyl acetate)-10-(4-aminobutyl)acetamide.

In certain embodiments, the chelator is based on 1,4,7,10-Tetraazacyclododecane-1,4,7,10-tetraacetic acid mono-N-hydroxysuccinimide ester.

In certain embodiments, the chelator is based on 1,4,7,10-Tetraazacyclododecane-1,4,7-tris(acetic acid)-10-(2-thioethyl)acetamide or other variation of DOTA.

In certain embodiments, the chelator is based on S-2-(4-Aminobenzyl)-diethylenetriamine pentaacetic acid or other variation of DTPA.

In certain embodiments, the chelator is based on 3,6,9,15-Tetraazabicyclo[9.3.1] pentadeca-1(15),11,13-triene-4-S-(4-aminobenzyl)-3,6,9-triacetic acid or other variation on this pentadeca macrocycle.

In certain embodiments, the chelator is based on 1-Oxa-4,7,10-tetraazacyclododecane-5-S-(4-aminobenzyl)-4,7,10-triacetic acid or other variation on oxo-substituted macrocycle.

In certain embodiments, the chelator is based on 2-S-(4-Isothiocyanatobenzyl)-1,4,7-triazacyclononane-1,4,7-triacetic acid or other variation on this cyclononane.

In certain embodiments, the chelator is based on 1-(4-isothiocyanatophenyl)-3-[6,17-dihydroxy-7,10,18,21-tetraoxo-27-(N-acetylhydroxylamino)-6,11,17,22-tetraazaheptaeicosine] thiourea or other variation on deferoxamine.

Linkers

In certain embodiments, L is a chemical linker that is inserted into a position between the peptide backbone that recognizes the MCR1 protein and the chelator that is used to radiolabel the composition using radionuclides for diagnostic imaging and/or therapy; and the linker improves the internalization of the composition into cells and improves the retention of the composition in tumors for more precise delivery of radiation to the cancerous tissue.

In certain embodiments, L is a hydrophobic linker consisting of an aliphatic carbon chain that connects the chelator to the peptide backbone.

In certain embodiments, L is a hydrophilic linker that includes heteroatom substitutions in the aliphatic chain that connects the chelator to the peptide backbone.

In certain embodiments, L is a mixture of hydrophilic and hydrophobic entities including piperidine insertions of amino acid insertions to lengthen the chain and modulate the pharmacodynamics properties of the composition.

In certain embodiments, L is $PEG_n$, wherein n is 1-10, such as 1, 2, 3, 4, 5, 6, 7, 8, 9, or 10. In certain embodiments, n is 2, 4 or 8 PEG subunits. In certain embodiments, n is 4.

(FIG. 9)

Figure 9:
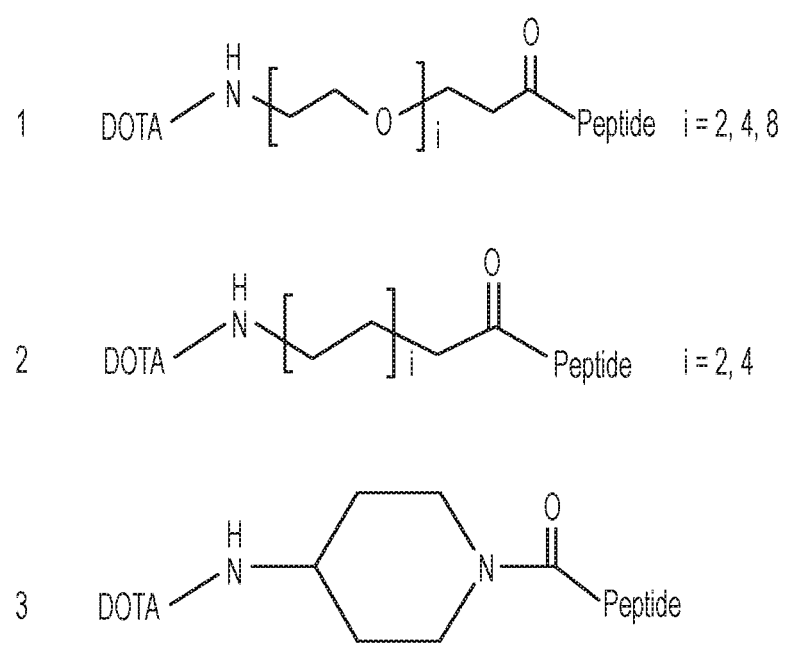
FIG. 9. Examples of linkers: (1) polyethyleneglycol (PEG)-based linkers with 2, 4, and 8 PEG subunits; (2) aliphatic (ALP) linkers of 2 and 4 carbons; and a piperidine (PIP) based linker with mixed characteristics.

In certain embodiments, L is an aliphatic (ALP) linker of 2 or 4 carbons. (FIG. 9)

In certain embodiments, L is a piperidine (PIP) based linker with mixed characteristics. (FIG. 9)

Other linkders are known in the art. See, e.g., Bandari R P, Jiang Z, Reynolds T S, Bernskoetter N E, Szczodroski A F, Bassuner K J, Kirkpatrick D L, Rold T L, Sieckman G L, Hoffman T J, Connors J P, Smith C J. Synthesis and biological evaluation of copper-64 radiolabeled [DUPA-6-Ahx-(NODAGA)-5-Ava-BBN(7-14)NH2], a novel bivalent targeting vector having affinity for two distinct biomarkers (GRPr/PSMA) of prostate cancer. Nucl Med Biol. 2014; 41(4):355-363. doi: 10.1016/j.nucmedbio.2014.01.001. PubMed PMID: 24508213; PMCID:PMC4041584; Dumont R A, Tamma M, Braun F, Borkowski S, Reubi J C, Maecke H, Weber W A, Mansi R. Targeted radiotherapy of prostate cancer with a gastrin-releasing peptide receptor antagonist is effective as monotherapy and in combination with rapamycin. J Nucl Med. 2013; 54(5):762-769. doi: 10.2967/jnumed.112.112169. PubMed PMID: 23492884; Gourni E, Mansi R, Jamous M, Waser B, Smerling C, Burian A, Buchegger F, Reubi J C, Maecke H R. N-terminal modifications improve the receptor affinity and pharmacokinetics of radiolabeled peptidic gastrin-releasing peptide receptor antagonists: examples of 68Ga- and 64Cu-labeled peptides for PET imaging. J Nucl Med. 2014; 55(10):1719-1725. doi: 10.2967/jnumed.114.141242. PubMed PMID: 25146125; Jamous M, Tamma M L, Gourni E, Waser B, Reubi J C, Maecke H R, Mansi R. PEG spacers of different length influence the biological profile of bombesin-based radiolabeled antagonists. Nucl Med Biol. 2014; 41(6):464-470. doi: 10.1016/j.nucmedbio.2014.03.014. PubMed PMID: 24780298; Mansi R, Abiraj K, Wang X, Tamma M L, Gourni E, Cescato R, Berndt S, Reubi J C, Maecke H R. Evaluation of three different families of bombesin receptor radioantagonists for targeted imaging and therapy of gastrin releasing peptide receptor (GRPR) positive tumors. J Med Chem. 2015; 58(2):682-691. doi: 10.1021/jm5012066. PubMed PMID: 25474596; Pan D, Xu Y P, Yang R H, Wang L, Chen F, Luo S, Yang M, Yan Y. A new (68)Ga-labeled BBN peptide with a hydrophilic linker for GRPR-targeted tumor imaging. Amino Acids. 2014; 46(6):1481-1489. doi: 10.1007/s00726-014-1718-y. PubMed PMID: 24633452; Stott Reynolds T J, Schehr R, Liu D, Xu J, Miao Y, Hoffman T J, Rold T L, Lewis M R, Smith C J. Characterization and evaluation of DOTA-conjugated Bombesin/RGD-antagonists for prostate cancer tumor imaging and therapy. Nucl Med Biol. 2015; 42(2):99-108. doi: 10.1016/j.nucmedbio.2014.10.002. PubMed PMID: 25459113.

Anti-Melanoma Conjugate

In certain embodiments, the present invention provides a melanoma-targeting conjugate comprising Formula I:

T-L-X wherein T is a radiolabeled MCR1 ligand,
L is a linker, and
X an anti-cancer composition,
for the therapeutic treatment of melanoma.

In certain embodiments, the MCR1 Ligand is an MCR1 Ligand as described above.

In certain embodiments, the linker is a linker as described above.

In certain embodiments, the anti-cancer composition is the chelator-modified PEG4 linked Re-cyclized MCR1 targeted peptide referred to as DOTA-PEG4-VMT-MCR1 or the PEG4-VMT-MCR1 modified to include a different chelator Agents that Increase Expression of MCR1

Vemurafenib (Zelboraf®) is a B-Raf enzyme inhibitor developed for the treatment of late-stage melanoma. Vemurafenib stops the proliferative effects of oncogenic BRAF protein. The name "vemurafenib" comes from V600E mutated BRAF inhibition.

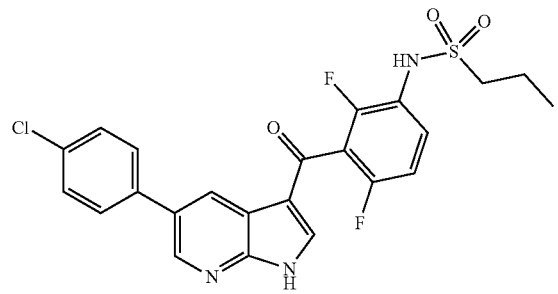 [SMILES: CCCS(=O)(=O)Nc1ccc(F)c(C(=O)c2c[nH]c3ncc(-c4ccc(Cl)cc4)cc23)c1F]

ZELBORAF® Vemurafenib is indicated for the treatment of patients with unresectable or metastatic melanoma with BRAF V600E mutation as detected by an FDA-approved test. Tumor specimens are confirmed for the presence of BRAF V600E mutation prior to initiation of treatment with Vemurafenib. The recommended dose is 960 mg orally twice daily taken approximately 12 hours apart with or without a meal; 720 mg twice daily for first appearance of intolerable Grade 2 or Grade 3 adverse reactions; or 480 mg twice daily for second appearance of Grade 2 (if intolerable) or Grade 3 adverse reactions or for first appearance of Grade 4 adverse reaction (if clinically appropriate). Unfortunately, metastatic melanoma can resist vemurafenib treatment. Vemurafenib slows tumor progression for only about 5.3 months. As a result, finding an effective treatment for metastatic melanoma is challenging.

The term "anti-cancer agent" includes a Triphenylphosphonium (TPP) agent or derivative thereof that increases reactive oxygen species (ROS) levels in cancer cell mitochondria, and a pharmaceutically acceptable diluent or carrier. As used herein, the term triphenylphosphonium (TPP) is any molecule containing a triphenylphosphine cation ($^+$PPh$_3$) moiety. See, e.g., WO 2013/019975 and WO 2014/124384, which are incorporated by reference herein.

TPP salts can be reacted with alcohols, alkyl halides, and carboxylic acids, which allow them to be used as starting materials for the synthesis of a large variety of chemical derivatives, e.g., XTPP agents. Charged molecules generally cannot pass through cell membranes without the assistance of transporter proteins because of the large activation energies need to remove of associated water molecules. In the TPP molecules, however, the charge is distributed across the large lipophilic portion of the phosphonium ion, which significantly lowers this energy requirement, and allows the TPP to pass through lipid membranes. The phosphonium salts accumulate in mitochondria due to the relatively highly negative potential inside the mitochondrial matrix. The compositions of the present invention utilize XTPP agents that have activity in treating cancer cells, in that the XTPP agents preferentially localize to cancer cells, as compared to the comparable normal cells because cancer cells are often characterized by abnormal mitochondrial oxidative metabolism (Aykin-Burns N, Ahmad I M, Zhu Y, Oberley L W, and Spitz D R: Increased levels of superoxide and hydrogen peroxide mediate the differential susceptibility of cancer cells vs. normal cells to glucose deprivation. Biochem. J. 2009; 418:29-37. PMID: 189376440) and altered mitochondrial membrane potential (Chen LB: Mitochondrial membrane potential in living cells, Ann. Rev. Cell Biol. 1988; 4:155-81), relative to normal cells.

In certain embodiments, the TTP agent is 10-TTP or 12-TTP.

In certain embodiments, the TTP agent is a compound of formula I:

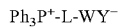    I wherein:
W is selected from:

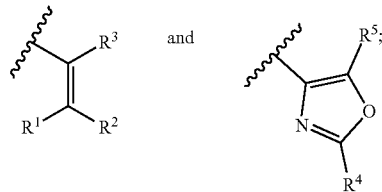

L is absent, $(C_1-C_{12})$alkyl, $(C_1-C_{12})$alkylene, -$(CH_2CH_2O)_n$M-, —C(=O)$NR^{L1}$-, —$NR^{L1}$C(=O)— or —$NR^{L1}$C(=S)$NR^{L1}$—;
n is 1 to 12;
M is absent or —$CH_2CH_2$-;
$R^{L1}$ is H or $(C_1-C_6)$alkyl;
$R^1$ is halo or —NHC(=O)$R_a$;
$R^2$ is halo, $SR_b$ or —C(=O)$NHR_c$;
$R^3$ is —NH(C=O)$R_d$, —NH(C=O)$NHR_d$ or phenyl wherein any phenyl of $R^3$ is optionally substituted with one or more halo, $(C_1-C_3)$alkyl, $(C_1-C_3)$haloalkyl, O$(C_1-C_3)$ haloalkyl or —O$(C_1-C_3)$alkyl;
$R^4$ is $(C_1-C_6)$alkyl or phenyl wherein any phenyl of $R^4$ is optionally substituted with one or more halo, $(C_1-C_3)$alkyl, $(C_1-C_3)$haloalkyl or —O$(C_1-C_3)$alkyl;
$R^5$ is —S$(C_1-C_6)$alkyl or —N$((C_1-C_6)$alkyl$)_2$;
$R_a$ is phenyl optionally substituted with one or more halo, $(C_1-C_3)$alkyl, $(C_1-C_3)$haloalkyl or —O$(C_1-C_3)$alkyl;
$R_b$ is phenyl optionally substituted with one or more halo, $(C_1-C_3)$alkyl, $(C_1-C_3)$haloalkyl or —O$(C_1-C_3)$alkyl;
$R_c$ is phenyl optionally substituted with one or more halo, $(C_1-C_3)$alkyl, $(C_1-C_3)$haloalkyl or —O$(C_1-C_3)$alkyl;
$R_d$ is phenyl optionally substituted with one or more halo, $(C_1-C_3)$alkyl, $(C_1-C_3)$haloalkyl or —O$(C_1-C_3)$alkyl; and
Y is a counterion;
or a pharmaceutically acceptable salt thereof, and a pharmaceutically acceptable diluent or carrier.

In certain embodiments, the anti-cancer agent is ipilimumab.

The term "anti-cancer agent" includes BUPHENYL® (sodium phenylbutyrate, PBA). PBA is formulated as tablets for oral administration and as a powder for oral, nasogastric, or gastrostomy tube administration contain sodium phenylbutyrate. Sodium phenylbutyrate is an off-white crystalline substance which is soluble in water and has a strong salty taste. Sodium phenylbutyrate also is freely soluble in methanol and practically insoluble in acetone and diethyl ether. It is known chemically as 4-phenylbutyric acid, sodium salt with a molecular weight of 186 and the molecular formula C10H$_{11}$O$_2$Na.

PBA has the following structure:

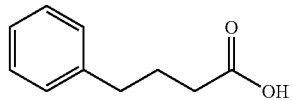 [SMILES: O=C(O)CCCc1ccccc1]

In certain embodiments, Phenylbutyrate is Buphenyl® (sodium phenylbutyrate). Sodium phenylbutyrate is used for chronic management of urea cycle disorders (UCDs). Its mechanism of action involves the quick metabolization of sodium phenylbutyrate to phenylacetate. Phenylacetate then conjugates with glutamine (via acetylation) to form phenylacetylglutamine, and phenylacetylglutamine is excreted by the kidneys. It has been observed that sodium phenylbutyrate reduces Endoplasmic Reticulum (ER) stress.

The cellular response to ER stress is neither fully oncogenic nor completely tumor suppressive. It involves complex signaling with many pathways. The relative importance of each pathway varies between cells depending on chronicity of ER stress, and on relative expression of various associated proteins. As solid cancers grow, nutrients and oxygen required exceed capacity of existing vascular bed, which can trigger angiogenesis (development of new blood vessels) to get more oxygen/nutrients to the cancers. Cancers, however, usually become hypoxic and nutrient-depleted, and with the hypoxia leading to impaired generation of ATP. The low ATP levels compromise ER protein folding which leads to ER stress. Thus, unfolded, and/or misfolded proteins are associated with ER stress and cancer cells exist with higher levels of ER stress relative to health cells.

Potential outcomes as a consequence of ER stress include high rates of protein synthesis that would trigger increased expression of autophagy, which is cytoprotective during stress (liberates amino acids, and removes damaged organelles). Another outcome would be an increased tolerance to hypoxia, which would promote tumor growth. This would also increase autophagy, promoting drug resistance. Thus, a successful treatment would inhibit autophagy and promote cell death.

Sodium phenylbutyrate decreases ER Stress. Lowering ER stress prevents tolerance to hypoxia, and prevents cytoprotective autophagy (which leads to drug resistance). Phenylbutyrate acts as a "chemical chaperone," meaning it guides proper protein folding, and the presence of properly folded proteins lowers ER stress.

PBA and other histone deacetylase inhibitors (e.g., Vorinastat) upregulate MCR1 expression in metastatic melanoma cells. PBA has a second mechanism of action for the present combination therapy in that it disrupts ER-stress mediated autophagy, which is an underlying mechanism of metastatic melanoma resistance to vemurafenib and MAPK pathway inhibitor treatments. Thus, PBA sensitizes BRAF inhibitor resistant melanoma cells to BRAF inhibition treatment.

Anti-Cancer Agents

As used herein, the term "anti-cancer agent" includes therapeutic agents that kill cancer cells; slow tumor growth and cancer cell proliferation; and ameliorate or prevent one or more of the symptoms of cancer. An anti-cancer agent includes pharmaceutically acceptable salts. The term "pharmaceutically acceptable salts" refers to salts that retain the desired biological activity of the above-identified compounds, and include pharmaceutically acceptable acid addition salts and base addition salts. Suitable pharmaceutically acceptable acid addition salts may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

In certain embodiments, the anti-cancer agent is a MAPK pathway inhibitor, including but not limited to cobimetinib, dabrafenib, and/or trametinib.

Skin Abnormalities and Cancers

In certain embodiments, the skin abnormality, disease and/or condition includes, but is not limited to, hyperpigmentation (including melasma), hypopigmentation (including vitiligo), melanoma, metastatic melanoma, basal cell carcinoma, squamous cell carcinoma, erythropoietic protoporphyria, polymorphous light eruption, solar urticaria, photosensitivity, sunburn, inflammatory diseases, aberrant fibroblast activity and pain.

In certain embodiments, the skin abnormality is a skin cancer. In certain embodiments, the skin cancer is melanoma. In cerain embodiments, the melanoma is metastatic melanoma. In cerain embodiments, the melanoma is drug-resistant (e.g., vemurafenib-resistant) metastatic melanoma.

Agents that Increase Expression of MCR1

Vemurafenib (Zelboraf®) is a B-Raf enzyme inhibitor developed for the treatment of late-stage melanoma. Vemurafenib stops the proliferative effects of oncogenic BRAF protein. The name "vemurafenib" comes from V600E mutated BRAF inhibition.

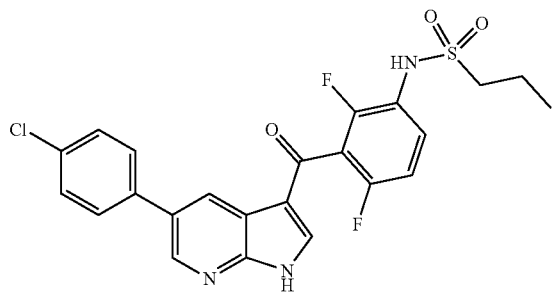 [SMILES: CCCS(=O)(=O)Nc1ccc(F)c(C(=O)c2c[nH]c3ncc(-c4ccc(Cl)cc4)cc23)c1F]

ZELBORAF® Vemurafenib is indicated for the treatment of patients with unresectable or metastatic melanoma with BRAF V600E mutation as detected by an FDA-approved test. Tumor specimens are confirmed for the presence of BRAF V600E mutation prior to initiation of treatment with Vemurafenib. The recommended dose is 960 mg orally twice daily taken approximately 12 hours apart with or without a meal; 720 mg twice daily for first appearance of intolerable Grade 2 or Grade 3 adverse reactions; or 480 mg twice daily for second appearance of Grade 2 (if intolerable) or Grade 3 adverse reactions or for first appearance of Grade 4 adverse reaction (if clinically appropriate). Unfortunately, metastatic melanoma can resist vemurafenib treatment. Vemurafenib slows tumor progression for only about 5.3 months. As a result, finding an effective treatment for metastatic melanoma is challenging.

The term "anti-cancer agent" includes a Triphenylphosphonium (TPP) agent or derivative thereof that increases reactive oxygen species (ROS) levels in cancer cell mitochondria, and a pharmaceutically acceptable diluent or carrier. As used herein, the term triphenylphosphonium (TPP) is any molecule containing a triphenylphosphine cation ($^+$PPh$_3$) moiety. See, e.g., WO 2013/019975 and WO 2014/124384, which are incorporated by reference herein.

TPP salts can be reacted with alcohols, alkyl halides, and carboxylic acids, which allow them to be used as starting materials for the synthesis of a large variety of chemical derivatives, e.g., XTPP agents. Charged molecules generally cannot pass through cell membranes without the assistance of transporter proteins because of the large activation energies need to remove of associated water molecules. In the TPP molecules, however, the charge is distributed across the large lipophilic portion of the phosphonium ion, which significantly lowers this energy requirement, and allows the TPP to pass through lipid membranes. The phosphonium salts accumulate in mitochondria due to the relatively highly negative potential inside the mitochondrial matrix. The compositions of the present invention utilize XTPP agents that have activity in treating cancer cells, in that the XTPP agents preferentially localize to cancer cells, as compared to the comparable normal cells because cancer cells are often characterized by abnormal mitochondrial oxidative metabolism (Aykin-Burns N, Ahmad I M, Zhu Y, Oberley L W, and Spitz D R: Increased levels of superoxide and hydrogen peroxide mediate the differential susceptibility of cancer cells vs. normal cells to glucose deprivation. Biochem. J. 2009; 418:29-37. PMID: 189376440) and altered mitochondrial membrane potential (Chen L B: Mitochondrial membrane potential in living cells, Ann. Rev. Cell Biol. 1988; 4:155-81), relative to normal cells.

In certain embodiments, the TTP agent is 10-TTP or 12-TTP.

In certain embodiments, the TTP agent is a compound of formula I:

$$Ph_3P^+\text{-L-W} \quad Y^- \qquad \qquad I$$

wherein:
W is selected from:

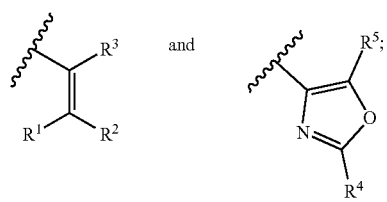

L is absent, $(C_1-C_{12})$alkyl, $(C_1-C_{12})$alkylene, —(CH$_2$CH$_2$O)$_n$M-, —C(=O)NR$^{L1}$-, —NR$^{L1}$C(=O)— or —NR$^{L1}$C(=S)NR$^{L1}$;
n is 1 to 12;
M is absent or —CH$_2$CH$_2$-;
R$^{L1}$ is H or $(C_1-C_6)$alkyl;
R$^1$ is halo or —NHC(=O)R$_a$;
R$^2$ is halo, SR$_b$ or —C(=O)NHR$_c$;
R$^3$ is —NH(C=O)R$_d$, —NH(C=O)NHR$_d$ or phenyl wherein any phenyl of R$^3$ is optionally substituted with one or more halo, $(C_1-C_3)$alkyl, $(C_1-C_3)$haloalkyl, $O(C_1-C_3)$haloalkyl or $-O(C_1-C_3)$alkyl;

$R^4$ is $(C_1-C_6)$alkyl or phenyl wherein any phenyl of $R^4$ is optionally substituted with one or more halo, $(C_1-C_3)$alkyl, $(C_1-C_3)$haloalkyl or $-O(C_1-C_3)$alkyl;

$R^5$ is $-S(C_1-C_6)$alkyl or $-N((C_1-C_6)$alkyl$)_2$;

$R_a$ is phenyl optionally substituted with one or more halo, $(C_1-C_3)$alkyl, $(C_1-C_3)$haloalkyl or $-O(C_1-C_3)$alkyl;

$R_b$ is phenyl optionally substituted with one or more halo, $(C_1-C_3)$alkyl, $(C_1-C_3)$haloalkyl or $-O(C_1-C_3)$alkyl;

$R_c$ is phenyl optionally substituted with one or more halo, $(C_1-C_3)$alkyl, $(C_1-C_3)$haloalkyl or $-O(C_1-C_3)$alkyl;

$R_d$ is phenyl optionally substituted with one or more halo, $(C_1-C_3)$alkyl, $(C_1-C_3)$haloalkyl or $-O(C_1-C_3)$alkyl; and Y is a counterion;

or a pharmaceutically acceptable salt thereof, and a pharmaceutically acceptable diluent or carrier.

In certain embodiments, the anti-cancer agent is ipilimumab.

The term "anti-cancer agent" includes BUPHENYL® (sodium phenylbutyrate, PBA). PBA is formulated as tablets for oral administration and as a powder for oral, nasogastric, or gastrostomy tube administration contain sodium phenylbutyrate. Sodium phenylbutyrate is an off-white crystalline substance which is soluble in water and has a strong salty taste. Sodium phenylbutyrate also is freely soluble in methanol and practically insoluble in acetone and diethyl ether. It is known chemically as 4-phenylbutyric acid, sodium salt with a molecular weight of 186 and the molecular formula $C10H_{11}O_2Na$.

PBA has the following structure:

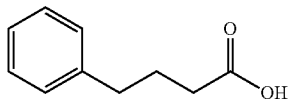 [SMILES: O=C(O)CCCc1ccccc1]

In certain embodiments, Phenylbutyrate is Buphenyl® (sodium phenylbutyrate). Sodium phenylbutyrate is used for chronic management of urea cycle disorders (UCDs). Its mechanism of action involves the quick metabolization of sodium phenylbutyrate to phenylacetate. Phenylacetate then conjugates with glutamine (via acetylation) to form phenylacetylglutamine, and phenylacetylglutamine is excreted by the kidneys. It has been observed that sodium phenylbutyrate reduces Endoplasmic Reticulum (ER) stress.

The cellular response to ER stress is neither fully oncogenic nor completely tumor suppressive. It involves complex signaling with many pathways. The relative importance of each pathway varies between cells depending on chronicity of ER stress, and on relative expression of various associated proteins. As solid cancers grow, nutrients and oxygen required exceed capacity of existing vascular bed, which can trigger angiogenesis (development of new blood vessels) to get more oxygen/nutrients to the cancers. Cancers, however, usually become hypoxic and nutrient-depleted, and with the hypoxia leading to impaired generation of ATP. The low ATP levels compromise ER protein folding which leads to ER stress. Thus, unfolded, and/or misfolded proteins are associated with ER stress and cancer cells exist with higher levels of ER stress relative to health cells.

Potential outcomes as a consequence of ER stress include high rates of protein synthesis that would trigger increased expression of autophagy, which is cytoprotective during stress (liberates amino acids, and removes damaged organelles). Another outcome would be an increased tolerance to hypoxia, which would promote tumor growth. This would also increase autophagy, promoting drug resistance. Thus, a successful treatment would inhibit autophagy and promote cell death.

Sodium phenylbutyrate decreases ER Stress. Lowering ER stress prevents tolerance to hypoxia, and prevents cytoprotective autophagy (which leads to drug resistance). Phenylbutyrate acts as a "chemical chaperone," meaning it guides proper protein folding, and the presence of properly folded proteins lowers ER stress.

PBA and other histone deacetylase inhibitors (e.g., Vorinastat) upregulate MCR1 expression in metastatic melanoma cells. PBA has a second mechanism of action for the present combination therapy in that it disrupts ER-stress mediated autophagy, which is an underlying mechanism of metastatic melanoma resistance to vemurafenib and MAPK pathway inhibitor treatments. Thus, PBA sensitizes BRAF inhibitor resistant melanoma cells to BRAF inhibition treatment.

Compositions and Methods of Administration

The present invention provides a method for increasing the anticancer effects of a conventional cancer therapy (i.e., radio- and/or chemo-therapy) on cancerous cells in a mammal, comprising contacting the cancerous cell with an effective amount of a melanoma-targeting conjugate comprising Formula I:

T-L-X wherein T is a MCR1 Ligand,

L is a linker, and

X an anti-cancer composition, for the therapeutic treatment of melanoma.

In certain embodiments, the conjugate is administered along with an additional conventional cancer therapy modality. In certain embodiments, the additional cancer therapy is chemotherapy and/or radiation. In certain embodiments, the conjugate of Formula I and anti-cancer agent are administered sequentially to a mammal rather than in a single composition. In certain embodiments, the mammal is a human.

The present invention provides a method for increasing the anticancer effects of a conventional cancer therapy (i.e., radio- and/or chemo-therapy) on cancerous cells in a mammal, comprising contacting the cancerous cell with an effective amount of an agent that increases expression of MCR1 and with an MCR1 ligand.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The present invention provides a "substantially pure compound". The term "substantially pure compound" is used herein to describe a molecule, such as a polypeptide (e.g., a polypeptide that binds MC1R, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

"Treatment", "treating", "treat" or "therapy" as used herein refers to administering, to a mammal, agents that are capable of eliciting a prophylactic, curative or other beneficial effect in the individual. Treatment may additionally result in attenuating or ameliorating a disease or symptoms of a disease in a subject.

In certain embodiments, the conjugate is administered along with an additional conventional cancer therapy modality. In certain embodiments, the additional cancer therapy is chemotherapy and/or radiation. In certain embodiments, the agent that increases expression of MCR1 and an MCR1 ligand are administered sequentially to a mammal rather than in a single composition. In certain embodiments, the mammal is a human.

In certain embodiments of the methods described above, agent that increases expression of MCR1 does not significantly inhibit viability of comparable non-cancerous cells.

In certain embodiments of the methods described above, the tumor is reduced in volume by at least 10%. In certain embodiments, the tumor is reduced by any amount between 1-100%. In certain embodiments, the tumor uptake of molecular imaging agents, such as fluorine-18 deoxyglucose, fluorine-18 thymidine or other suitable molecular imaging agent, is reduced by any amount between 1-100%. In certain embodiments the imaging agent is fluorine-18 deoxyglucose, fluorine-18 thymidine or other suitable molecular imaging agent. In certain embodiments, the mammal's symptoms (such as flushing, nausea, fever, or other maladies associated with cancerous disease) are alleviated.

Administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, a-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The agent that increases expression of MCR1 and the MCR1 ligand can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The dosage of the agent that increases expression of MCR1 and the MCR1 ligand varies depending on age, weight, and condition of the subject. Treatment may be initiated with small dosages containing less than optimal doses, and increased until a desired, or even an optimal effect under the circumstances, is reached. In general, the dosage is about 450-600 mg/kg/day in patients weighing less than 20 kg, or 9.9-13.0 $g/m^2$/day in larger patients. Higher or lower doses, however, are also contemplated and are, therefore, within the confines of this invention. A medical practitioner may prescribe a small dose and observe the effect on the subject's symptoms. Thereafter, he/she may increase the dose if suitable. In general, agent that increases expression of MCR1 and the MCR1 ligand are administered at a concentration that affords effective results without causing any unduly harmful or deleterious side effects, and may be administered either as a single unit dose, or if desired in convenient subunits administered at suitable times.

A pharmaceutical composition of the invention is formulated to be compatible with its intended route of administration. For example, the therapeutic agent may be introduced directly into the cancer of interest via direct injection. Additionally, examples of routes of administration include oral, parenteral, e.g., intravenous, slow infusion, intradermal, subcutaneous, oral (e.g., ingestion or inhalation), transdermal (topical), transmucosal, and rectal administration. Such compositions typically comprise the agent that increases expression of MCR1 and the MCR1 ligand and a pharmaceutically acceptable carrier. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration, and a dietary food-based form. The use of such media and agents for pharmaceutically active substances is well known in the art and food as a vehicle for administration is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose, or can be formulated in multiple dosage units. Treatment may require a one-time dose, or may require repeated doses.

"Systemic delivery," as used herein, refers to delivery of an agent or composition that leads to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent directly to a target site within an organism. For example, an agent can be locally delivered by direct injection into a disease site, other target site, or a target organ such as the skin.

The term "mammal" refers to any mammalian species such as a human, mouse, rat, dog, cat, hamster, guinea pig, rabbit, livestock, and the like.

The terms "treat" and "treatment" refer to both therapeutic treatment and prophylactic or preventative measures, wherein the object is to prevent or decrease an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The invention will now be illustrated by the following non-limiting Examples.

Example 1

Figure 1:
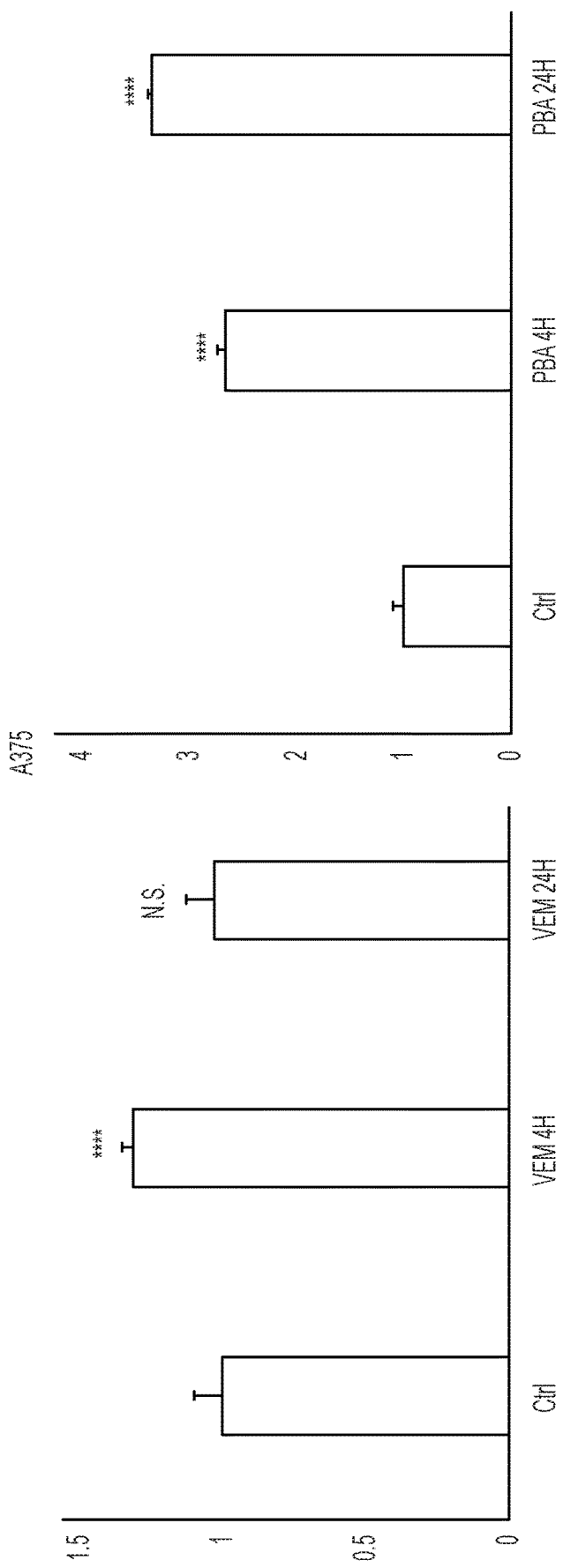
FIG. 1: Flowcytometry analysis of MCR1 expression in A375 malignant melanoma cells. A375 cells were treated with either 2 μmole Vemrafenib or 3 mmole 4-PBA for 4h and 24h (n=3). The treated and untreated (control) cells were stained with anti-MC1R-phycoerythrin (PE) monoclonal antibody conjugate. Fluorescence intensity was corrected by auto-fluorescence of cells without staining and data were expressed as relative (vs control) fluorescence intensity±SD. Statistical significance was determined by Student's T-test ($*P<0.05$; $P<0.01$; $*P<0.001$; $****P<0.0001$).
Figure 2:
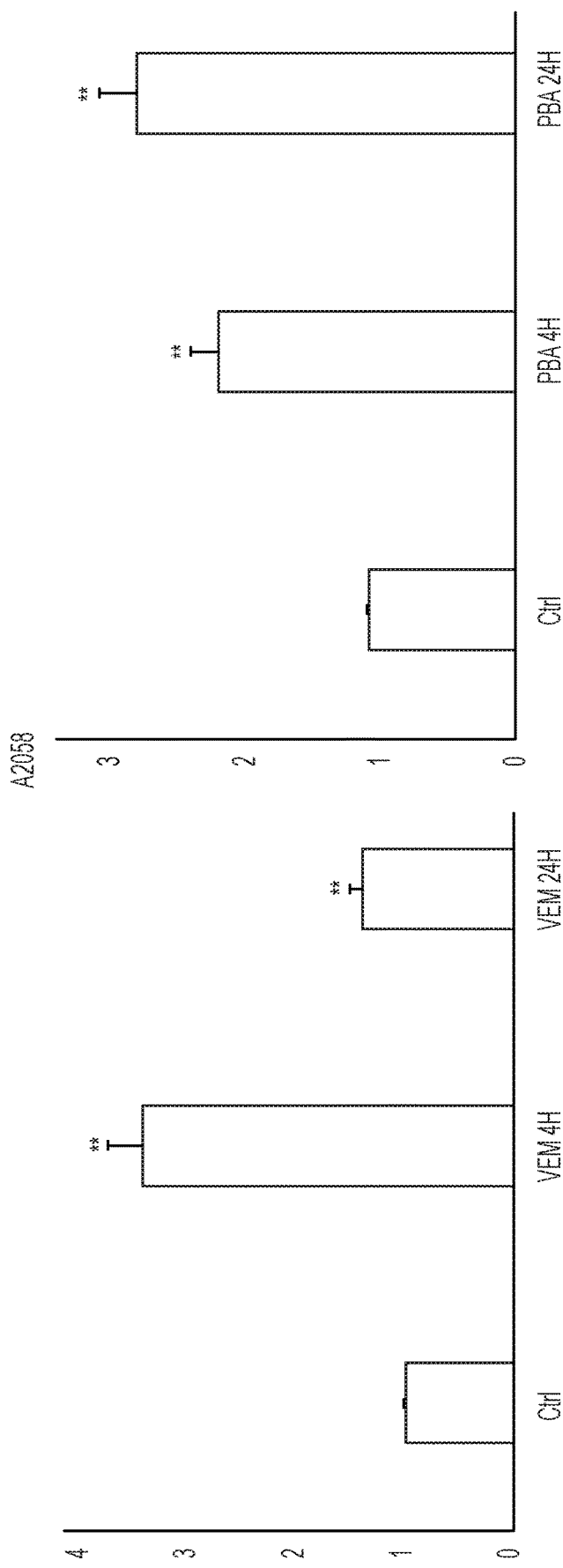
FIG. 2: Flowcytometry analysis of MCR1 expression in A2058 malignant melanoma cells. A2058 cells were treated with either 2 μmole Vemrafenib or 3 mmole 4-PBA for 4h and 24h (n=3). The treated and untreated (control) cells were stained with anti-MC1R-phycoerythrin (PE) monoclonal antibody conjugate. Fluorescence intensity was corrected by auto-fluorescence of cells without staining and data were expressed as relative (vs control) fluorescence intensity±SD. Statistical significance was determined by Student's T-test ($*P<0.05$; $P<0.01$; $*P<0.001$; $****P<0.0001$).
Figure 3:
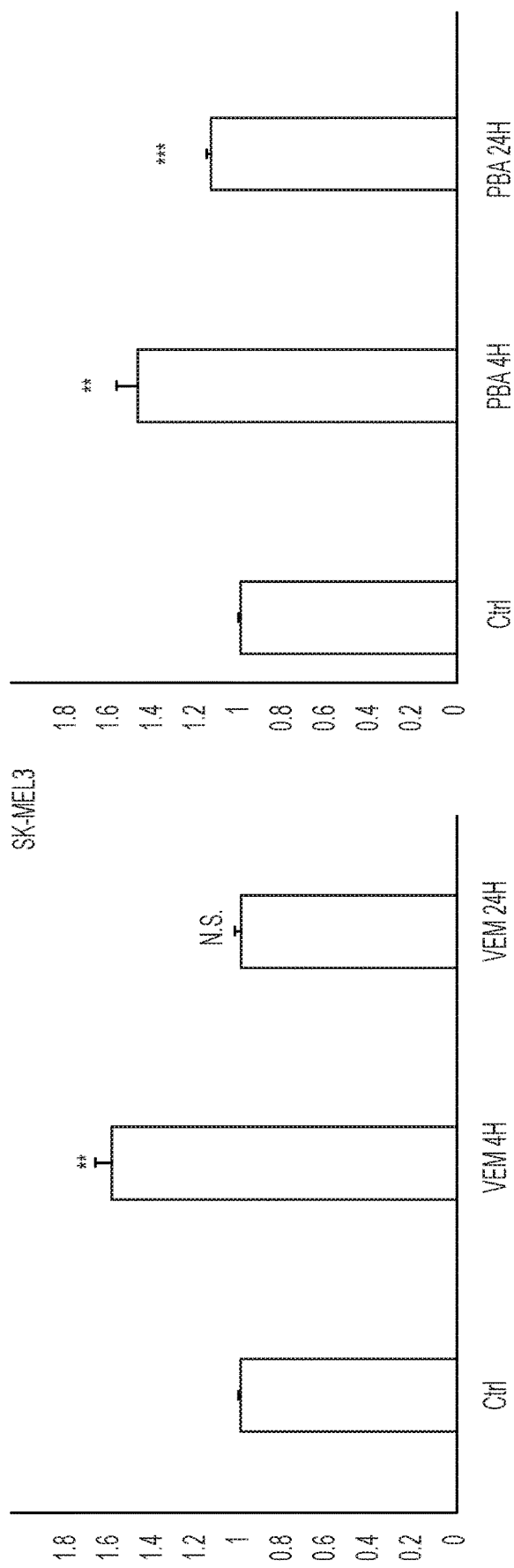
FIG. 3: Flowcytometry analysis of MCR1 expression in SK-Mel3 malignant melanoma cells. SK-Mel3 cells were treated with either 2 μmole Vemrafenib or 3 mmole 4-PBA for 4h and 24h (n=3). The treated and untreated (control) cells were stained with anti-MC1R-phycoerythrin (PE) monoclonal antibody conjugate. Fluorescence intensity was corrected by auto-fluorescence of cells without staining and data were expressed as relative (vs control) fluorescence intensity±SD. Statistical significance was determined by Student's T-test ($*P<0.05$; $P<0.01$; $*P<0.001$; $****P<0.0001$, N.S. non-significant).

Experiments were performed showing that it is possible to up-regulate the MCR1 receptor expression pharmacologically (FIGS. 1-3). Cells were treated with clinically relevant concentrations of agents and analyzed by flow cytometry for expression of the MCR1 protein.

Example 2

Figure 4:
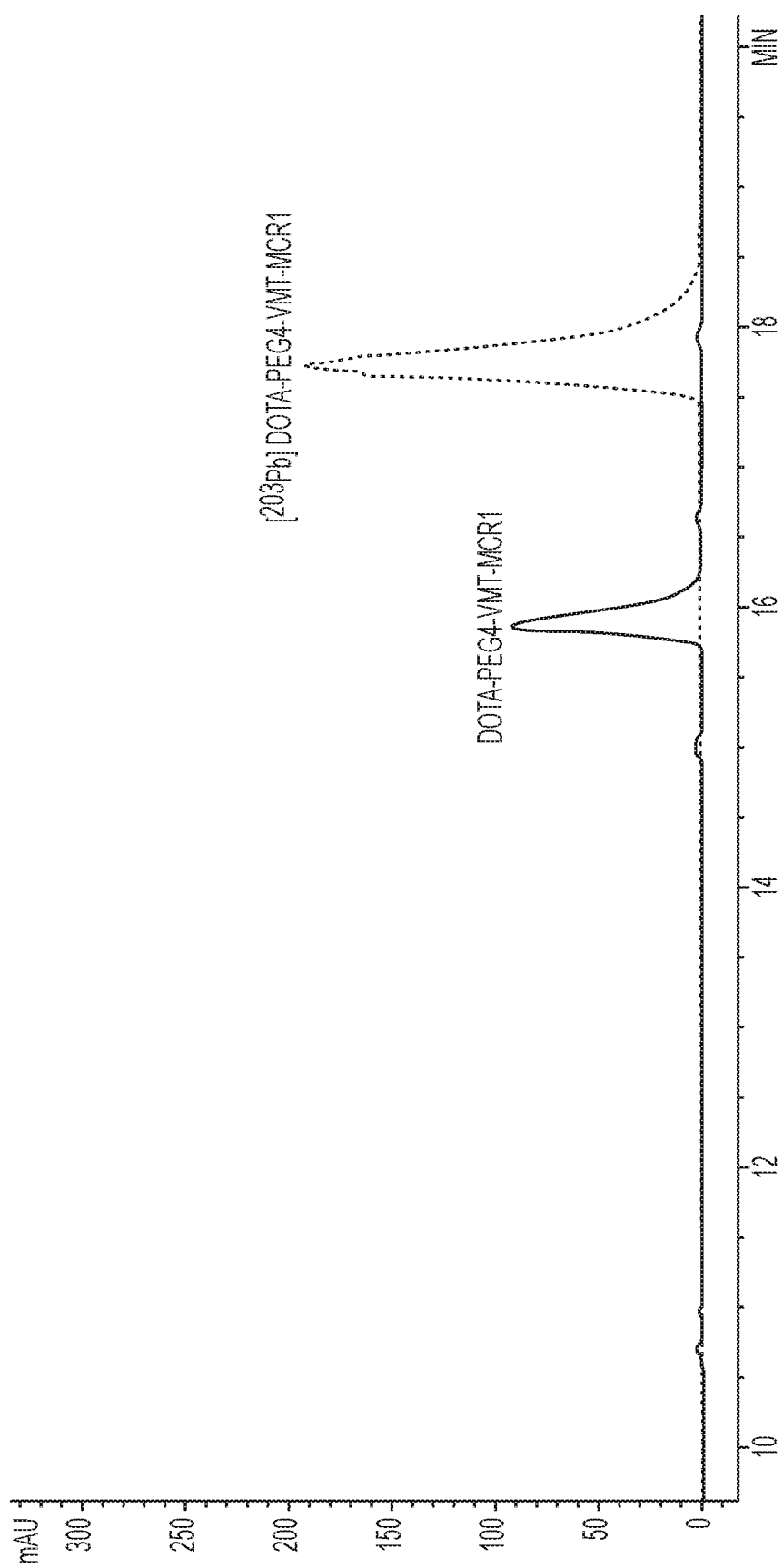
FIG. 4: Typical radio-HPLC chromatogram of co-injection of DOTA-PEG4-VMT-MCR1 and [$^{203}$Pb]DOTA-PEG4-VMT-MCR1. (VMT=Viewpoint Molecular Targeting)

Experiments were performed showing that the internalization of linker modified variants were superior to conjugates lacking linkers. A typical radio-HPLC chromatogram of co-injection of DOTA-PEG4-VMT-MCR1 and [$^{203}$Pb] DOTA-PEG4-VMT-MCR1 is shown in FIG. 4. [$^{203}$Pb] DOTA-PEG4-VMT-MCR1 was radiolabeled by standard Pb-resin based method. An aliquot of 37kBq [$^{203}$Pb]DOTA-PEG4-VMT-MCR1 was mixed with 10 μg of DOTA-PEG4-VMT-MCR1 before injection. The retention time of both content were monitored by UV signal at 280 nm and β-RAM radio-detector; Gradient: linear 16%-26% of acetonitrile in 20 mM HCl over 20 minutes on Vyldac 218TP $C_{18}$ column (4.6×150 mm 5 μm) with 1 ml/min flow rate.

Figure 5:
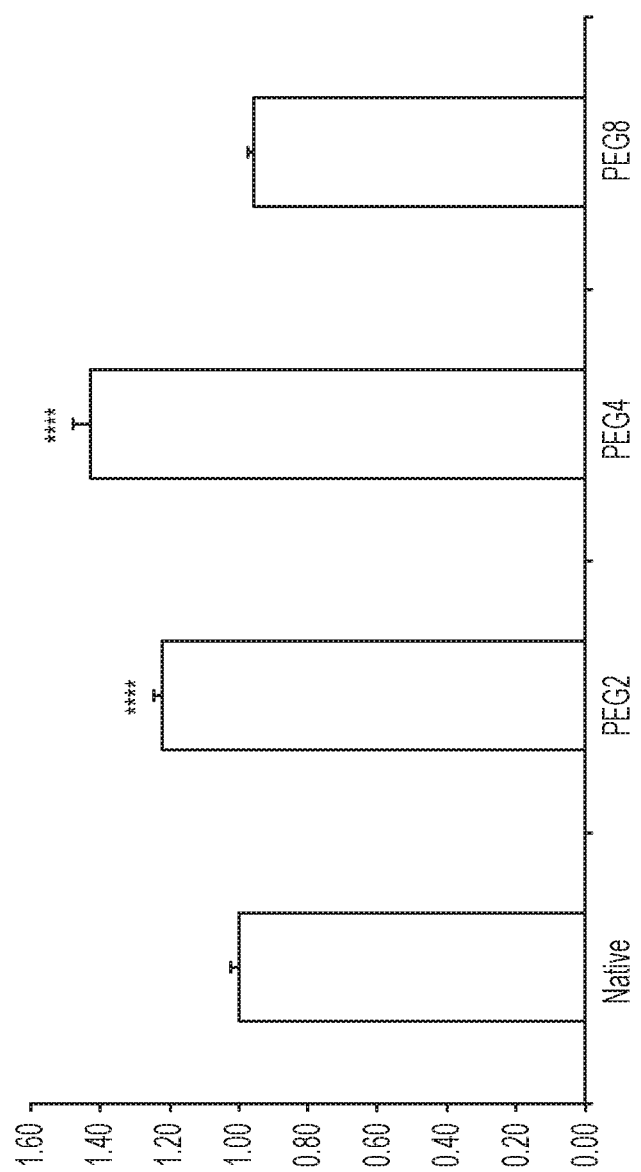
FIG. 5: Two hour internalization study of linker modified variants.
Figures 6A, 6B, 6C, 6D:
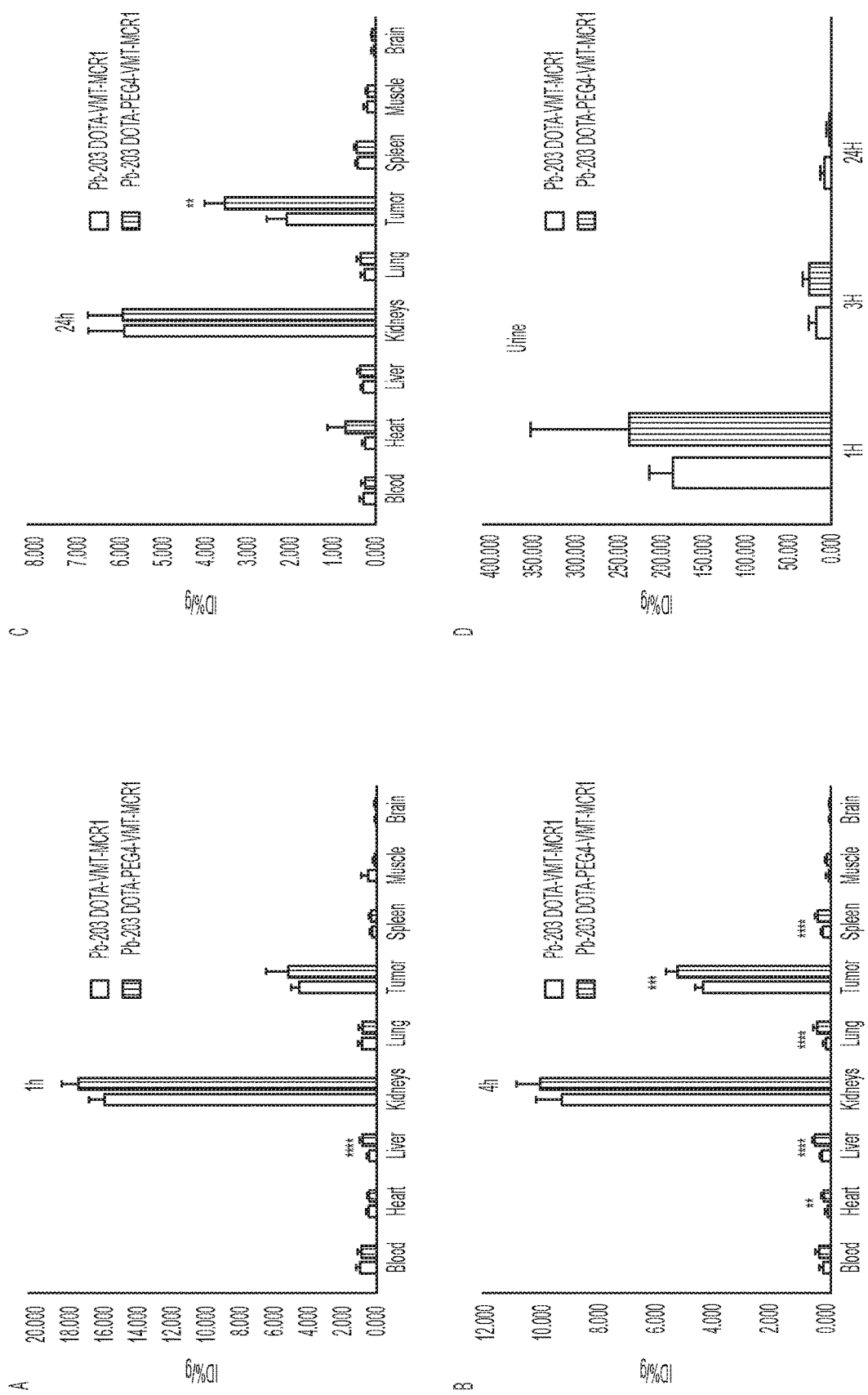
FIGS. 6A-6D: Pharmacokinetics characteristics of [203Pb]DOTA-VMT-MCR1 and [203Pb]DOTA-PEG4-VMT-MCR1 in B16/F1 murine melanoma-bearing C57 mice. Left bar of each organ or time-point measured usage of Pb-203 DOTA-VMT-MCR1; Right bar of each organ or time-point measured usage of Pb-203 DOTA-PEG4-VMT-MCR1.

FIG. 5 provides data from a two hour internalization study of linker modified variants. 200,000 count per minute (CPM) HPLC purified [Pb-203]DOTA-linker-VMT-MCR1 was added to 0.2 million B16 mice melanoma cells in 24-well plate. After 2h incubation under room temperature, media was removed. Cells were harvested and counted by NaI gamma detector. Data are expressed as internalization relative to original no-linker peptide±SEM. Significance is expressed as P<0.05*, P<0.01, P<0.001*, P<0.0001****. These results demonstrate a surprising, yet significant improvement in cellular internalization when the DOTA-VMT-MCR1 peptide is modified to include a PEG4 linker between the chelator and the peptide that reduces steric hindrances of peptide binding to the MCR1.

FIGS. 6A-6D provide the pharmacokinetics characteristics of [$^{203}$Pb]DOTA-VMT-MCR1 and [$^{203}$Pb]DOTA-PEG4-VMT-MCR1 in B16/F1 murine melanoma-bearing C57 mice. 0.037MBq of each compound was injected via tail vein. Mice were euthanized at (A) 1h, (B) 4h and (C) 24h (n=3). (D) provides data for urine samples collected ad 1h, 3h and 24 h. Tumor and organs of interest were harvested. Radioactivity was measured by NaI gamma detector. Results were expressed as percent injected dose per gram of tissue (ID %/g)+SEM. P<0.05*, P<0.01, P<0.001*, P<0.0001****. These results demonstrate a surprising, yet significant improvement in tumor accumulation and retention when the DOTA-VMT-MCR1 peptide is modified to include a PEG4 linker between the chelator and the peptide that reduces steric hindrances of peptide binding to the MCR1.

Figure 7:
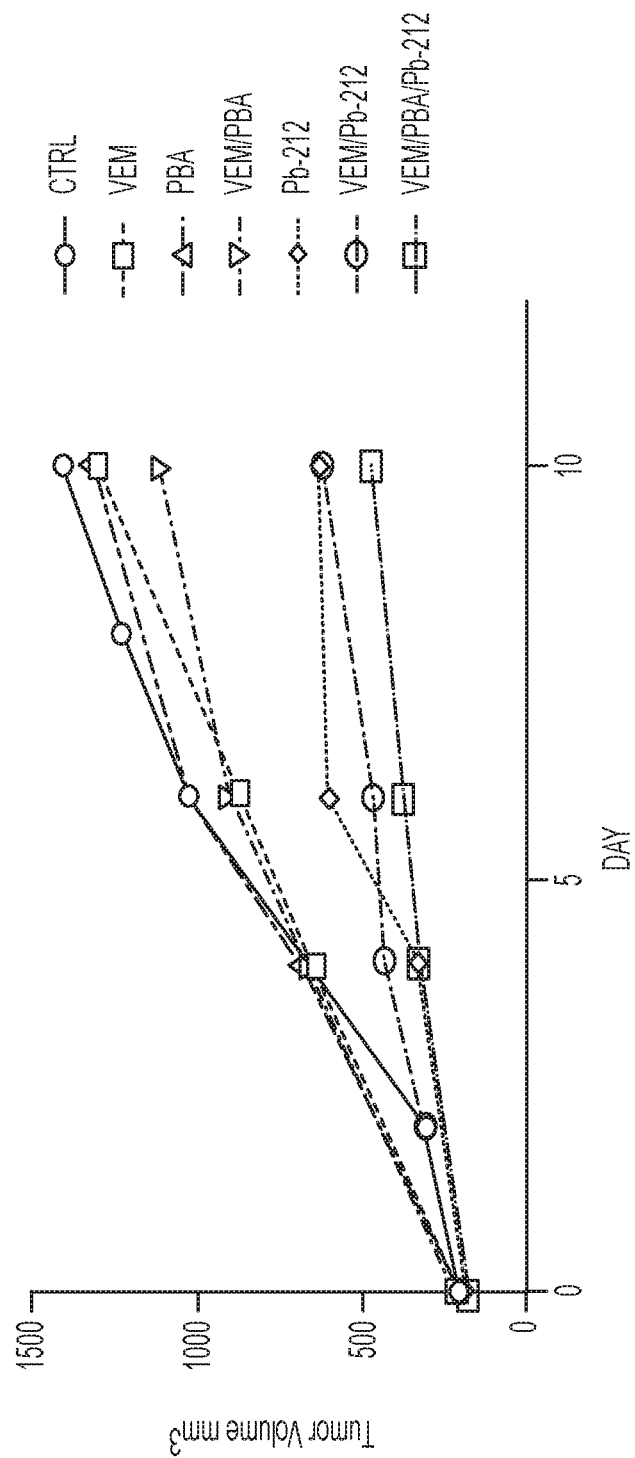
FIG. 7. [Pb-212]DOTA-PEG4-VMT-MCR1 improved therapy for metastatic melanoma tumors in mice compared to standard of care BRAF$_i$. Mice bearing A2058 tumor xenografts were administered with vehicle (CTRL); 10 mg/kg Vemurafenib (BRAF$_i$) twice a day (VEM); i.p. injected 60 mg/kg 4-PBA (PBA); i.v. injected 120 μCi of [$^{212}$Pb]DOTA-VMT-MCR1 in 3 fractions over 6 days (PB-212); or the combinations (VEM/PBA, VEM/PB-212 and VEM/PBA/VEM 212). Average tumor volumes with SDs were determined from 9-10 animals per group. Experiments conducted according to animal protocols approved by the University of Iowa Animal Care and Use Committee (IACUC).

FIG. 7. [Pb-212]DOTA-PEG4-VMT-MCR1 improved therapy for metastatic melanoma tumors in mice compared to standard of care $BRAF_i$. Mice bearing A2058 tumor xenografts were administered with vehicle (CTRL); 10 mg/kg Vemurafenib ($BRAF_i$) twice a day (VEM); i.p. injected 60 mg/kg 4-PBA (PBA); i.v. injected 120 μCi of [$^{212}$Pb]DOTA-VMT-MCR1 in 3 fractions over 6 days (PB-212); or the combinations (VEM/PBA, VEM/PB-212 and VEM/PBA/VEM 212). Average tumor volumes with SDs were determined from 9-10 animals per group. Experiments conducted according to animal protocols approved by the University of Iowa Animal Care and Use Committee (IACUC).

Figure 8:
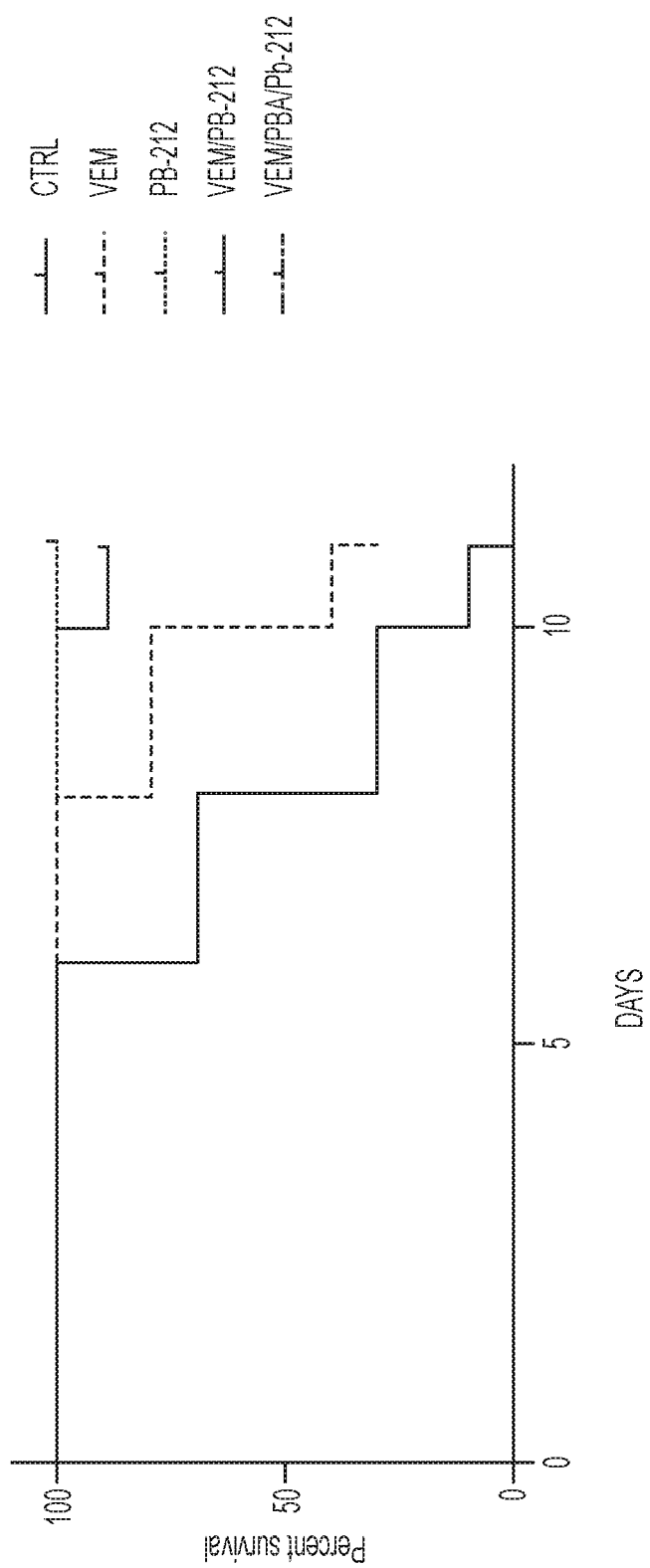
FIG. 8. [Pb-212]DOTA-PEG4-VMT-MCR1 therapy for metastatic melanoma tumors in mice improved survival compared to standard of care BRAE. Mice bearing A2058 human melanoma tumor xenografts were administered with vehicle (CTRL); 10 mg/kg Vemurafenib (BRAF$_i$) twice a day (VEM); i.p. injected 60 mg/kg 4-phenylbutyrate (PBA); i.v. injected 120 μCi of [$^{212}$Pb]DOTA-VMT-MCR1 in 3 fractions over 6 days (PB-212); or the combinations (VEM/PBA, VEM/PB-212 and VEM/PBA/VEM 212). Animal were euthanized when tumor size reached 1500 mm$^3$, loss of 30% body weight; or in case of ruptured tumor ulceration. Experiments conducted according to animal protocols approved by the University of Iowa Animal Care and Use Committee (IACUC).

FIG. 8. [Pb-212]DOTA-PEG4-VMT-MCR1 therapy for metastatic melanoma tumors in mice improved survival compared to standard of care $BRAF_i$. Mice bearing A2058 human melanoma tumor xenografts were administered with vehicle (CTRL); 10 mg/kg Vemurafenib ($BRAF_i$) twice a day (VEM); i.p. injected 60 mg/kg 4-phenylbutyrate (PBA); i.v. injected 120 μCi of [$^{212}$Pb]DOTA-VMT-MCR1 in 3 fractions over 6 days (PB-212); or the combinations (VEM/PBA, VEM/PB-212 and VEM/PBA/VEM 212). Animal were euthanized when tumor size reached 1500 $mm^3$, loss of 30% body weight; or in case of ruptured tumor ulceration. Experiments conducted according to animal protocols approved by the University of Iowa Animal Care and Use Committee (IACUC).

FIG. 9. Examples of linkers: (1) polyethyleneglycol (PEG)-based linkers with 2, 4, and 8 PEG subunits; (2) aliphatic (ALP) linkers of 2 and 4 carbons; and a piperidine (PIP) based linker with mixed characteristics.

These experiments show a significant improvement to the internalization of the conjugate on binding to the MCR1 protein on melanoma cells, which allows for significantly enhancing tumor retention and ration dose to the tumor relative to other organs and tissues. The conjugate is internalized and retained better in melanoma cells than the previous DOTA-VMT-MCR1 molecules for this purpose. Also, surprisingly, it is taken up and retained significantly better in melanoma tumors than previous molecules for this purpose (FIG. 6). Moreover, it was found that the conjugate was very surprisingly, much easier to purify the radiolabeled version (which is used of imaging ant therapy) than others previously (FIG. 4), making it much more useful for radiopharmaceutical use for clinical use for therapy and imaging of patients.

Example 3

Melanoma if detected early can be cured by surgery, but metastatic melanoma is lethal. New therapies (e.g., immunotherapy; BRAF inhibition, $BRAF_i$) and combinations extend life, but low response rates, acquired drug resistance, and serious side effects are major challenges to improving outcomes for disseminated disease (5y survival 17%). Peptide-based radionuclide therapy targeted to the melanocortin-receptor type 1 (MCR1-RT) has long been considered a promising alternative; and MCR1-RT has achieved complete responses in mouse models (B16). However, MCR1 expression is heterogeneous/low in human melanoma, and as a result, no previous MCR1-RT study has employed successfully human melanoma cell xenografts. MCR1 expression can be significantly enhanced pharmacologically in human melanoma cells via incubation with FDA-approved drugs including Buphenyl™ (4-phenylbutyrate; PBA; up to 8-fold); MAPK-targeted melanoma drugs (BRAF$_i$ and MEK$_i$); and histone deacetylase inhibitor (HDAC$_i$) Vorinostat (up to 12-fold). In vivo, combining [$^{212}$Pb]DOTA-MCR1 α-therapy with PBA and BRAE significantly improved tumor response and survival of mice bearing human melanoma tumor xenografts (A2058, 451-LU, A375) compared to BRAF$_i$ or [$^{212}$Pb]DOTA-MCR1 alone. [$^{212}$Pb]DOTA-MCR1 with PBA was also effective in mice bearing human BRAF$^{WT}$ (MeWo) tumors. Furthermore, co-injection of PBA with [$^{203}$Pb]DOTA-MCR1 significantly reduced radiopeptide accumulation in kidney (dose limiting organ); and PBA combined with BRAF$_i$ promoted cell death of BRAF$_i$-resistance melanoma cells, suggesting additional roles involving ER stress for PBA. This introduces innovative Pb-specific chelator combined with a "click-cyclized" peptide (PSC-C-MCR1) to improve tumor:kidney ratio of radionuclide uptake 7-fold. An effective therapy for metastatic melanoma is developed that combines MCR1-RT with pharmacological agents (PBA; BRAF$_i$/MEK$_i$; HDAC$_i$) that enhance MCR1 expression.

Melanoma is the fastest growing cancer incidence in the United States. Surgery combined with radiation can be curative at early stages. However, metastatic melanoma is almost uniformly fatal (5-yr survival 17%). Recent breakthrough targeted MAPK$_i$ therapies (e.g., BRAF$_i$) and immunotherapies (e.g., PD-1 inhibitors) have improved outcomes, but low response rates, acquired drug resistance, and adverse side effects limit quality of life for metastatic melanoma patients. For example, approval of immune-checkpoint inhibitor ipilimumab was based on an improvement in overall survival of only 3.7 months (overall response<15%). Combination immunotherapies have improved response (up to 61%), but grade 3/4 adverse events (up to 55%) often lead to therapy discontinuation (up to 36%). For targeted therapies, BRAF inhibitor vemurafenib was approved based on overall survival at 6 months of 84% vs 64% in the control arm (dacarbazine). Combining BRAF$_i$ with MEK inhibitors (MEK$_i$) has led to modest improvements, yet recurrence is virtually inevitable. The mechanisms of acquired drug resistance are complex, and include altered/alternative oncogenic pathways; tumor heterogeneity; and enhanced DNA repair. Melanocortin-receptor type 1 targeted radionuclide therapy (MCR1-RT) has long been considered a promising alternative treatment for melanoma; and MCR1-targeted α-particle therapy ($^{212}$Pb) has achieved complete responses in mice bearing mouse (B16) tumors that highly express MCR1. However, these studies have been confined primarily to mouse melanoma (B16) cells because MCR1 expression is heterogeneous/low in human melanoma. On the other hand, data reveal that MCR1 expression can be significantly enhanced pharmacologically in human melanoma cells via treatment with FDA-approved drug Buphenyl™ (4-phenylbutyrate; PBA; up to 8-fold). Further, incubation with FDA-approved melanoma drugs (MAPK pathway inhibitors BRAF$_i$ and MEK$_i$) and histone deacetylase inhibitor (HDAC$_i$) Vorinostat also significantly enhanced MCR1 expression (up to 12-fold). In vivo, the combination of [$^{212}$Pb]DOTA-MCR1 α-particle therapy with PBA and BRAF$_i$ significantly improved tumor response and survival of mice bearing human melanoma xenografts (A2058, 451-LUBR, A375) tumors compared to BRAF$_i$ or [$^{212}$Pb]DOTA-MCR1 alone. PBA combined with [$^{212}$Pb]DOTA-MCR1 was also effective in mice bearing human BRAF$^{WT}$ (MeWo) tumors. Furthermore, co-injection of PBA with [$^{203}$Pb] DOTA-MCR1 significantly reduced radiopeptide accumulation in kidney; and PBA combined with BRAF$_i$ promoted cell death of BRAF$_i$-resistance melanoma cells, suggesting additional roles for PBA.

MCR1-targeted radionuclide therapy has been long considered promising; and numerous α-MSH analogs that bind MCR1 using mouse B16 (F1/F10) melanoma cells that highly express the MCR1 target. However, MCR1-targeted radionuclide therapy using human melanoma cells has not been reported previously. Thus, the present experiments are novel because it is shown that MCR1 expression in human melanoma cells can be robustly enhanced pharmacologically (in vitro and in vivo) using FDA-approved melanoma BRAF$_i$/MEK$_i$ drugs, Buphenyl (PBA) and HDAC$_i$ vorinostat. It is important to note that the present data show that this innovation produces robust MCR1 expression in human melanoma tumor xenografts in mice, and that [$^{212}$Pb] DOTA-MCR1+BRAF$_i$+PBA significantly improved survival of human melanoma tumor bearing mice and significantly reduced tumor growth rates relative to standard of care BRAF$_i$ and [$^{212}$Pb]DOTA-MCR1 alone. In addition, data further resulted in the present design, synthesis, and evaluation of a new Pb-specific chelator and polyethylene-based linker that connects the chelator to the MCR1-peptide backbone that significantly improves radiolabeling efficiency; and also improves internalization of MCR1-radio-peptides.

PBA combined with [$^{212}$Pb]DOTA-MCR1 was produced robust tumor response and survival in mice bearing human BRAF$^{WT}$ (MeWo) tumors. Furthermore, co-injection of PBA with [$^{203}$Pb]DOTA-MCR1 significantly reduced radiopeptide accumulation in kidney; and PBA combined with BRAF$_i$ promoted cell death of BRAF$_i$-resistance melanoma cells, suggesting additional roles for PBA. Importantly, PBA is an FDA-approved drug prescribed at high doses (up to 27 g/day) prescribed for patients with urea disorders and has been shown to prevent ER-stress induced fibrosis of proximal tubular cells. Thus, the inclusion of PBA co-injection reduces kidney accumulation of the radiopeptides. Thus, the present invention simultaneously reduces radiation dose to the kidneys; decreases oxidative-stress and ER-stress-mediated kidney fibrosis; promotes cell death of BRAF$_i$ resistant melanoma; and enhances tumor-specific radiation dose delivery and cell killing.

The present experiments compare outcomes of MCR1-targeted radionuclide therapy for metastatic melanoma using alpha and beta-emitting radionuclides $^{177}$Ln; $^{212}$Pb; 90Y in mice bearing human melanoma tumors. Bio-distribution studies are carried out using generator gamma emitter $^{203}$Pb that has a 52h half-life to extend these studies to longer endpoints. Animal studies are conducted using immune compromised (athymic nu nu and NSG) mice (male/female) to compare directly to previous published studies of targeted radionuclide therapy for melanoma in mice.

Introduction:

Combination therapies for metastatic melanoma are emerging as common practice (e.g., BRAF$_i$ plus MEK$_i$; and combination immunotherapies), but melanoma almost invariably develops resistance. MCR1-RT has long been considered a promising alternative, but previous therapy studies have been limited to the use of B16 mouse melanoma cells that highly express the MCR1 protein, because native MCR1 expression in human melanoma is heterogeneous/low. Preliminary data was part of an investigation into the acquisition of resistance of BRAF$^{V600E}$ metastatic melanoma, which led to the discovery that incubation of FDA approved BRAE$_i$, MEK$_i$, PBA, and HDAC$_i$ drugs can be used to significantly enhance the expression of MCR1 (FIG.

10). Enhanced expression of MCR1 in response to $BRAF_i$, $MEK_i$, PBA, and $HDAC_i$ (Vorinostat, aka SAHA) is observed by RT-PCR (FIG. 10); and substantiated by flow cytometry (FIG. 11A, 11B) and by MCR1-radiopeptide binding assays (FIG. 11C, 11D)

Additional Roles for PBA Involving ER Stress.

Figures 12A, 12B, 12C, 12D:
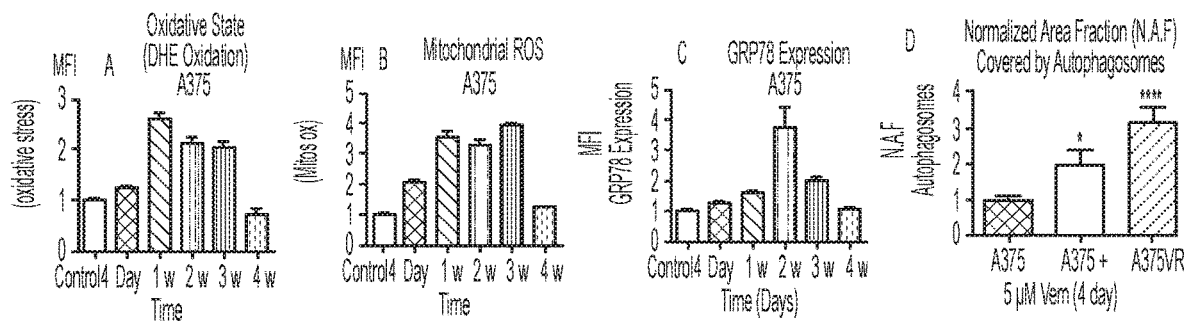
FIGS. 12A-12D. Parameters that reflect mitochondrial/cellular oxidative state; ER stress; and autophagy were monitored with the acquisition of resistance to BRAF$_i$ in A375 BRAF$_i$-sensitive melanoma cells. (A) BRAF$_i$ results in an initial increase cellular oxidative state, but decreases as cells develop resistance; (B) A similar pattern is observed in mitochondrial reactive oxygen species as measured by Mitosox ROS probe; (C) Similarly, ER-stress increases as cells develop resistance as measured by ER-stress marker GRP78 protein expression by flow cytometry; and (D) Transmission electron microscopy (TEM) was used to detect and quantify autophagy. TEM enables differentiating between lysosomes, autophagosomes, and autolysosomes. BRAF$_i$-resistant A375VR cells (which had been clonogenically selected over 1 month of BRAF$_i$ treatment) and BRAF$_i$-sensitive A375 cells were fixed overnight and en bloc stained with uranyl acetate; and quantified by standard grid-based-blinded criteria. A significant increase in the level of autophagy was observed in BRAF$_i$-resistant (A375VR) cells relative to BRAF$_i$ sensitive cells. These results support the hypothesis that acquisition of BRAF$_i$-resistance is caused by metabolic rewiring that leads to increased ER stress and autophagy that could be mediated by oxidative stress (n=3; ***p<0.001).
Figures 13A, 13B:
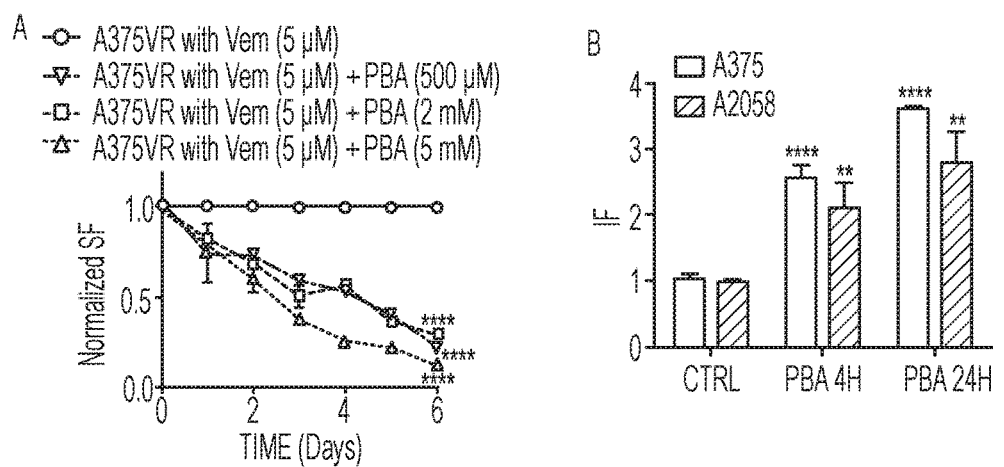
FIGS. 13A-13B. PBA treatment promotes cell death of BRAF$_i$-resistant metastatic melanoma and upregulates MCR1 expression in a time dpe. (A) BRAF$_i$-resistant A375VR cells were incubated with 5 µM vemurafenib in combination with ER-stress-relieving drug 4-PBA for up to 6 days. No change in clonogenic survival was observed for BRAF$_i$-resistant A375VR cells in the absence of PBA. However, nearly 90% clonogenic cell death was observed for BRAF$_i$-resistant A375VR treated in combination with doses of PBA as low as 500 µM. (B) Flow cytometry analysis of MCR1 expression in A2058 and A375 malignant melanoma cells. Cells were treated with 3 mmole 4-PBA for 4h and 24h (n=3). The treated and untreated (control) cells were stained with anti-MC1R-phycoerythrin (PE) monoclonal antibody conjugate. Fluorescence intensity of cells was corrected by auto-fluorescence of cells without staining and data were expressed as relative fluorescence intensity (IF) (vs. control)±SD. These data support the hypothesis that PBA can serve the dual purpose of sensitizing BRAF$_i$-resistant metastatic melanoma and upregulating MCR1 expression to enhance MCR1-RT.

Sodium 4-phenylbutyrate is a short-chain fatty-acid prodrug that is FDA-approved for patients with urea cycle disorders, and is under investigation for cancer therapy by virtue of $HDAC_i$ activity. PBA (tradename Buphenyl®) is tolerated in patients at very high doses (up to 27 g/day). The present data suggest additional roles for PBA in the proposed MCR1-RT combination therapy that involves ER stress and acquisition of resistance to BRAE. Evidence suggests complex mechanisms of acquired drug resistance in metastatic melanoma. It is believed that a primary underlying mechanism of BRAE-resistance is a metabolic switch that leads to depletion of glutathione levels and a concomitant increase in oxidative state, leading to (ER) stress (evidenced by a significant increase in ER stress marker GRP78; FIG. 12C) that initiates an autophagy response that conveys resistance to BRAE (FIGS. 12A-12D). These results are important because the data further show that PBA (known as a molecular chaperone that relieves ER stress) promotes cell death of resistant melanoma cells by inhibiting ER-stress mediated autophagy, suggesting an additional role for PBA (FIGS. 13A-13B).

PBA Promotes Cell Death of Melanoma Cells that have Acquired Resistance to $BRAF_i$ treatment.

Accumulation of misfolded-proteins causes upregulation and detachment of ER resident protein GRP78 from ER sensors proteins—activating the unfolded protein response (UPR) and downstream signaling pathways (including autophagy). These observations and initial suggest the relationship between $BRAF_i$; oxidative and ER stresses; autophagy; $BRAF_i$ resistance and MCR1 receptor expression. Thus, the potential for a pharmacological treatment that would sensitize $BRAF_i$-resistant cells to $BRAF_i$ by reducing ER-stress was considered. $BRAF_i$-resistant A375VR melanoma cells were incubated with $BRAF_i$ vemurafenib alone and in combination with ER-stress relieving PBA. Results show that incubating $BRAF_i$-resistant melanoma cells with PBA significantly sensitizes $BRAF_i$-resistant cells to $BRAF_i$, resulting in 90% clonogenic cell death (FIG. 13A). Interestingly, PBA is also known to have histone deacetylase inhibitor activity and histone deacetylase inhibitors have been recognized as pharmacological agents that can drive cell surface expression of GPCRs (e.g., MCR1). A further examination of the time dependency of PBA enhancement of MCR1 in melanoma cell lines revealed a significant (time dependent) increase in MCR1 expression in $BRAF^{V600XE}$mutant melanoma cell lines examined with PBA incubation (FIG. 13B). These results suggest that PBA enhances MCR1 expression through activity as an $HDAC_i$, but promotes cell death of resistant melanoma by acting as a chaperone to relieve the ER of misfolded proteins.

PBA Co-Injection Significantly Reduced Kidney Accumulation of [$^{203}$Pb]MCR1-Peptide in Mice Bearing Human Melanoma Tumors.

Figures 14A, 14B:
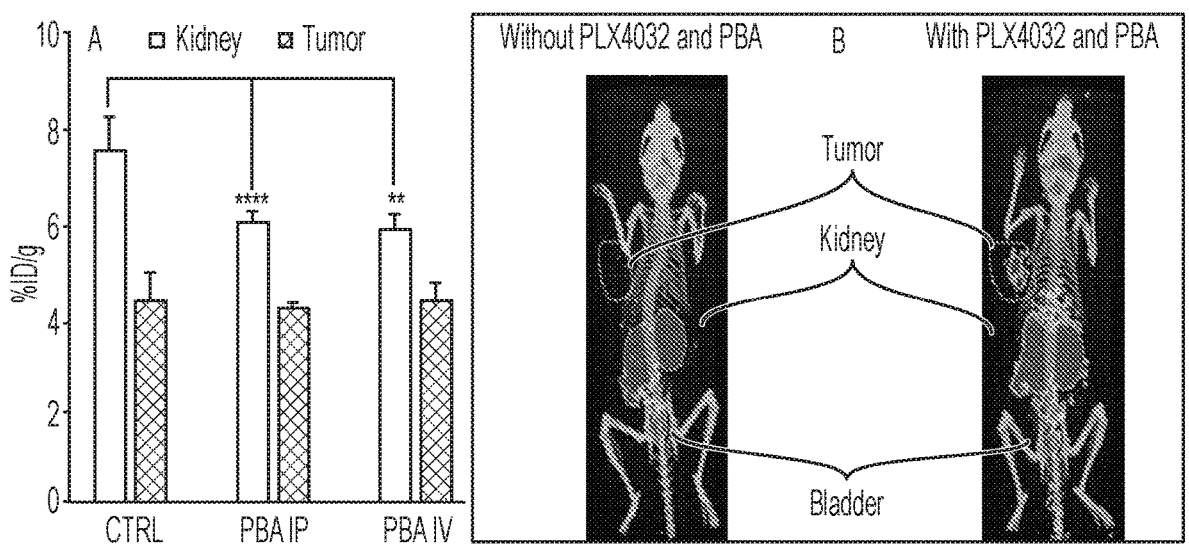

PBA relieves ER-stress through nonspecific binding to misfolded proteins in the ER. Thus, it was hypothesized that co-injection could inhibit peptide uptake in kidneys in the same fashion as amino acid co-infusions used clinically. This is reasonable because the megalin-cubulin system for reuptake and recirculation of nutrients in the proximal and distal tubules involves nonspecific binding and endocytosis of proteins, amino acids, and nutrients. results support the hypothesis that co-injection of PBA can serve to reduce kidney accumulation of radiopeptides in the kidneys (FIGS. 14A-B). It is important to note thta emerging evidence suggests a protective effect of PBA in kidney tubules, where ER-stress mediated tubular cell apoptosis is increasingly recognized as a mechanism that leads to fibrosis.

Use of PBA can Improve SPECT Imaging of Human Melanoma Tumors.

To further test the idea that PBA can be used to enhance MCR1 expression in human melanoma, SPECT/CT imaging was conducted of mice bearing human melanoma tumors (with and without pre-administration of PBA prior to the injection of a [$^{203}$Pb]DOTA-MCR1 peptide). Pre-administration of PBA and $BRAF_i$ vemurafenib significantly improved (enabled) SPECT/CT imaging of A2058 $BRAF^{V600E}$ tumor xenograft, while identical imaging settings failed to identify an identical tumor (same size) in an identical mouse (FIG. 14B).

Pharmacologically-Induced MCR1 Expression Using PBA and $BRAF_i$ Combined with MCR1-RT ($^{212}$Pb Alpha Therapy) Improves Tumor Response and Survival of Mice Bearing Human Melanoma Tumors.

Figures 15A, 15B, 15C:
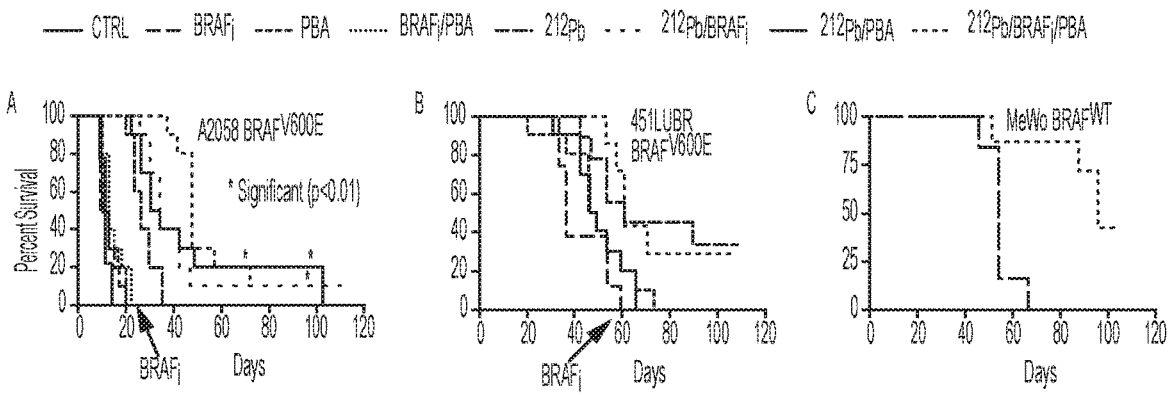
FIG. 15. Survival of mice bearing human metastatic melanoma xenografts treated with a single dose (i.v.) of [$^{212}$Pb]DOTA-MCR1, shown as $^{212}$Pb (100-140 µCi) with and without BRAF$_i$ (vemurafenib 10 mg/kg b.i.d); PBA (120 mg/kg i.p.); and combinations. BRAF$_i$ (p.o.) and PBA (i.p.) treatments were administered 3h prior to injection of [$^{212}$Pb] DOTA-MCR1 and were continued daily for the duration of experiments. Treatments were standardized to begin when tumors reach 100 mm$^3$. Mice were euthanized according to IACUC protocols (when tumors reached 1500 mm$^3$ or ulceration appeared) or at about 100d. Three possible complete responses to [$^{212}$Pb]DOTA-MCR1 were observed, pending autopsy. These data support the hypothesis that [$^{212}$Pb]DOTA-MCR1 therapy has the potential to improve outcomes for metastatic melanoma patients relative to standard of care therapy.

The in vitro MCR1 receptor expression enhancement and SPECT/CT imaging data support the hypothesis that an effective therapy for metastatic melanoma can be developed that combines MCR1-RT with pharmacological agents (PBA; $BRAF_i$/$MEK_i$; $HDAC_i$) that enhance MCR1 expression. Emerging evidence suggests that alpha-particle peptide-receptor-targeted radionuclide therapy may have advantages over beta particle therapy. In addition, alpha-particle MCR1-RT achieved complete responses in nearly 50% of mice bearing B16 mouse tumors in a previous preclinical study. Preliminary in vivo evaluation of the proposed combination MCR1-RT employed three human melanoma xenograft tumor models (FIGS. 15A-C). For these studies, human mouse tumors were induced subcutaneously and standardized to 100 mm³ prior to the initiation of treatments. Radiopeptides were produced using methods recently published. (Leachman S A, Cassidy P B, Chen S C, Curiel C, Geller A, Gareau D, Pellacani G, Grichnik J M, Malvehy J, North J, Jacques S L, Petrie T, Puig S, Swetter S M, Tofte S, Weinstock M A. Methods of Melanoma Detection. Cancer Treat Res. 2016; 167:51-105.) Animals were treated with [$^{212}$Pb]DOTA-MCR1—with and without $BRAF_1$ (vemurafenib), PBA, and combinations shown. Mice were euthanized when tumors reached 1500 mm³ or ulcerations appeared. Significant improvement in survival is observed for $BRAF^{V600E}$ human melanoma tumors in combination with $BRAF_1$ and PBA (FIG. 15A). For the 451LUBR tumor model, mice treated with [$^{212}$Pb]DOTA-MCR1 alone and mice treated with [$^{212}$Pb]DOTA-MCR1+$BRAF_i$+PBA showed robust response relative to $BRAF_i$ alone (FIG. 15B). $BRAF_i$ treatment was not included in the combination with [$^{212}$Pb]DOTA-MCR1 for MeWo $BRAF^{WT}$ tumor model because $BRAF_i$ is not indicated for $BRAF^{WT}$ patients. Nonetheless, the combination MCR1-RT with PBA significantly improved survival in these mice relative to untreated controls (FIG. 15C). These data support the hypothesis that effective therapy for metastatic melanoma can be developed that combines MCR1-RT with pharmacological agents (PBA; $BRAF_i$/$MEK_i$; $HDAC_i$) that enhance MCR1 expression.

PSC Chelator: A New Pb-Specific Chelator Improves Radiolabeling Efficiency for $^{203}$PB/$^{212}$PB THERANOSTICS.

Figures 16A, 16B, 16C, 16D:
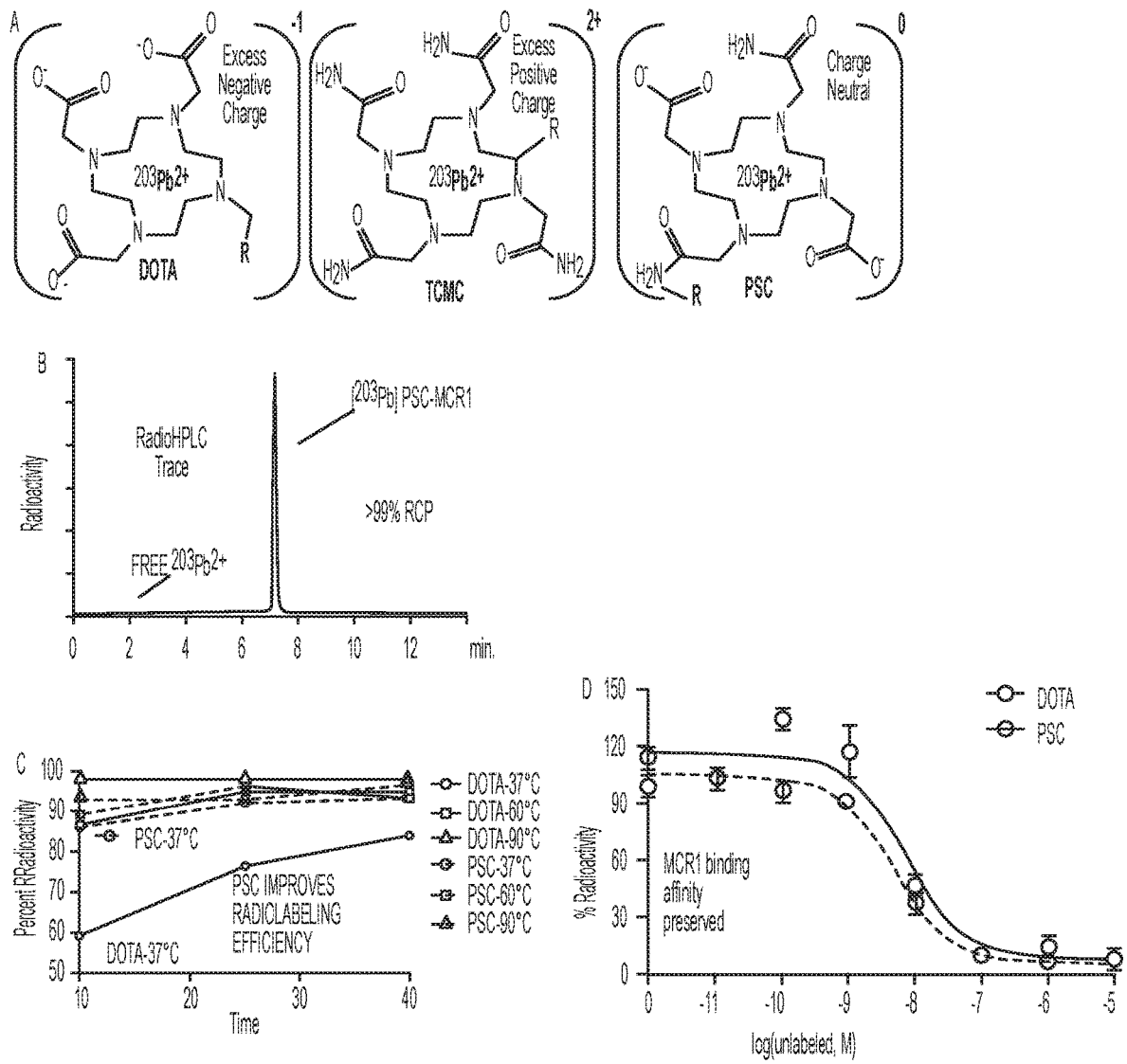
FIGS. 16A-16D. Pb-specific chelator (PSC) improves radiolabeling of peptides and does not interfere with binding of peptides to receptors. (A) DOTA and TCMC have been proposed for Pb labeling, but result in a residual charge, while the PSC is charge neutral; (B) RadioHPLC trace of [$^{203}$Pb]PSC-MCR1 peptide showing>99% radiochemical purity (RCP); (C) Rate of incorporation of $^{212}$Pb monitored at 37° C., 60° C., and 90° C. (pH 5.5 buffer); % incorporation measured by iTLC of a PSC-MCR1 peptide. Radiolabeling efficiency was nearly 90% in 10 min. at 37° C. vs.<58% for the DOTA conjugate. (D) Competitive binding assays (B16 melanoma cells expressing MCR1) showed a slightly higher binding affinity for the PCS-MCR1 conjugate compared to the DOTA-MCR1 conjugate.

The DOTA chelator has proved useful for gathering preliminary data and provides an efficient platform for trivalent radiometals ($^{68}$Ga, $^{177}$Lu, $^{90}$Y). However, the most stable oxidation state of Pb is 2+, resulting in a residual −1 charge on the chelate (FIG. 16A). A second chelator (TCMC), has been introduced commercially (FIG. 16A). Researcher concluded that DOTA was a superior chelator for Pb compared to TCMC. (Chappell L L, Dadachova E, Milenic D E, Garmestani K, Wu C, Brechbiel M W. Synthesis, characterization, and evaluation of a novel bifunctional chelating agent for the lead isotopes 203Pb and 212Pb. Nucl Med Biol. 2000; 27(1):93-100.) The authors speculated that TCMC may have low pH stability advantages in lysosomes, although the data presented suggest comparable stability to DOTA at pH 5.5 (the pH of lysosomes). Further, the TCMC-Pb complex results in a net 2$^{+}$ residual charge (FIG. 16A), which has the potential to increase kidney retention through electrostatic interaction with negatively charged surface of tubular cells. Thus, the development of the PSC is based on the chemical principle that minimizing charge (via two carboxy groups) contributes significantly to stability; and that the charge neutral complex does not increase the risk of kidney retention. Data demonstrate that PSC-peptides can be radiolabeled in high radiochemical purity (FIG. 16B); at lower temperatures than DOTA (FIG. 16C); and that PSC does not interfere with receptor binding (FIG. 16D). Thus, PSC is likely to provide the most efficient radiolabeling and stability performance for $^{203}$Pb$^{2+}$/$^{212}$Pb$^{2+}$ divalent cations. A DOTA-based conjugate of the MCR1-targeted click cyclized peptide is used for trivalent radionuclides $^{90}$Y$^{3+}$, $^{177}$Lu$^{3+}$, and $^{68}$Ga$^{3+}$.

Figure 17:
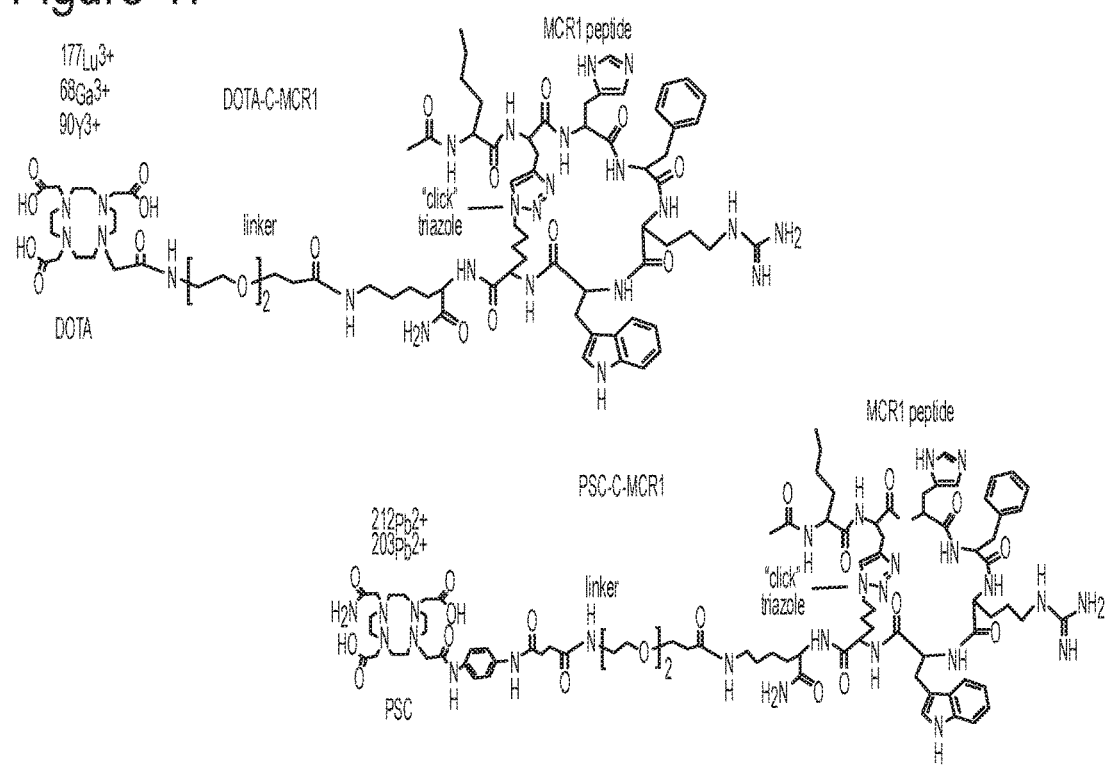
FIG. 17. Structures of the DOTA-C-MCR1 and PSC-C-MCR1 click cyclized peptides to be used for the proposed investigation. These peptides are synthesized by standard protocols using an automated peptide synthesis module and prep-HPLC purification systems. The click cyclized variants have excellent tumor targeting characteristics.

"Click"-Cyclized Peptide:

The peptide backbone selected for the proposed investigation is based on a variant that was introduced previously with the addition of new evidence for improved internalization with the inclusion of a short polyethylene glycol linker between the chelator and the peptide backbone (FIG. 17). The click cyclized MCR1 peptide (DOTA-C-MCR1) demonstrated up to 16% injected dose per gram (% ID/g) of [$^{68}$Ga]DOTA-C-MCR1 with kidney accumulation of less than 5% ID/g at 90 min. post i.v. injection in mouse studies. This peptide performance represents a 7-fold improvement in tumor:kidney ratio compared to the Re-cyclized peptide used previously. The use of the Re-cyclized peptide is for comparison to the previously published alpha-particle MCR1-targeted therapy study (using B16 mouse melanoma tumors). (Leachman S A, Cassidy P B, Chen S C, Curiel C, Geller A, Gareau D, Pellacani G, Grichnik J M, Malvehy J, North J, Jacques S L, Petrie T, Puig S, Swetter S M, Tofte S, Weinstock M A. Methods of Melanoma Detection. Cancer Treat Res. 2016; 167:51-105.) Thus, the DOTA-C-MCR1 (published previously) and new PSC-C-MCR1 peptides shown in FIG. 17 are used to take advantage of the observed improved tumor:kidney ratio.

Determination of the Time/Dose Dependence of Pharmacological Enhancement of MCR1 Expression in Human Melanoma Cell Lines.

Data show that MCR1 expression can be enhanced in human melanoma cells, but the time and dose dependence are not yet known and a broader survey of cell lines is needed. Time/dose dependence are determined by RT-PCR, flow, peptide-binding, internalization, and efflux assays in 10 human melanoma cell lines (BRAF$^{V600E}$/BRAF$^{WT}$) incubated with PBA; BRAF$_i$/MEK$_i$; HDAC$_i$ in concentrations relevant to the in vivo setting. A total of 9 human metastatic melanoma cell lines has been selected from ATCC and Wistar Cancer Institute for these studies and include: BRAF$^{V600E}$ SK-MEL-3, SH-4, SK-MEL-24, and BRAF$^{WT}$ WM1361A, WM1366, WM199; and three patient derived cell lines from the University of Iowa clinics. Concentration ranges for drugs employed are selected based on the package inserts to ensure incubations are within clinically-relevant ranges. Experiments are conducted in triplicate at least twice at all combinations.

TABLE 1

Drugs and Concentrations

| Drug | Low | Medium | High | Unit |
| --- | --- | --- | --- | --- |
| Vemurafenib (BRAF$_i$) | 1 | 5 | 10 | μM |
| Cobimetinib (MEK$_i$) | 0.1 | 0.5 | 1 | μM |
| PBA | 1 | 5 | 10 | μM |
| Vorinostat (HDAC$_i$) | 0.5 | 5 | 10 | μM |

Figure 10:
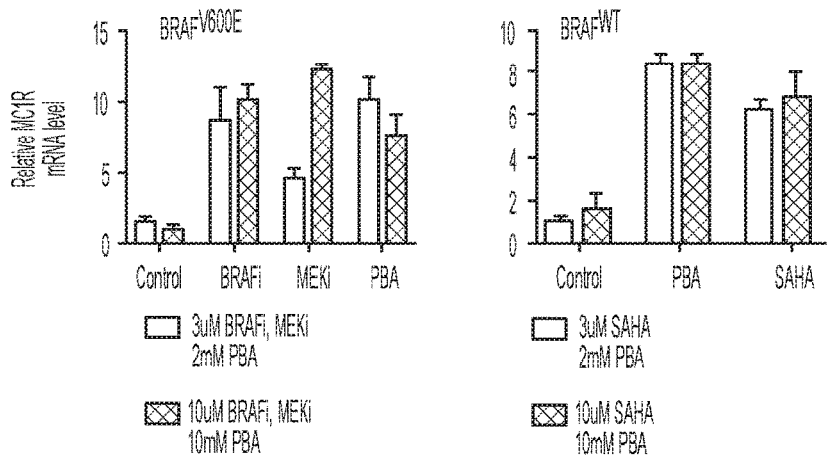
FIG. 10. Real-time PCR analysis of MC1R expression in A2058 and MEWO melanoma cells. A2058 cells were exposed to BRAF$_i$ GSK2118436, MEK$_i$ GSK1120212 and HDAC$_i$ PBA for 24h. Similarly, MEWO cells were treated with PBA and SAHA. Total RNA was isolated and reverse transcripted to cDNA. Real-time PCR was performed using 50 ng of each cDNA sample with labeled primer VIC-MC1R and FAM-NADPH. mRNA fold changes were calculated by ΔΔCt method and expressed as (n=3; Mean±SEM). These data demonstrate that the expression of MCR1 can be pharmacologically enhanced in human melanoma cells.
Figures 11A, 11B, 11C, 11D:
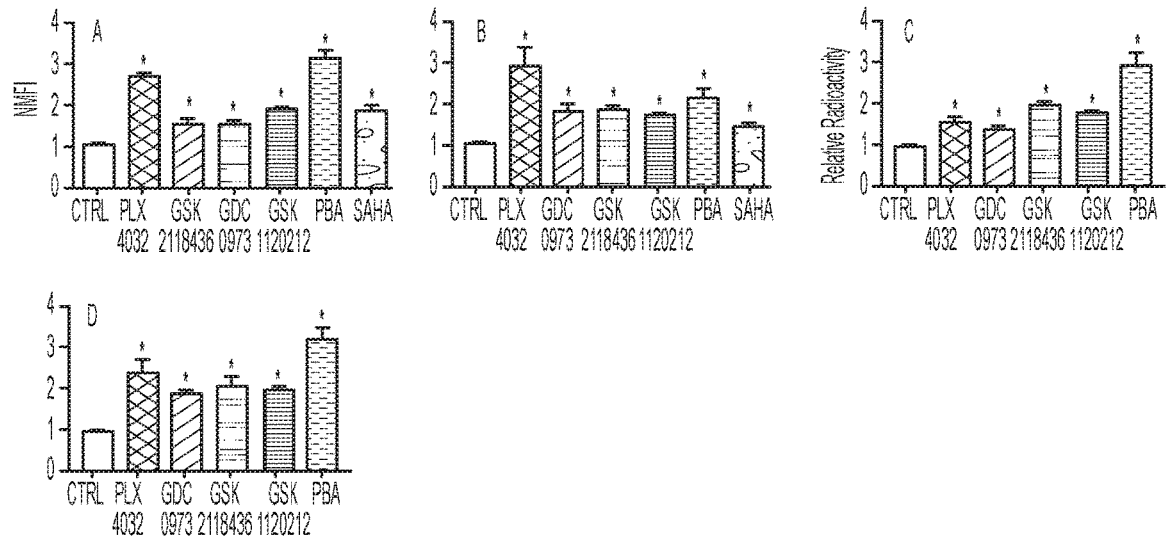
FIGS. 11A-11D. MCR1 expression can be enhanced in human melanoma cells by incubation with PBA and FDA approved melanoma drugs. (A-B) Flow cytometry analysis of MC1R expression in human melanoma cells: (A) SK-MEL3 BRAF$^{V600E}$; (B) A2058 BRAF$^{V600E}$; incubated for 4 hours with clinically-relevant concentrations of BRAF$_i$: PLX4032 (10 µM), GSK2118436 (2 µM); MEK$_i$: GDC0973 (2 µM), GSK1120212 (2 µM); 4-PBA (4 mM). Cells were stained with anti-MC1R-phycoerythrin (PE) monoclonal antibody conjugate. Fluorescence intensity was corrected by PE-conjugated isotype. Data were expressed as normalized mean fluorescence intensity (NMFI; n=4±SD; *p<0.05). (C-D) PBA-enhanced MCR1 expression increases binding of MCR1-specific peptides. (C) SK-MEL3 BRAF$^{V600E}$; and (D) A2058 BRAF$^{V600E}$ was confirmed by radiobinding assay using MCR1-specific peptide [$^{125}$I]-NDP-a-MSH following incubation for 4 hours with PBA and FDA approved drugs (as in FIG. 10). Following incubation, media was changed and cells were incubated with NDP-a-MSH for 30 min. Binding expressed as radioactivity bound relative to untreated controls (same cells) (n=4±SD; *p<0.05). These data support the hypothesis that BRAF$_i$ and PBA can be used to enhance expression of MCR1- and binding of MCR1-targeted peptides to melanoma cells.

Quantitative Real-Time PCR (MCR1 at the mRNA Level):

qPCR measurements are included to measure the change in MCR1 mRNA with changes in the concentration and incubation time for each drug and combinations (FIG. 10). These experiments are carried out as in FIG. 10 according to manufacturers' protocols, cells are seeded into 6-well plates until ~80% confluent. After drug treatments, total RNA is isolated (Qiagen RNeasy Mini Kit). 1 μg of total RNA from each cell sample is used for reverse transcription using a high capacity reverse transcription kit (Applied Biosystem). cDNA samples are kept at −80° C. until use. Upon use, cDNA templates are employed in the qRT-PCR using a Taqman Gene Expression Assay for human MC1R (Assay ID: Hs00267167_s1). Human 18S (Assay ID: Hs99999901_s1) and human GAPDH (Assay ID: Hs03929097_g1) are used as housekeeping gene controls. The qRT-PCR reaction is perform using a Taqman Fast Universal Master Mix in a 96-well plate in 20 μL. Reactions are carried out in Applied Biosystem 7900HT. mRNA level is calculated by comparative ΔΔCt method.

Receptor Binding Assay (Functional Binding to MCR1):

PCR measurements give information on the cellular response to drug treatments, but competitive binding assays convey a specific measure of changes in receptor expression (protein level) and changes in ligand-binding interactions as a result of drug treatments (FIGS. 11A-11B). After drug treatments, receptor expression is determined using synthetic α-MSH analog [$^{125}$I]-Nle$^4$-D-Phe$^7$-alpha-MSH ([$^{125}$I]-NDP-MSH) routinely as in FIG. 16D. (Martin M E, Sue O'Dorisio M, Leverich W M, Kloepping K C, Walsh S A, Schultz M K. "Click"-cyclized (68)ga-labeled peptides for molecular imaging and therapy: synthesis and preliminary in vitro and in vivo evaluation in a melanoma model system. Recent Results Cancer Res. 2012; 194:149-75; Baumhover N J, Martin M E, Parameswarappa S G, Kloepping K C, O'Dorisio M S, Pigge F C, Schultz M K. Improved synthesis and biological evaluation of chelator-modified alpha-MSH analogs prepared by copper-free click chemistry. Bioorg Med Chem Lett. 2011; 21(19):5757-61. PMCID: 3171621; Martin M E, Parameswarappa S G, O'Dorisio M S, Pigge F C, Schultz M K. A DOTA-peptide conjugate by copper-free click chemistry. Bioorg Med Chem Lett. 2010; 20(16):4805-7.) These experiments are replicated using [$^{68}$Ga]DOTA-C-MCR1 and [$^{203}$Pb]PSC-C-MCR1.

Internalization Assay:

Internalization is recognized as an important characteristic of ligand-receptor interaction for radionuclide based therapies. This is particularly important for alpha-particle therapy because internalization improves the probability of direct interaction of the alpha particle with nuclear DNA.

Alpha particle interactions with DNA have a high probability of causing double strand breaks, which leads to cell death. To determine if there are changes in the internalization of MCR1, following drug treatments, internalization assays are conducted according to routine procedures. (Martin M E, Sue O'Dorisio M, Leverich W M, Kloepping K C, Walsh S A, Schultz M K. "Click"-cyclized (68)ga-labeled peptides for molecular imaging and therapy: synthesis and preliminary in vitro and in vivo evaluation in a melanoma model system. Recent Results Cancer Res. 2012; 194:149-75; Baumhover N J, Martin M E, Parameswarappa S G, Kloepping K C, O'Dorisio M S, Pigge F C, Schultz M K. Improved synthesis and biological evaluation of chelator-modified alpha-MSH analogs prepared by copper-free click chemistry. Bioorg Med Chem Lett. 2011; 21(19):5757-61. PMCID: 3171621; Martin M E, Parameswarappa S G, O'Dorisio M S, Pigge F C, Schultz M K. A DOTA-peptide conjugate by copper-free click chemistry. Bioorg Med Chem Lett. 2010; 20(16):4805-7.) Cells are washed gently with media, ($[^{125}I]$-NDP-MSH is added and the suspension is incubated for 2h at 25° C. Binding media is aspirated and cells are rinsed and lysed in NaOH for 5 min. Cell lyses are harvested and radioactivity is measured using automatic gamma-counter (Perkin Elmer) to the determine the amount of internalized radiolabeled peptide.

Efflux Assay:

Drug efflux has been implicated in the acquisition of resistance in metastatic melanoma. It is desirable that the radioligand that is internalized remains in the cell to maximize tumor cell specific radiation dose. Conducted in the same manner as internalization assays above, except fresh media is added and cells are incubated at 37° C., 5% $CO_2$ for 30 min, 60 min, 90 min and 180 min (n=4). At each time point, culture media are aspirated, media freshened and cell lysis are harvested and radioactivity is measured using automatic gamma-counter (Perkin Elmer). These experiments are replicated using [$^{68}$Ga]DOTA-C-MCR1 and [$^{203}$Pb]PSC-C-MCR1 to determine if these differences are structural or functional MCR1 behavior changes.

CRISPR Knockouts of MCR1:

An MCR1$^{neg}$ cell line is created using the CRISPR technology and binding assays are conducted as negative controls. Briefly, A375 BRAFV600E cells are maintained in DMEM supplemented with FBS, humidified at 37° C. (5% $CO_2$) and routinely sub-cultured before reaching confluence by detachment with TrypLE Express (Invitrogen, Carlsbad, Calif.). The KN203218 MCR1 human gene knockout kit via CRISPR (containing gRNA vectors in pCAs guide) is used according to the manufacturers specifications (Origene). Recent research is revealing that CRISPR knockouts are highly specific and emerging tools are enabling an assessment of the off-target deletions. Cells are transiently transfected by calcium phosphate precipitation. Five days after transfection MCR1$^{neg}$ cells are sorted and selected from single clones for binding assays.

Determination if Pharmacological MCR1 Enhancement can Maximize Tumor:Normal Accumulation of of MCR1-Targeted Peptides in Mice Bearing Human Melanoma-Cell and Patient-Derived Xenografts.

Introduction:

Data showed that pretreatment of mice with PBA/BRAF$_i$ improved tumor response to MCR1-RT, but the optimum in vivo regimen that maximizes MCR1 expression, while minimizing radiopeptide uptake in other organs in vivo must be determined for clinical trial. Therefore in the present experiments, mice (male/female equal representation) bearing human (BRAF$^{V600E}$/BRAF$^{WT}$) melanoma tumors (6 lines ATCC/Wistar/University of Iowa patient-derived UI-PD) are pretreated with PBA/BRAF$_i$/MEK$_i$/HDAC$_i$ alone and in combinations, and the biodistribution of [$^{203}$Pb]PSC-C-MCR1 is determined by radiometric "cut and count" methodologies at a relevant time point (4h post injection chosen for a comparison). Data further suggested that PBA could be used to block accumulation of radiopeptide in the kidneys. Separate experiments examine this potential. BRAF$_i$ and MEK$_i$ are used only in experiments with the BRAF$^{V600E}$ cell lines (SK-MEL-3, SH-4, UI-PD$^{V600E}$) because these drugs are not indicated for BRAF$^{WT}$ patients. Experiments involving the BRAF$^{WT}$ cell lines (WM1361A, WM1366, UI-PD") are restricted to PBA and Vorinostat.

TABLE 2

Pretreatment doses for Aim 2 single agent testing of [$^{203}$Pb]PSC-C-MCR1 biodistribution in mice. Doses are based on the recommended dose found in the USP prescribing information.

| Drug | Dose | Unit | Daily | Route |
| --- | --- | --- | --- | --- |
| Vemurafenib (BRAF$_i$) | 10 | mg/kg | twice | PO |
| Cobimetinib (MEK$_i$) | 1 | mg/kg | once | PO |
| PBA | 60 | mg/kg | twice | IP |
| Vorinostat (HDAC$_i$) | 0.2 | mg/kg | once | PO |

Pretreatment Biodistribution Studies:

For each experiment (single agent or combination), four time points (4h, 1d, 3d, and 7d) have been selected for pretreatment prior to the injection of the [$^{203}$Pb]PSC-MCR1 to determine if receptor expression enhancement is sensitive to the duration of treatment with these drugs at clinically-relevant dosages (10 per group). Following the treatment periods, animals are injected via tail vein with [$^{203}$Pb]PSC-C-MCR1. Human metastatic melanoma xenograft cells are (1-5×10$^6$) subcutaneously (flank; athymic nu nu; 6-10 weeks) as described earlier. Martin M E, Sue O'Dorisio M, Leverich W M, Kloepping K C, Walsh S A, Schultz M K. "Click"-cyclized (68)ga-labeled peptides for molecular imaging and therapy: synthesis and preliminary in vitro and in vivo evaluation in a melanoma model system. Recent Results Cancer Res. 2012; 194:149-75.) Pretreatments commence when tumors reach sufficient size (~0.2-0.3 g). Mice are administered 10 µCi (370kBq) of [$^{203}$Pb]PSC-C-MCR1-peptide via tail vein and the animals are sacrificed at 4h post injection. Blood and organs (e.g., kidney, liver, heart, lungs, etc.) are harvested, weighed, and radioactivity analyzed by routine methods (automated high-throughput gamma counter). (Martin M E, Sue O'Dorisio M, Leverich W M, Kloepping K C, Walsh S A, Schultz M K. "Click"-cyclized (68)ga-labeled peptides for molecular imaging and therapy: synthesis and preliminary in vitro and in vivo evaluation in a melanoma model system. Recent Results Cancer Res. 2012; 194:149-75) Results are corrected to % injected dose per g (% ID/g) of tissue and blood at each time point for each tissue.

Determination if PBA Reduces Kidney Accumulation with and without Standard Amino Acid Co-Infusion:

Preliminary data support the hypothesis that co-injection of PBA with [$^{203}$Pb]MCR1-targeted peptides can reduce kidney accumulation of the radiopeptide (FIGS. 14A-B), while improving tumor accumulation in mice bearing human metastatic melanoma tumors (FIG. 14B imaging; FIGS. 15A-B therapy). The data further suggest that PBA can play a dual role in promoting cell death of BRAE-resistant melanoma and increasing the expression of MCR1 in human melanoma tumors (FIGS. 13A-B; FIG. 14B imaging). Thus, experiments are conducted to understand the approach to co-administration of PBA with [$^{203}$Pb]PSC-C-MCR1 that results in the highest tumor:kidney ratio. Preliminary published investigations of [$^{68}$Ga]DOTA-C-MCR1 achieved a tumor:kidney ratio of 3.4 at 60m post injection of the radiopharmaceutical using a B16 mouse metastatic melanoma tumor model.

Melanoma tumors are induced as described above. Preliminary experiments demonstrated that both i.p. and i.v. pre-injections of PBA could be effective in blocking kidney accumulation of the radiopeptide. Thus, for these experiments, PBA is co-administered (i.v. and/or i.p.) ranging at dosages 30, 60, 120, 240 mg/kg from 4h to 30 min. prior to injection of [$^{203}$Pb]PSC-C-MCR1. At 2h post injection, tumor and kidneys are harvested, weighed and assayed by standard gamma counter. Included in these experiments is an examination of the combination of PBA with a standard solution of amino acids (Arg+Lys) used clinically for patients receiving [$^{90}$Y]DOTA-tyr3-octreotide (DOTATOC) therapy, and the clinical protocol is used as a guide to minimize kidney accumulation of radiopeptides.

Determination of the Efficacy of Pharmacologically-Enhanced MCR1-RT Using [$^{212}$Pb] (α+β), [$^{177}$Lu] (Soft β), and [$^{90}$Y] (High-Energy β) in Mice Bearing Human Patient-Derived Xenografts.

Introduction:

Data show that MCR1 expression can be enhanced pharmacologically in human melanoma cells (FIGS. 10, 11A-D) and support the hypothesis that enhancing MCR1 expression improves in vivo imaging (FIGS. 15A-C). In addition, experiments suggest that using FDA-approved drugs PBA and BRAF$_i$/MEK$_i$ in combination with [$^{212}$Pb]MCR1 α-therapy can improve outcomes over standard of care melanoma therapy and [$^{212}$Pb]MCR1 α-therapy. However, a comparison with β-emitters and an assessment of the image-guided dosimetry approach is needed to select the most effective approach to advance to clinical trials. Therefore, radioactivity dose escalation and fractionated dose (30 day intervals x 3) studies of [$^{212}$Pb]-, [$^{177}$Lu]-, and [$^{90}$Y]-MCR1 therapies are compared in mice (male/female) bearing human xenografts and patient derived xenografts (PDX). Tumor response and survival (up to 180 days); kidney function markers (e.g., CREA/BUN); kidney pathology IHC scoring are determined. Tumor/Kidney homogenates are analyzed for oxidative/ER stress markers (e.g., DHE oxidation; protein carbonyls; PERK). A control group (n=10) of MCR1$^{neg}$ tumors (CRISPR; see above) are included to demonstrate receptor specific accumulation of the MCR1-targeted radiopeptides.

Figures 18A, 18B:
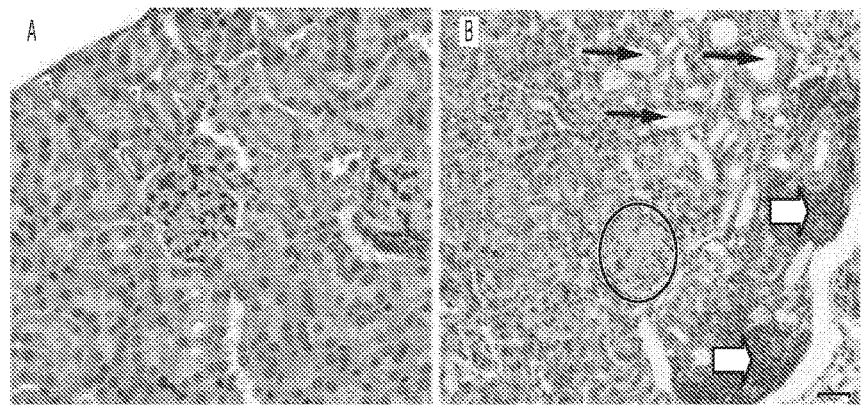
FIGS. 18A-18B. Comparison of kidney pathology analysis of (A) control and (B) kidney tissue 3 months following injection of a 100 µCi dose of [$^{212}$Pb]DOTA-MCR1. This study was conducted using the Re-cyclized MCR1 peptide and no effort was made to block kidney uptake of the radiopeptide. In B, moderate to marked, multifocal interstitial inflammation surrounding the vessels at the corticomedullary junction composed primarily of plasma cells with fewer lymphocytes (white arrows) is observed; clusters of renal tubules which appear mildly dilated and are lined by flattened epithelial cells (black arrows), some of which have very large nuclei compared to others (likely regeneration).

Dose Escalation Studies in Mice Bearing Human Melanoma Xenografts:

Data established a baseline for conducting a therapeutic safety and efficacy study using single dose administrations from 100-140 µCi (3.7-5.2 MBq) (FIGS. 15A-C) and information on potential kidney toxicity at 100 µCi (3.7MBq) (FIGS. 18A-B) for an earlier variant of the MCR1-peptide with high kidney retention characteristics. For [$^{90}$Y]DOTA-C-MCR1 and [$^{177}$Lu]DOTA-C-MCR1, previous peptide targeted dose escalation studies in mice provide a template for dose escalation presently (Table 3).

TABLE 3

Dose escalation injected radioactivity doses.

| Radionuclide | Dose Settings | Unit |
| --- | --- | --- |
| $^{212}$Pb ($t_{1/2}$ 11 h) | 1 (25), 2 (50), 4 (100), 8 (200), 12 (300) | BMq (µCi) |
| $^{177}$LU ($t_{1/2}$ 7 d) | 30 (1), 60 (1.6), 90 (205), 120 (3.2), 150 (4) | BMq (µCi) |
| $^{90}$Y ($t_{1/2}$ 64 h) | 2 (50), 5 (135), 10 (270), 20 (540), 30 (810) | BMq (µCi) |

Each of these doses (either alone or in combination with PBA or PBA+BRAF$_i$) improved survival relative to current standard of care BRAF$_i$ (vemurafenib; FIGS. 15A-C). Animal weights and behavior were monitored throughout the study and complete responses were observed in 3 cases. A more detailed understanding of the therapeutic window for each radionuclide ($^{212}$Pb; $^{177}$Lu; $^{90}$Y) is established by conducting a dose escalation study in athymic nu/nu mice bearing mouse melanoma tumors (BRAF$^{V600E}$ and BRAF$^{WT}$ tumor cell lines); with equal gender representation (n=10 per group). Treatment response is monitored for up to 180 days post injection. Tumors are inplanted as described above and treatments initiated when tumors reach 100 mm$^3$ as in FIGS. 15A-C and 16-A-D. Tumor measurements are made by routine caliper protocols twice weekly as in FIG. 19. The primarily endpoints are tumor response (defined as growth rate; maximum tumor volume; FIG. 19; PLX4032=vemurafenib) and survival (defined as days to death; or to tumors having reached 1500 mm$^3$ in size; or animals reaching a discomfort/duress endpoint according to IACUC approved protocols; FIG. 15A-C).

Statistics.

A sample size of 10 mice per group ensures at least 80% power to detect a 2.5-fold mean group difference assuming a coefficient of variation equal to 0.7. Power calculations are based on using a two-sample t-test at a single point in time with a significance level of 5%. Linear mixed effects models are used to estimate and compare group-specific tumor growth curves. The mixed effects models are expected to have higher power than the t-test since they utilize all time points. Survival curves are estimated using the Kaplan-Meier method, and compared with log-rank tests. The same methodology is employed to establish differences in normal organ toxicity parameters and causal endpoints that determine tumor response. If necessary, male and female data is pooled to increase power.

Normal Organ Toxicity Determination:

Secondary endpoints renal, hepatic, and bone marrow toxicity; and other toxicities evidenced by abnormalities in a comprehensive metabolic panel (ALP, AST, ALT, creatine kinase, albumin, total bilirubin, total protein, globulin, bilirubin—conjugated, BUN, creatinine, cholesterol, glucose, calcium, phosphorus, bicarbonate TCO$_2$, chloride, potassium, ALB/GLOB, sodium, BUN/creatinine ratio, bilirubin—unconjugated, Na/K ratio, hemolysis index, lipemia index), and complete blood count (WBC, RBC, platelets) are also important in the collective evaluation of results. The complete panel is determined at the termination of each subject, defined by death, tumor growth to IACUC maximum (1500 mm$^3$), or poor Body Conditioning Score (monitored daily according to the Ullman-Cullere and Foltz methodology). Renal function at 3d, 7d, and 30d is evaluated by measurement of Cystatin C and BUN in serum (tail snip collection and serum analysis). At the termination of each subject, pathology is conducted using paraffin embedded kidney that has been divided into three regions (inner medulla, outmedulla, cortex). Kidney injury is measured using semi-quantitative morphological analysis in kidney sections stained with Trichrome and Periodic acid-Schiff (PAS), as well as kidney injury molecule-1 (KIM-1) expression using immunofluorescence staining and western blot protein analysis. Dihydroethidium (DHE) oxidation to its red fluorescent products by $O_2.^-$ is used as a marker for steady-state levels of superoxide in cells and tissues and confirmed either using inhibition of the signal with over expression of SOD1/SOD2 or using a superoxide-specific SOD. ROS production is measured by applying DHE (see FIG. 12A) to fresh frozen kidney sections with and without GC4401 (SOD mimetic for negative control) and quantify via confocal microscopy. To confirm mitochondrial ROS production, fresh frozen kidney sections is labeled with MitSOX Red (see FIG. 12B) as well as MitoTracker Green FM (MTG). The glutathione/glutathione-disulfide (GSH/GSSG) redox couple is the most prevalent thiol redox buffer in cells, and a shift to increasing GSSG content has been shown to be an excellent marker of oxidative stress. In kidney tissue, oxidative stress parameters are measured including intracellular GSH/GSSG, 4-hydroxynonenal (4-HNE)-modified proteins (as a marker of lipid oxidation and protein damage), and NADP+/NADPH. Because oxidative-stress-induced ER stress has been implicated in tubular cell fibrosis kidney tissue is analyzed for GRP78 (FIGS. 12A-D, FIG. 20). In addition, autophagosome formation is examined as in FIGS. 12A-D to establish a potential role of autophagy as a progression to damage and fibrosis.

Tumor Pathology Analysis.

Pathology analysis (as described above for kidney tissues) is conducted on paraffin embedded tumor at the terminus of each treatment study and includes staining for the presence of MCR1 in all tumors. Measures of oxidative stress in tumors (e.g. DHE oxidation; formation of protein carbonyls); ER stress markers (PERK, IRE1-alpha, GRP78); are combined with HNE pathology analysis and microscopy (fibrosis markers, tissue damage, autophagosome formation) to establish roles for oxidative stress, ER stress, autophagy in tumor response.

Combination Therapy Using [$^{212}$Pb]MCR1-Peptide with PBA and BRAF$_i$/MEK$_i$ in Patient Derived Xenograft Models of Metastatic Melanoma in Mice (Single Dose Vs Fractionated Dose):

Final experiments of the optimized therapeutic combination are conducted using patient derived xenografts obtained. For these experiments, small 1-2 mm$^3$ cubes of human tissue from a needle biopsy is transplanted via trochar into the periscapular subcutis of female immune compromised NSG mice (Jackson Labs) aged 5-8 weeks under anesthesia (2-4 mice per tumor sample, depending on amount of biopsy tissue). These are expanded until tumor size reaches 2,000 mm$^3$ and then tumor is harvested after host animal has been euthanized. The excised tumor is sliced into 1-2 mm thick slices with a sterile blade under a dissecting microscope and viable tumor cubes 1-2 mm$^3$ are isolated from necrotic tissue. These viable tumor cubes are implanted into new NSG hosts via periscapular subcutis under anesthesia and allowed to grow until a mean volume of 200 mm$^3$ is reached at which time the PDX bearing mice are randomized into treatment groups (n=15 per group, one each for $^{212}$Pb, $^{177}$Lu, $^{90}$Y). A final test of a selected dose and combination of radiolabeled MCR1-targeted peptide in the optimized radiation dose, combined with PBA, BRAF$_i$, MEK$_i$ is conducted using 2 PDX models (BRAF$^{V600E}$ and BRAF$^{WT}$) for each radionuclide. A single dose is compared to a fractioned dose of the same radioactivity injection at 21d intervals (based on FIGS. 15A-C, 19) for each radionuclide. Tumor and normal organ analysis is conducted at the termination of each subject as described above. MCR1 pathology is conducted before implantation and at the termination of each study. A select number of control animals is implanted and euthanized to examine tumor for MCR1 at time points of 7d, 14d, 28d of each cell line (n=5 per group).

Image-Guided Therapy Evaluation and Dosimetry:

One of the potential benefits of the [$^{203}$Pb]MCR1-peptide (SPECT/CT) image-guided [$^{212}$Pb]MCR1-peptide therapy is the ability of the imaging scan to provide quantitative dosimetry information that can be used to select patients who can benefit; and to be able to use the imaging information to develop a dosimetry plan. Thus, a comparison of the dosimetric information obtained from [$^{203}$Pb]PSC-C-MCR1 imaging scans performed in the Small Animal Imaging Core is conducted on a control group of 10 PDX therapy candidates described above in advance of the therapy. Following the therapy studies, these images and associated data are examined.

Migration of $^{212}$Pb Daughter $^{212}$Bi from Parent Radionuclide in the In Vivo Setting.

Due to the recoil energy of the $^{212}$Pb-alpha decay, daughter radionuclides $^{212}$Bi $^{212}$Po, $^{208}$Tl are released from the chelator and are free to interact biochemically. In parallel experiments (for half life considerations), human metastatic melanoma tumor bearing mice (as above) are injected with 200 μCi (7.4 MBq) of [$^{212}$Pb]PSC-C-MCR1 and a biodistribution study is conducted at 1h and 4h post injection in which the tissues are analyzed by high resolution gamma-ray spectroscopy using a High-Purity Germanium Gamma Spectrometer (HPGe) for the gamma-ray spectra of each radionuclide. The gamma spectra of $^{212}$Pb and its daughters are distinguishable spectroscopically. Although there are limitations in the number of animals that can be analyzed in a given scenario, a single animal is included for these analyses with each therapy session. Biodistribution studies are conducted in which critical organs are analyzed to determine the concentration of unsupported vs. supported $^{212}$Bi in each sample to develop a detailed understanding of this potential non-targeted dose to consider in dosimetric analysis. $^{212}$Bi is used as a measure of other radionuclides because the half-lives of $^{212}$Po and $^{208}$Tl are very short and controlled by the $^{212}$Bi biodistribution.

Example 4

FIG. 21. Survival of mice bearing human metastatic melanoma xenografts (A375) treated with a single dose (i.v.) of [$^{212}$Pb]DOTA-MCR1, shown as $^{212}$Pb (~100 μCi) with and without a combination of BRAF$_i$ (vemurafenib 10 mg/kg b.i.d); PBA (120 mg/kg i.p.); and hydroxychloroquine. Treatments were standardized to begin when tumors reach 100 mm³. Mice were euthanized according to IACUC protocols (when tumors reached 1500 mm³ or ulceration appeared) or at about 100d. These data support the hypothesis that [²¹²Pb]DOTA-MCR1 therapy has the potential to improve outcomes for metastatic melanoma patients relative to standard of care therapy.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A melanoma-targeting conjugate comprising Formula I:

T-L-X wherein T is a melanocortin-1 receptor (MCR1) ligand, L is a PEG₂ linker, and X, is Pb-specific chelator (PSC), wherein the conjugate has a structural formula:

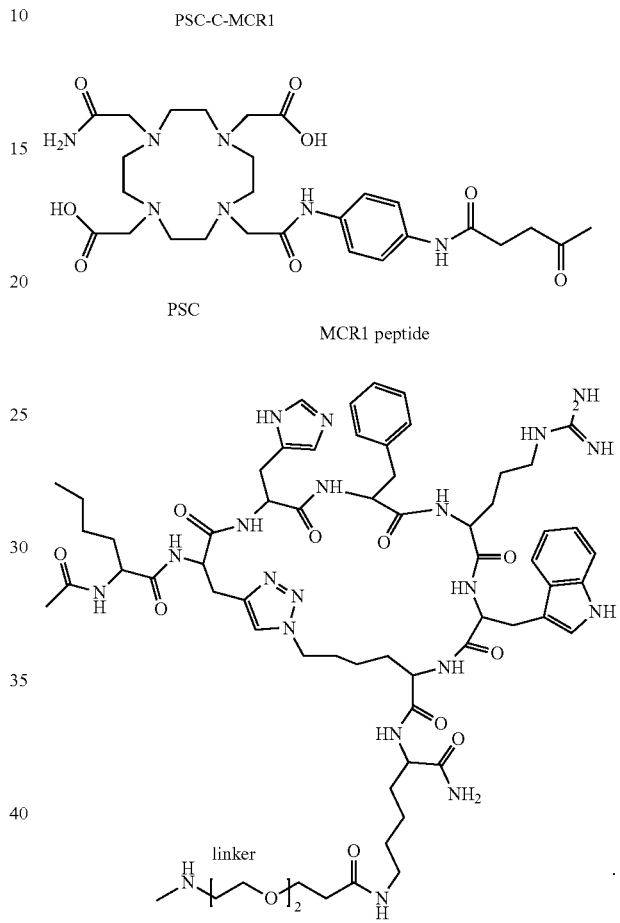

2. The conjugate of claim 1, wherein the PSC is radiolabeled.

3. The conjugate of claim 1, wherein the radiolabel is Pb-212.

4. The conjugate of claim 1, wherein the radiolabel is Pb-203.

* * * * *